US010011600B2

(12) United States Patent
Li et al.

(10) Patent No.: US 10,011,600 B2
(45) Date of Patent: Jul. 3, 2018

(54) METHODS AND COMPOSITIONS FOR INHIBITION OF RAS

(71) Applicant: ARAXES PHARMA LLC, La Jolla, CA (US)

(72) Inventors: Liansheng Li, San Diego, CA (US); Jun Feng, San Diego, CA (US); Yun Oliver Long, San Diego, CA (US); Pingda Ren, San Diego, CA (US); Yi Liu, San Diego, CA (US)

(73) Assignee: ARAXES PHARMA LLC, San Diego, CA (US)

( * ) Notice: Subject to any disclaimer, the term of this patent is extended or adjusted under 35 U.S.C. 154(b) by 0 days.

(21) Appl. No.: 15/508,387

(22) PCT Filed: Sep. 25, 2015

(86) PCT No.: PCT/US2015/052437
§ 371 (c)(1),
(2) Date: Mar. 2, 2017

(87) PCT Pub. No.: WO2016/049568
PCT Pub. Date: Mar. 31, 2016

(65) Prior Publication Data
US 2017/0247376 A1    Aug. 31, 2017

Related U.S. Application Data

(60) Provisional application No. 62/145,795, filed on Apr. 10, 2015, provisional application No. 62/055,532, filed on Sep. 25, 2014.

(51) Int. Cl.
| | |
|---|---|
| *C07D 471/04* | (2006.01) |
| *A61K 45/06* | (2006.01) |
| *C07D 239/94* | (2006.01) |
| *A61K 31/517* | (2006.01) |
| *C07D 403/04* | (2006.01) |
| *C07D 401/04* | (2006.01) |
| *C07D 403/12* | (2006.01) |
| *C07D 401/14* | (2006.01) |
| *C07D 405/12* | (2006.01) |
| *A61K 9/00* | (2006.01) |
| *C12N 9/14* | (2006.01) |

(52) U.S. Cl.
CPC .......... *C07D 471/04* (2013.01); *A61K 9/0019* (2013.01); *A61K 9/0053* (2013.01); *A61K 31/517* (2013.01); *A61K 45/06* (2013.01); *C07D 239/94* (2013.01); *C07D 401/04* (2013.01); *C07D 401/14* (2013.01); *C07D 403/04* (2013.01); *C07D 403/12* (2013.01); *C07D 405/12* (2013.01); *C12N 9/14* (2013.01); *C12Y 306/05* (2013.01)

(58) Field of Classification Search
CPC .................................................. C07D 471/04
See application file for complete search history.

(56) References Cited

U.S. PATENT DOCUMENTS

| | | |
|---|---|---|
| 3,702,849 A | 11/1972 | Cronin et al. |
| 3,752,660 A | 8/1973 | Little |
| 4,649,219 A | 3/1987 | Itoh et al. |
| 4,861,760 A | 8/1989 | Mazuel et al. |
| 4,911,920 A | 3/1990 | Jani et al. |
| 5,010,175 A | 4/1991 | Rutter et al. |
| 5,033,252 A | 7/1991 | Carter |
| 5,052,558 A | 10/1991 | Carter |
| 5,212,162 A | 5/1993 | Missel et al. |
| 5,288,514 A | 2/1994 | Ellman |
| 5,323,907 A | 6/1994 | Kalvelage |
| 5,403,841 A | 4/1995 | Lang et al. |
| 5,538,848 A | 7/1996 | Livak et al. |
| 5,539,083 A | 7/1996 | Cook et al. |
| 5,593,853 A | 1/1997 | Chen et al. |
| 5,605,798 A | 2/1997 | Koester |
| 5,731,352 A | 3/1998 | Lesieur et al. |
| 5,777,324 A | 7/1998 | Hillenkamp |
| 5,858,659 A | 1/1999 | Sapolsky et al. |
| 5,861,510 A | 1/1999 | Piscopio et al. |
| 5,863,949 A | 1/1999 | Robinson et al. |
| 5,919,626 A | 7/1999 | Shi et al. |
| 5,925,525 A | 7/1999 | Fodor et al. |
| 5,952,174 A | 9/1999 | Nikiforov et al. |
| 6,017,696 A | 1/2000 | Heller |

(Continued)

FOREIGN PATENT DOCUMENTS

| | | |
|---|---|---|
| CN | 1267291 A | 9/2000 |
| EP | 0094498 A2 | 11/1983 |

(Continued)

OTHER PUBLICATIONS

US 5,962,233, 10/1999, Livak et al. (withdrawn)
McMahon et al. (2000).*
Pinedo et al. (2000).*
American Chemical Society. STN Database. Nov. 16, 1984. RN5530-21-2.
Chemocare.com "Taxol." 2016. Available from<http://www.chemocare.com/chemotherapy/drug-info/taxol.aspx>.
European search report dated Nov. 6, 2015 for EP13775551.8.
International preliminary report on patentability dated Oct. 14, 2014 for PCT/2013/036031.
Long, D. "Taxol: An important compound with an impressive structure." 2016. Available from<https://longscience.com/2011/09/10/taxol-an-organic-compound-you-should-know-about/>.

(Continued)

*Primary Examiner* — Paul V Ward
(74) *Attorney, Agent, or Firm* — Wilson Sonsini Goodrich & Rosati

(57) ABSTRACT

Inhibitors of Ras protein, methods to modulate the activity of Ras protein, and methods of treatment of disorders mediated by Ras protein are provided. A method for regulating activity of a K-Ras, H-Ras or N-Ras mutant protein with a compound is described. Disorders that can be treated include cancer, such as hematological cancer, pancreatic cancer, MYH associated polyposis, colorectal cancer, or lung cancer.

21 Claims, 3 Drawing Sheets

(56) References Cited

U.S. PATENT DOCUMENTS

| | | | |
|---|---|---|---|
| 6,043,031 A | 3/2000 | Koester et al. |
| 6,045,996 A | 4/2000 | Cronin et al. |
| 6,051,380 A | 4/2000 | Sosnowski et al. |
| 6,068,818 A | 5/2000 | Ackley et al. |
| 6,214,872 B1 | 4/2001 | Robinson |
| 6,251,639 B1 | 6/2001 | Kurn |
| 6,903,118 B1 | 6/2005 | Biedermann et al. |
| 7,595,397 B2 | 9/2009 | Zindell et al. |
| 8,399,454 B2 | 3/2013 | Bian et al. |
| 8,426,401 B2 | 4/2013 | Bian et al. |
| 8,604,017 B2 | 12/2013 | Bian et al. |
| 8,697,684 B2 | 4/2014 | Bian et al. |
| 8,741,887 B2 | 6/2014 | Bian et al. |
| 8,759,333 B2 | 6/2014 | Connolly et al. |
| 9,227,978 B2 | 1/2016 | Ren et al. |
| 9,376,559 B2 | 6/2016 | Holtcamp et al. |
| 9,810,690 B2 | 11/2017 | Patricelli et al. |
| 2002/0169300 A1 | 11/2002 | Waterman et al. |
| 2003/0022344 A1 | 1/2003 | Williams et al. |
| 2003/0166620 A1 | 9/2003 | Lee et al. |
| 2005/0012070 A1 | 1/2005 | Inoue et al. |
| 2005/0227997 A1 | 10/2005 | Noe et al. |
| 2008/0004348 A1 | 1/2008 | Yous et al. |
| 2008/0039450 A1 | 2/2008 | Jensen et al. |
| 2009/0054402 A1 | 2/2009 | Wang et al. |
| 2009/0124636 A1 | 5/2009 | Barber et al. |
| 2009/0298075 A1 | 12/2009 | Travers et al. |
| 2010/0331300 A1 | 12/2010 | Bian et al. |
| 2011/0230476 A1 | 9/2011 | Niu et al. |
| 2011/0269244 A1 | 11/2011 | Petter et al. |
| 2011/0311447 A1 | 12/2011 | Tu et al. |
| 2011/0319290 A1 | 12/2011 | Raymond et al. |
| 2013/0012489 A1 | 1/2013 | Mederski et al. |
| 2013/0274252 A1 | 10/2013 | Pandey et al. |
| 2013/0302407 A1 | 11/2013 | Rao et al. |
| 2014/0288045 A1 | 9/2014 | Ren et al. |
| 2015/0087628 A1 | 3/2015 | Ostrem et al. |
| 2015/0239900 A1 | 8/2015 | Li et al. |
| 2016/0031898 A1 | 2/2016 | Ren et al. |
| 2016/0108019 A1 | 4/2016 | Li et al. |
| 2016/0159738 A1 | 6/2016 | Ren et al. |
| 2016/0166571 A1 | 6/2016 | Janes et al. |
| 2016/0297774 A1 | 10/2016 | Li et al. |
| 2016/0368930 A1 | 12/2016 | Ostrem et al. |
| 2017/0022184 A1 | 1/2017 | Li et al. |
| 2017/0131278 A1 | 5/2017 | Patricelli et al. |

FOREIGN PATENT DOCUMENTS

| | | |
|---|---|---|
| EP | 0606046 A1 | 7/1994 |
| EP | 0780386 A1 | 6/1997 |
| EP | 0818442 A2 | 1/1998 |
| EP | 0931788 A2 | 7/1999 |
| EP | 1004578 A2 | 5/2000 |
| EP | 1736465 A1 | 12/2006 |
| GB | 939516 A | 10/1963 |
| JP | S58203966 A | 11/1983 |
| JP | S59163372 A | 9/1984 |
| JP | 2005502623 A | 1/2005 |
| JP | 2008524154 A | 7/2008 |
| JP | 4775259 B2 | 9/2011 |
| WO | WO-9005719 A1 | 5/1990 |
| WO | WO-9119735 A1 | 12/1991 |
| WO | WO-9200091 A1 | 1/1992 |
| WO | WO-9320242 A1 | 10/1993 |
| WO | WO-9605309 A2 | 2/1996 |
| WO | WO-9627583 A1 | 9/1996 |
| WO | WO-9633172 A1 | 10/1996 |
| WO | WO-9700271 A1 | 1/1997 |
| WO | WO-9803516 A1 | 1/1998 |
| WO | WO-9807697 A1 | 2/1998 |
| WO | WO-9830566 A1 | 7/1998 |
| WO | WO-9833496 A1 | 8/1998 |
| WO | WO-9833768 A1 | 8/1998 |
| WO | WO-9834915 A1 | 8/1998 |
| WO | WO-9834918 A1 | 8/1998 |
| WO | WO-9857948 A1 | 12/1998 |
| WO | WO-9907675 A1 | 2/1999 |
| WO | WO-9929667 A1 | 6/1999 |
| WO | WO-9952889 A1 | 10/1999 |
| WO | WO-9952910 A1 | 10/1999 |
| WO | WO-9967641 A2 | 12/1999 |
| WO | WO-0039587 A1 | 7/2000 |
| WO | WO-03004480 A2 | 1/2003 |
| WO | WO-2004074283 A1 | 9/2004 |
| WO | WO-2005070891 A2 | 8/2005 |
| WO | WO-2005082892 A2 | 9/2005 |
| WO | WO-2006066948 A1 | 6/2006 |
| WO | WO-2007144394 A2 | 12/2007 |
| WO | WO-2008009078 A2 | 1/2008 |
| WO | WO-2008112440 A1 | 9/2008 |
| WO | WO-2010087399 A1 | 8/2010 |
| WO | WO-2010121918 A1 | 10/2010 |
| WO | WO-2011031896 A2 | 3/2011 |
| WO | WO-2011093524 A1 | 8/2011 |
| WO | WO-2012016082 A1 | 2/2012 |
| WO | WO-2012054716 A1 | 4/2012 |
| WO | WO-2012174489 A2 | 12/2012 |
| WO | WO-2013064068 A1 | 5/2013 |
| WO | WO-2013140148 A1 | 9/2013 |
| WO | WO-2013155223 A1 | 10/2013 |
| WO | WO-2014143659 A1 | 9/2014 |
| WO | WO-2014152588 A1 | 9/2014 |
| WO | WO-2014159837 A1 | 10/2014 |
| WO | WO-2014201435 A1 | 12/2014 |
| WO | WO-2015054572 A1 | 4/2015 |
| WO | WO-2015144001 A1 | 10/2015 |
| WO | WO-2015184349 A2 | 12/2015 |
| WO | WO-2016044772 A1 | 3/2016 |
| WO | WO-2016049524 A1 | 3/2016 |
| WO | WO-2016049565 A1 | 3/2016 |
| WO | WO-2016049568 A1 | 3/2016 |
| WO | WO-2016164675 A1 | 10/2016 |
| WO | WO-2016168540 A1 | 10/2016 |
| WO | WO-2017015562 A1 | 1/2017 |
| WO | WO-2017070256 A2 | 4/2017 |
| WO | WO-2017070256 A3 | 5/2017 |
| WO | WO-2017172979 A1 | 10/2017 |

OTHER PUBLICATIONS

Office action dated May 31, 2017 for U.S. Appl. No. 14/934,184.
International search report and written opinion dated Aug. 16, 2017 for PCT Application No. PCT/US17/24839.
Notice of allowance dated Aug. 2, 2017 for U.S. Appl. No. 15/342,100.
"Pubchem CID 10375614" Create Date: Oct. 25, 2006 (Oct. 25, 2006) Date Accessed: Aug. 8, 2017 (Aug. 8, 2017); p. 3.
Co-pending U.S. Appl. No. 15/713,297, filed Sep. 22, 2017.
Ostrem et al. K-RAS (G12C) inhibits allosterically controlled GTP affinity and effector interactions. Nature 503(7477):548-551 (2013).
Stefanachi, et al. 1-, 3- and 8-substituted-9-deazaxanthines as potent and selective antagonists at the human A2B adenosine receptor. Bioorg Med Chem. Mar. 15, 2008;16(6):2852-69.
U.S. Appl. No. 14/934,184 Office Action dated Dec. 29, 2017.
Adibekian, A., et al., Optimization and characterization of a triazole urea dual inhibitor for lysophospholipase 1 (LYPLA1) and lysophospholipase 2 (LYPLA2), in Probe Reports from the NIH Molecular Libraries Program. 2010: Bethesda (MD).
"Allen, Lloyd. The art, science, and technology of pharmaceutical compounding. American Pharmacists Association, 1997."
Al-Muhammed, et al. In-vivo studies on dexamethasone sodium phosphate liposomes. J Microencapsul. May-Jun. 1996;13(3):293-306.
"Sambrook, et al. (1989) Molecular Cloning—A Laboratory Manual (2nd ed.) vol. 1-3, Cold Spring Harbor Laboratory, Cold Spring Harbor Press, N.Y.,".
"Appel et al., "Supramolecular Cross-Linked Networks via Host-Guest Complexation with Cucurbit[8]uril," 1 Am. Chem. Soc. 132(40):14251-14260, Jul. 2010."
Arkin, et al. Binding of small molecules to an adaptive protein-protein interface. Proc Natl Acad Sci U S A. Feb. 18, 2003;100(4):1603-8. Epub Feb. 11, 2003.

(56) References Cited

OTHER PUBLICATIONS

"Sasaki, et al. "Selective Formation of Stable Triplexes Including a TA or a CG Interrupting Site with New Bicyclic Nucloside Analogues (WNA)," J. Am. Chem. Soc. 126(2):516-528, Jan. 2004."
"Ausubel et al. Current Protocols in Molecular Biology. 1987."
Bachovchin, D.A., et al., Identification of selective inhibitors of uncharacterized enzymes by high-throughput screening with fluorescent activity-based probes. Nat Biotechnol, 2009. 27(4): p. 387-94.
"Banker et al. (eds.), Modern Pharmaceutics, New York, Marcel Dekker, Inc., 1996, pp. 451 and 596. (3 pages)".
"Barbe et al., "Highly Chemoselective Metal-Free Reduction of Tertiary Amides," I Am. Chem. Soc. 130:18-19, 2008."
"Begue et al., "Ions a-Cetocarbenium. Influence De La Structure Sur L'Evolution Des Ions a-Cetocyclohexylcarbenium," Tetrahedron 31(20):2505-2511, 1975. (English Abstract Only)".
Berge, et al. Pharmaceutical salts. J Pharm Sci. Jan. 1977;66(1):1-19.
Campbell, et al. Phosphonate Ester Synthesis Using a Modified Mitsunobu Condensation. J. Org. Chem., 1994, 59 (3), pp. 658-660.
"Chemocare.com "Taxol." (c) 2016. Available from:<http://www.chemocare.com/chemotherapy/drug-info/taxol.aspx>."
Chen, et al. "Analogous" Organic Synthesis of Small-Compound Libraries: Validation of Combinatorial Chemistry in Small-Molecule Synthesis. J. Am. Chem. Soc., 1994, 116 (6), pp. 2661-2662.
Cho, et al. An unnatural biopolymer. Science. Sep. 3, 1993;261(5126):1303-5.
Chonn, et al. Recent advances in liposomal drug-delivery systems. Curr Opin Biotechnol. Dec. 1995;6(6):698-708.
Choong, et al. Identification of potent and selective small-molecule inhibitors of caspase-3 through the use of extended tethering and structure-based drug design. J Med Chem. Nov. 7, 2002;45(23):5005-22.
Co-pending U.S. Appl. No. 15/342,100, filed Nov. 2, 2016.
Cox, A.D., et al., Drugging the undruggable RAS: Mission Possible? Nat Rev Drug Discov, 2014. 13(11): p. 828-51.
"Database Pubchem Substance [Online] NCBI. Database accession No. SID22405303. Mar. 5, 2007."
Dewitt, et al. "Diversomers": an approach to nonpeptide, nonoligomeric chemical diversity. Proc Natl Acad Sci U S A. Aug. 1, 1993;90(15):6909-13.
Dillon, M.B., et al., Novel inhibitors for PRMT1 discovered by high-throughput screening using activity-based fluorescence polarization. ACS Chem Biol, 2012. 7(7): p. 1198-204.
"Duncan et al., "N-Dialkylaminoalkybiphenylamines as Antimalarial and Antischistosomal Agents," Journal of Medicinal Chemistry 12:25-29, Jan. 1969."
Erlanson, et al. Site-directed ligand discovery. Proc Natl Acad Sci U S A. Aug. 15, 2000;97(17):9367-72.
Eyles, et al. Oral delivery and fate of poly(lactic acid) microsphere-encapsulated interferon in rats. J Pharm Pharmacol. Jul. 1997;49(7):669-74.
Fingl, et al. In: The Pharmacological basis of therapeutics, Ch. 1, p. 1. 1975.
"Forbes et al., "COSMIC 2005," British Journal of Cancer 94:318-322, 2006."
Furka, et al. General method for rapid synthesis of multicomponent peptide mixtures. Int J Pept Protein Res. Jun. 1991;37(6):487-93.
Gao, et al. Controlled release of a contraceptive steroid from biodegradable and injectable gel formulations: in vitro evaluation. Pharm Res. Jun. 1995;12(6):857-63.
Gorfe, et al. Mapping the nucleotide and isoform-dependent structural and dynamical features of Ras proteins. Structure. Jun. 2008;16(6):885-96. doi: 10.1016/j.str.2008.03.009.
Hagihara, et al. Vinylogous polypeptides : an alternative peptide backbone. J. Amer. Chem. Soc. 1992, 114:6568-70.
Hall, et al. The effect of Mg2+ on the guanine nucleotide exchange rate of p21N-ras. J Biol Chem. Aug. 25, 1986;261(24):10963-5.

Hall, et al. The structural basis for the transition from Ras-GTP to Ras-GDP. Proc Natl Acad Sci U S A. Sep. 17, 2002;99(19):12138-42. Epub Sep. 4, 2002.
Hara, et al. Guanine nucleotide binding properties of purified v-Ki-ras p21 protein produced in *Escherichia coli*. Oncogene Res. May 1988;2(4):325-33.
Hardy, et al. Discovery of an allosteric site in the caspases. Proc Natl Acad Sci U S A. Aug. 24, 2004;101(34):12461-6. Epub Aug. 16, 2004.
"Hattori et al., "Neutralizing Monoclonal Antibody Against ras Oncogene Product p21 Which Impairs Guanine Nucleotide Exchange,"Mol. Cell. Biol. 7(5):1999-2002, May 1987."
Hirschmann, et al. Nonpeptidal peptidomimetics with .beta.-D-glucose scaffolding. A partial somatostatin agonist bearing a close structural relationship to a potent, selective substance P antagonist. J. Am. Chem. Soc., 1992, 114 (23), pp. 9217-9218.
Houghton, et al. Generation and use of synthetic peptide combinatorial libraries for basic research and drug discovery. Nature. Nov. 7, 1991;354(6348):84-6.
"Singh et al., "A Gene Expression Signature Associated with "K-Ras Addiction" Reveals Regulators of EMT and Tumor Cell Survival," Cancer Cell 15:489-500, Jun. 2009."
International search report and written opinion dated Apr. 13, 2017 for PCT Application No. PCT/US2016/057774.
"International search report and written opinion dated Jul. 22, 2013 for PCT/US2013/036031."
"International search report with written opinion dated Feb. 2, 2016 for PCT/US15/52437".
"International search report with written opinion dated Feb. 2, 2016 for PCT/US2015/052437".
"International search report with written opinion dated Feb. 6, 2014 for PCT/US2014/027454".
"International search report with written opinion dated Feb. 18, 2016 for PCT/US2015/051030".
"International search report with written opinion dated Mar. 2, 2016 for PCT/US2015/052427".
"International search report with written opinion dated May 30, 2016 for PCT/US2016/027673".
"International search report with written opinion dated Jul. 8, 2016 for PCT/US2016/026573".
"International search report with written opinion dated Jul. 25, 2014 for PCT/US2014/027504".
"International search report with written opinion dated Dec. 9, 2015 for PCT/US2015/052349".
"International search report with written opinion dated Dec. 17, 2014 for PCT/US2014/060036".
"Ito et al., "Regional Polysterism in the GTP-Bound Form of the Human c-Ha-Ras Protein," Biochemistry 36(30):9109-1919, Jul. 1997."
"Johnson et al., "The Chemistry of fl-Bromopropionyl Isocyanate. I. Synthesis of 1-Aryldihydrouracils," The Journal of Organic Chemistry 24(9):1391-1392, Sep. 1959."
Jones, et al. Increased frequency of the k-ras G12C mutation in MYH polyposis colorectal adenomas. Br J Cancer. Apr. 19, 2004;90(8):1591-3.
"Jordan, "Tamoxifen: A Most Unlikely Pioneering Medicine," Nature Reviews 2:205-213, Mar. 2003."
"Kelly et al., "Synthesis of Isomeric 3-Piperidinyl and 3-Pyrrolidinyl Benzo[5,6]cyclohepta[1,2-b]pyridines: Sulfonamido Derivatives as Inhibitors of Ras Prenylation," Bioorganic & Medicinial Chemistry 6:673-686, 1998."
"Kimmel, et al. Preparation of cDNA and the Generation of cDNA Libraries: Overview. Methods Enzymol. 1987;152:307-16."
Kraulis, et al. Solution structure and dynamics of ras p21.GDP determined by heteronuclear three- and four-dimensional NMR spectroscopy. Biochemistry. Mar. 29, 1994;33(12):3515-31.
"Kumar et al., "Synthesis of 3-Sulfonylamino Quinolines form 1-(2-Aminophenyl) Propargyl Alcohols through a Ag(I)-Catalyzed Hydroamination, (2+3) Cycloaddition, and an Unusual Strain-Driven Ring Expansion," Organic Letters 17(9):2226-2229, Apr. 2015."
Lachman, et al. Pharmaceutical dosage forms. vol. 1-3. Marcel Dekker, 1992.

(56) References Cited

OTHER PUBLICATIONS

"Le Picard et al., "Design and Synthesis of Naphthalenic Derivatives as Potential Inhibitors of Hydroxyindole-0-methyltransferase," Pharm. Pharmacol. Commun. 5:183-188, 1999."

Lee, et al. The mutation spectrum revealed by paired genome sequences from a lung cancer patient. Nature. May 27, 2010;465(7297):473-7. doi: 10.1038/nature09004.

Lenzen, et al. Analysis of intrinsic and CDC25-stimulated guanine nucleotide exchange of p21ras-nucleotide complexes by fluorescence measurements. Methods Enzymol. 1995;255:95-109.

Liang, et al. Parallel synthesis and screening of a solid phase carbohydrate library. Science. Nov. 29, 1996;274(5292):1520-2.

"Liu et al., "Polygonatum cyrtonema lectin induces murine fibrosarcoma L929 cell apoptosis and autophagy via blocking Ras-Raf and PI3K-Akt signaling pathways," Biochimie 92:1934-1938, 2010."

"Loboda et al., "A gene expression signature of RAS pathway dependence predicts response to PI3K and RAS pathway inhibitors and expands the population of RAS pathway activated tumors," BMC Medical Genomics 3(26):1-11, 2010."

Lone, A.M., et al., A substrate-free activity-based protein profiling screen for the discovery of selective PREPL inhibitors. J Am Chem Soc, 2011. 133(30): p. 11665-74.

"Long, D. "Taxol: An important compound with an impressive structure." (c) 2016. Available from:< https://longscience.com/2011/09/10/taxol-an-organic-compound-you-should-know-about/>".

"Malani et al., "Synthesis, characterization and in vitro screening on bacterial, fungal and malarial strain of piprazinyl cyano biphenyl based compounds," Bioorganic Chemistry 51:16-23, 2013."

Margarit, et al. Structural evidence for feedback activation by Ras.GTP of the Ras-specific nucleotide exchange factor SOS. Cell. Mar. 7, 2003;112(5):685-95.

Maurer, T., et al., Small-molecule ligands bind to a distinct pocket in Ras and inhibit SOS-mediated nucleotide exchange activity. Proc Natl Acad Sci U S A, 2012. 109(14): p. 5299-304.

"McMahon, et al. The case for colorectal cancer screening. Semin Roentgenol. Oct. 2000;35(4):325-32."

"Milburn et al., "Molecular Switch for Signal Transduction: Structural Differences Between Active and Inactive Forms of Protooncogenic ras Proteins," Science 247(4945):939-945, Feb. 1990."

Minto, et al. Pharmacokinetics and pharmacodynamics of nandrolone esters in oil vehicle: effects of ester, injection site and injection volume. J Pharmacol Exp Ther. Apr. 1997;281(1):93-102.

"Notice of allowance dated Feb. 27, 2017 for U.S. Appl. No. 14/933,734."

"Notice of allowance dated Mar. 2, 2017 for U.S. Appl. No. 14/511,425."

"Notice of allowance dated Aug. 6, 2015 for U.S. Appl. No. 14/212,656".

"Office action dated Jan. 15, 2016 for U.S. Appl. No. 14/511,425".
"Office action dated Mar. 27, 2015 for U.S. Appl. No. 14/212,656".
"Office action dated Jun. 20, 2016 for U.S. Appl. No. 14/511,425".
"Office action dated Oct. 7, 2016 for U.S. Appl. No. 14/933,734".
"Office action dated Oct. 18, 2016 for U.S. Appl. No. 14/866,147".
"Office action dated Oct. 26, 2016 for U.S. Appl. No. 15/093,951".
"Office action dated Nov. 3, 2016 for U.S. Appl. No. 14/511,425".

"Ohnmacht, Jr. et al., "Antimalarials. 5. a-Dibutylaminomethyl- and a-(2-Piperidyl)-3-quinolinemethanols," Journal of Medicinal Chemistry 14(1):17-24, 197."

Ostrem, J.M., et al., K-Ras(G12C) inhibitors allosterically control GTP affinity and effector interactions. Nature, 2013. 503(7477): p. 548-51.

Ostro, et al. Use of liposomes as injectable-drug delivery systems. Am J Hosp Pharm. Aug. 1989;46(8):1576-87.

"Pacold et al., "Crystal Structure and Functional Analysis of Ras Binding to Its Effector Phosphoinositide 3-Kinase y," Cell 103(6):931-943, Dec. 2000."

Palmioli, et al. First experimental identification of Ras-inhibitor binding interface using a water-soluble Ras ligand. Bioorg Med Chem Lett. Aug. 1, 2009;19(15):4217-22. doi: 10.1016/j.bmcl.2009.05.107. Epub May 30, 2009.

Palmioli, et al. Selective cytotoxicity of a bicyclic Ras inhibitor in cancer cells expressing K-Ras(G13D). Biochem Biophys Res Commun. Sep. 4, 2009;386(4):593-7. doi: 10.1016/j.bbrc.2009.06.069. Epub Jun. 18, 2009.

"Pardin, et al. Synthesis and evaluation of peptidic irreversible inhibitors of tissue transglutaminase. Bioorg Med Chem. Dec. 15, 2006;14(24):8379-85. Epub Sep. 27, 2006."

Pathan, et al. Lead identification for the K-Ras protein: virtual screening and combinatorial fragment-based approaches. OncoTargets and therapy 9 (2016): 2575-2584.

Patricelli, et al. Selective inhibition of oncogenic KRAS output with small molecules targeting the inactive state. Cancer discovery 6.3 (2016): 316-329.

Pautsch, A. et al., Crystal structure of the C3bot-RalA complex reveals a novel type of action of a bacterial exoenzyme. EMBO J, 2005, 24:3670-3680.

"Pedeboscq et al., "Synthesis and evaluation of apoptosis induction of thienopyrimidine compounds on KRAS and BRAF mutated colorectal cancer cell lines," Bioorganic & Medicinal Chemistry 20:6724-6731, 2012."

"Peri et al., "Arabinose-derived bicyclic amino acids: synthesis, conformational analysis and construction of an a,,(33-selective RGD peptide," I Am. Chem. Soc., Perkins Trans 1(5):638-644, Feb. 2002."

"Peri et al., "Sugar-Derived Ras Inhibitors: Group Epitope Mapping by NMR Spectroscopy and Biological Evaluation," Eur. I Org. Chem. 2006(16):3707-3720, Aug. 2006."

"Peri et al., "Synthesis of bicyclic sugar azido acids and their incorporation in cyclic peptides," Chem. Commun. 23:2303-2304, Jan. 2000."

"Pickar. Dosage Calculations. 1999."

"Spiegel et al., "Small-molecule modulation of Ras signaling," Nature Chemical Biology 10:613-622, Aug. 2014."

"Pinedo, et al. Aggressive combination therapy to cure patients with metastatic cancer. Lancet Oncol. Oct. 2000;1:72-3."

"PubChem Compound, "(2S,6R)-hexahydrofuro[3,2-blfuran-2,6-diyldicarbonochloridate:Compound Summary CID 53396983," Oct. 30, 2011, retrieved from http://pubchem.ncbi.nlm.nih.gov/compound/53396983, 6 pages."

"PubChem Compound, "(4-hydroxypiperidin-l-y1)-pyridin-4-ylmethanone: AC1L5BNJ," retrieved on Feb. 17, 2014, from http://pubchem.ncbi.nlm.nih.gov/summary/summary.cgi?cid=76837, Jul. 8, 2005, 5 pages."

"PubChem Compound, "AKOS024742141," Nov. 27, 2010, retrieved from http://pubchem.ncbi.nlm.nih.gov/compound/49702158#x304, CID 49702158, 12 pages."

"PubChem Compound, "SCHEMBL6674271," Dec. 1, 2012, retrieved from http://pubchem.ncbi.nlm.nih.gov/compound/69861127#x304, CID 69861127, 12 pages."

"PubChem Compound, "SCHEMBL6797439," Dec. 1, 2012, retrieved from http://pubchem.ncbi.nlm.nih.gov/compound/69898605#x304, CID 69898605, 12 pages."

"PubChem Compound, "Compound Summary for CID 21765509: Molecular Formula C18H21N5O8," Dec. 5, 2007, retrieved from http//pubchem.ncbi.nlm.nih.gov/compound/21765509, 4 pages."

"PubChem Compound, "Compound Summary for CID 21765511: Molecular Formula C18H2IN5O8," Dec. 5, 2007, retrieved from http://pubchem.ncbi.nlm.nih.gov/compound/21765511, 4 pages."

"PubChem Compound, "Compound Summary for CID 60018735: Molecular Formula C30I-13o013," Aug. 20, 2012, retrieved from http://pubchem.ncbi.nlm.nih.gov/compound/60018735#section=Top, 1 page."

"PubChem Compound, "Compound Summary for CID 72623693: AGN-PC-0D83J7," Jan. 9, 2014, retrieved from http://pubchem.ncbi.nlm.nih.gov/compound/72623693, 6 pages."

"PubChem Compound, "Compound Summary for CID 9897840: Molecular Formula C501446020," Oct. 25, 2006, retrieved from http://pubchem.ncbi.nlm.nih.gov/compound/9897840, 6 pages."

(56) References Cited

OTHER PUBLICATIONS

"PubChem, Substance Record for SID 44253980. Create Date: Dec. 5, 2007. Retrieved from the Internet.< URL: https://pubchem.ncbi.nlm.nih.gov/substance/44253980>".

Rao. Recent developments of collagen-based materials for medical applications and drug delivery systems. J Biomater Sci Polym Ed. 1995;7(7):623-45.

Remington. Remington's Pharmaceutical Sciences. 17th Edition. Mack Publishing Company, Easton, PA. 1985.

Remington. Remington: The science and practice of pharmacy. 20th Edition. Gennaro, Eds. Lippincott Williams & Wilkins, 2003.

Rensland, et al. Substrate and product structural requirements for binding of nucleotides to H-ras p21: the mechanism of discrimination between guanosine and adenosine nucleotides. Biochemistry. Jan. 17, 1995;34(2):593-9.

Schubbert, et al. Biochemical and functional characterization of germ line KRAS mutations. Mol Cell Biol. Nov. 2007;27(22):7765-70. Epub Sep. 17, 2007.

Shima, F., et al., Discovery of small-molecule Ras inhibitors that display antitumor activity by interfering with Ras.GTP-effector interaction. Enzymes, 2013. 34 Pt. B: p. 1-23.

Sun, Q., et al., Discovery of small molecules that bind to K-Ras and inhibit Sos-mediated activation. Angew Chem Int Ed Engl, 2012. 51(25): p. 6140-3.

"Taveras et al., "Ras Oncoprotein Inhibitors: The Discovery of Potent, Ras Nucleotide Exchange Inhibitors and the Structural Determination of a Drug-Protein Complex," Bioorganic and Medicinal Chemistry 5(1):125-133, 1997."

"Streuff et al., "First asymmetric aminohydroxylation of acrylamides," Tetrahedron: Asymmetry 16(21):3492-3496, Oct. 2005."

"Tsubaki et al., "Reduction of metastasis, cell invasion, and adhesion in mouse osteosarcoma by YM529/ONO-5920-induced blockade of the Ras/MEK/ERK and Ras/PI3K/Akt pathway," Toxicology and Applied Pharmacology 259(3):402-410, Jan. 2012."

"Tulshian et al., "Synthesis and Phosphodiesterase Activity of Carboxylic Acid Mimetics of Cyclic Guanosine 3',5'-Monophosphate," 1 Med. Chem. 36(9):1210-1220, Jan. 1993."

"Sunaga et al., "Knockdown of Oncogenic KRAS in Non-Small Cell Lung Cancers Suppresses Tumor Growth and Sensitizes Tumor Cells to Targeted Therapy," Molecular Cancer Therapeutics 10(2):336-346, Feb. 2011."

Vaughan, et al. Human antibodies with sub-nanomolar affinities isolated from a large non-immunized phage display library. Nat Biotechnol. Mar. 1996;14(3):309-14.

"Vetter et al., "The Guanine Nucleotide-Binding Switch in Three Dimensions," Science 294(5545):1299-1304, Nov. 2001."

"Vippagunta et al. Crystalline solids. Adv Drug Deliv Rev. May 16, 2001;48(1):3-26."

"Wolff, (ed.), Burger's Medicinal Chemistry and Drug Discovery, Fifth Edition, vol. 1: Principles and Practice, San Diego, California, John Wiley & Sons, 1994, pp. 975-977. (4 pages)".

"Wu et al., "Stereoselective synthesis of dioxabicycles from 1-C-allyl-2-O-benzyl-glycosides—An intramolecular cyclization between 2-O-benzyl oxygen and the allyl double bond," Can. I Chem. 84(1):597-602, Jan. 2006."

Yan et. al., Discovery and characterization of small molecules that target the GTPase Ral. Nature, 2014, 515:443-447.

"Yang et al., "Fragment-Based Discovery of Nonpeptidic BACE-1 Inhibitors Using Tethering," Biochemistry 48:4488-4496, 2009."

"Sydor et al., "Transient Kinetic Studies on the Interaction of Ras and the Ras-Binding Domain of c-Raf-1 Reveal Rapid Equilibration of the Complex," Biochemistry 37:14292-14299, 1998."

"Young et al., "Oncogenic and Wild-type Ras Play Divergent Roles in the Regulation of Mitogen-Activated Protein Kinase Signaling," Cancer Discovery 3(1):112-123, Jan. 2013."

"Zenkl et al., "Sugar-Responsive Fluorescent Nanospheres,"Macromol. Biosci. 8:146-152, 2008."

* cited by examiner

| Oncogene | Tumor Type | Cumulative Mutation Frequency (All Tumors) |
|---|---|---|
| Bcr-Abl | 90% CML | < 1% |
| EGFR | 10% NSCLC | < 5% |
| ALK | 5% NSCLC | < 1% |
| B-Raf | 66% Melanoma | < 5% |
| Flt3 | 25% AML | < 1% |
| PI3Kαα | 25% Breast; 25% Endometrial, 15% CRC | 15-20% |
| K-Ras | > 80% Pancreatic; >40% colon >20% lung | ~20% |

FIG. 3

METHODS AND COMPOSITIONS FOR INHIBITION OF RAS

CROSS REFERENCE TO RELATED APPLICATIONS

This application is a National Stage Entry of PCT/US2015/052437, filed Sep. 25, 2015, which claims the benefit of U.S. Provisional Application No. 62/055,532, filed on Sep. 25, 2014, and U.S. Provisional Application No. 62/145,795, filed on Apr. 10, 2015, each incorporated herein by reference in its entirety.

BACKGROUND

Ras represents a group of closely related monomeric globular proteins of 189 amino acids (21 kDa molecular mass) which are associated with the plasma membrane and which bind either GDP or GTP. Ras acts as a molecular switch. When Ras contains bound GDP it is in the resting or off position and is "inactive". In response to exposure of the cell to certain growth promoting stimuli, Ras is induced to exchange its bound GDP for a GTP. With GTP bound, Ras is "switched on" and is able to interact with and activate other proteins (its "downstream targets"). The Ras protein itself has a very low intrinsic ability to hydrolyze GTP back to GDP, thus turning itself into the off state. Switching Ras off requires extrinsic proteins termed GTPase-activating proteins (GAPs) that interact with Ras and greatly accelerate the conversion of GTP to GDP. Any mutation in Ras which affects its ability to interact with GAP or to convert GTP back to GDP will result in a prolonged activation of the protein and consequently a prolonged signal to the cell telling it to continue to grow and divide. Because these signals result in cell growth and division, overactive Ras signaling may ultimately lead to cancer.

Structurally, Ras proteins contain a G domain which is responsible for the enzymatic activity of Ras—the guanine nucleotide binding and the hydrolysis (GTPase reaction). It also contains a C-terminal extension, known as the CAAX box, which may be post-translationally modified and is responsible for targeting the protein to the membrane. The G domain is approximately 21-25 kDa in size and it contains a phosphate binding loop (P-loop). The P-loop represents the pocket where the nucleotides are bound in the protein, and this is the rigid part of the domain with conserved amino acid residues which are essential for nucleotide binding and hydrolysis (Glycine 12, Threonine 26 and Lysine 16). The G domain also contains the so called Switch I (residues 30-40) and Switch II (residues 60-76) regions, both of which are the dynamic parts of the protein which are often represented as the "spring-loaded" mechanism because of their ability to switch between the resting and loaded state. The key interaction is the hydrogen bonds formed by Threonine-35 and glycine-60 with the γ-phosphate of GTP which maintain Switch 1 and Switch 2 regions respectively in their active conformation. After hydrolysis of GTP and release of phosphate, these two relax into the inactive GDP conformation.

The most notable members of the Ras subfamily are HRAS, KRAS and NRAS, mainly for being implicated in many types of cancer. However, there are many other members including DIRAS1; DIRAS2; DIRAS3; ERAS; GEM; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; and RRAS2.

Mutations in any one of the three main isoforms of RAS (H-Ras, N-Ras, or K-Ras) genes are among the most common events in human tumorigenesis. About 30% of all human tumors are found to carry some mutation in Ras genes. Remarkably, K-Ras mutations are detected in 25-30% of tumors. By comparison, the rates of oncogenic mutation occurring in the N-Ras and H-Ras family members are much lower (8% and 3% respectively). The most common K-Ras mutations are found at residue G12 and G13 in the P-loop and at residue Q61.

G12C is a frequent mutation of K-Ras gene (glycine-12 to cysteine). This mutation had been found in about 13% of cancer occurrences, about 43% of lung cancer occurrences, and in almost 100% of MYH-associates polyposis (familial colon cancer syndrome). However targeting this gene with small molecules is a challenge. Accordingly, there is a need in the art for small molecules for targeting Ras (e.g., K-Ras, H-Ras and/or N-Ras) and use of the same for treatment of various diseases, such as cancer. The present invention provides these and other related advantages.

INCORPORATION BY REFERENCE

All publications and patent applications mentioned in this specification are herein incorporated by reference to the same extent as if each individual publication or patent application was specifically and individually indicated to be incorporated by reference.

SUMMARY OF THE INVENTION

In some embodiments, provided herein is a compound having the following structure (I):

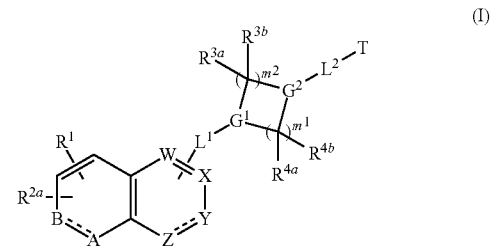

or a pharmaceutically acceptable salt, tautomer, prodrug or stereoisomer thereof, wherein: A is $CR^1$, $CR^{2b}$, $NR^5$ or S; B is a bond, $CR^1$ or $CR^{2c}$; $G^1$ and $G^2$ are each independently N or CH; W, X and Y are each independently N, $NR^5$ or $CR^6$; Z is a bond, N or $CR^6$; $L^1$ is a bond or $NR^7$; $L^2$ is a bond or alkylene; $R^1$ is H, cyano, halo, heterocyclyl, heteroaryl, aryloxy or aryl; $R^{2a}$, $R^{2b}$ and $R^{2c}$ are each independently H, halo, hydroxyl, $C_1$-$C_6$ alkyl, $C_1$-$C_6$ haloalkyl, $C_3$-$C_8$ cycloalkyl or aryl; $R^{3a}$ and $R^{3b}$ are, at each occurrence, independently H, —OH, —$NH_2$, —$CO_2H$, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl; or $R^{3a}$ and $R^{3b}$ join to form a carbocyclic or heterocyclic ring; or $R^{3a}$ is H, —OH, —$NH_2$, —$CO_2H$, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl, and $R^{3b}$ joins with $R^{4b}$ to form a carbocyclic or heterocyclic ring; $R^{4a}$ and $R^{4b}$ are, at each occurrence, independently H, —OH, —$NH_2$, —$CO_2H$, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl; or $R^{4a}$ and $R^{4b}$ join to form a carbocyclic or heterocyclic ring; or $R^{4a}$ is H, —OH, —NH$_2$, —CO$_2$H, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl, and $R^{4b}$ joins with $R^{3b}$ to form a carbocyclic or heterocyclic ring; $R^5$ and $R^7$ are each independently H or $C_1$-$C_6$ alkyl; $R^6$ is, at each occurrence, independently H, oxo, cyano, cyanoalkyl, amino, aminylalkyl, aminylalkylaminyl, aminocarbonyl, alkylaminyl, halo alkylamino, hydroxylalkyamino, amindinylalkyl, amidinylalkoxy, amindinylalkylaminyl, guanidinylalkyl, guanidinylalkoxy, guanidinylalkylaminyl, $C_1$-$C_6$ alkoxy, aminylalkoxy, alkylcarbonylaminylalkoxy, $C_1$-$C_6$ alkyl, heterocyclyl, heterocyclyloxy, heterocyclylalkyloxy, heterocyclylamino, heterocyclylalkylamino, heteroaryl, heteroaryloxy, heteroarylalkyloxy, heteroarylamino, heteroarylalkylamino, aryl, aryloxy, arylamino, arylalkylamino, arylalkyloxy or a bond to $L^1$; $m^1$ and $m^2$ are each independently 1, 2 or 3; ---- indicates a single or double bond such that all valences are satisfied; and T is a polar group capable of forming a complex with a Ras protein via an interaction other than one resulting in a covalent bond with the cysteine residue at position 12 of a K-Ras, H-Ras or N-Ras G12C mutant protein; wherein at least one of W, X, Y or Z is $CR^6$ where $R^6$ is a bond to $L^1$; and provided that when $R^1$, $R^{2a}$, $R^{2b}$ and $R^{2c}$ are all independently selected from H and halo, then X and Z are both N and at least one of $R^{3a}$, $R^{3b}$, $R^{4a}$ or $R^{4b}$ is hot H, and provided that at least one of $R^{2a}$, is not H when $R^1$ is pyridyl.

In some embodiments, the compound has the following structure (I'):

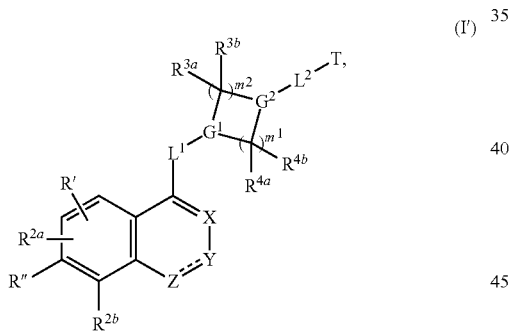
(I')

wherein R' is $R^1$ and R" is $R^{2c}$ or R' is H and R" is $R^1$.

In some embodiments, the compound has one of the following structures (I'b), (I'c), (I'd) or (I'e):

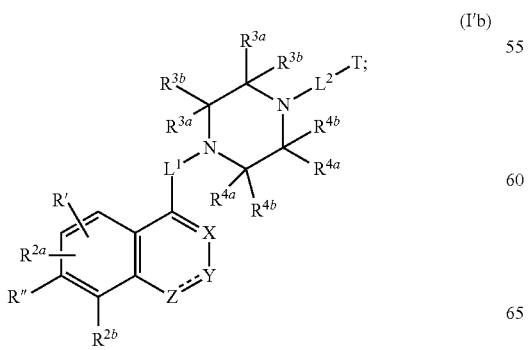
(I'b)

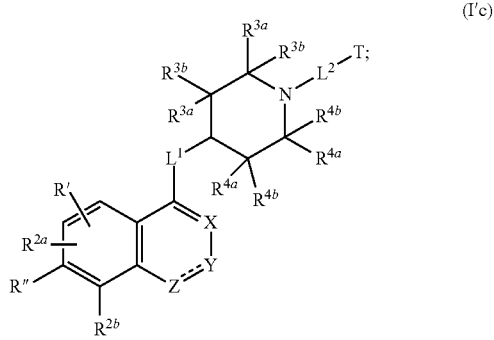
(I'c)

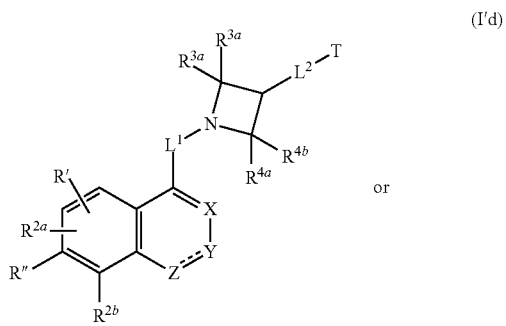
(I'd)

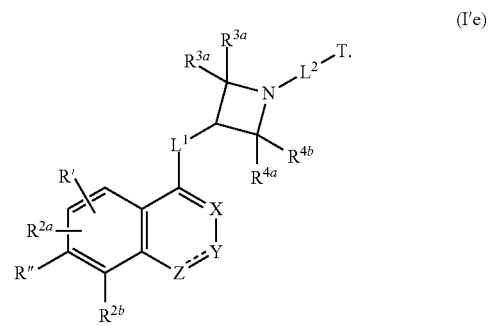
(I'e)

In some embodiments, the compound has one of the following structures (I'f), (I'g), (I'h) or (I'i):

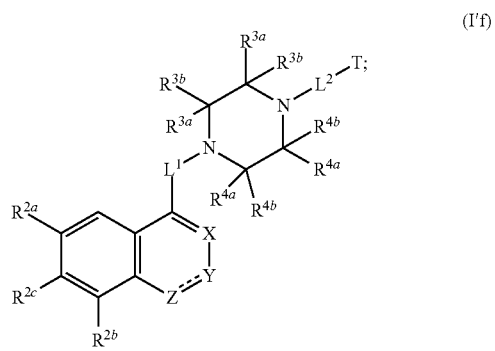
(I'f)

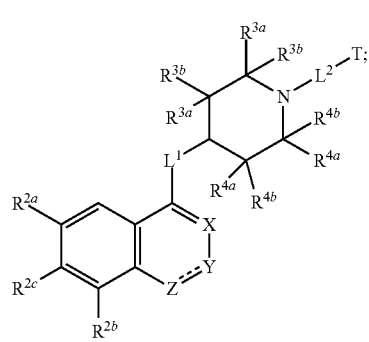
(I'g)
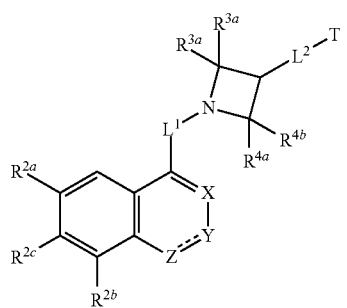
(I'h) or
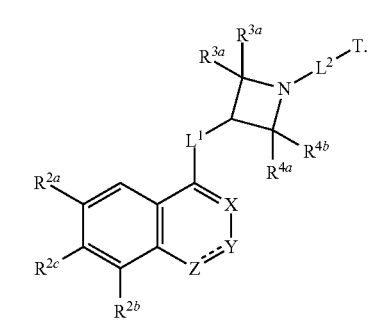
(I'i)
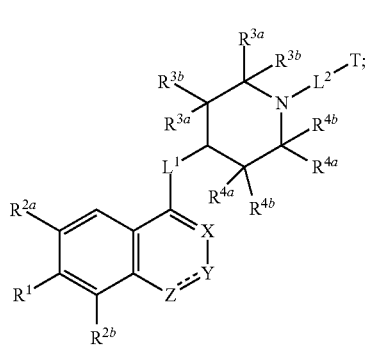
(I'k)
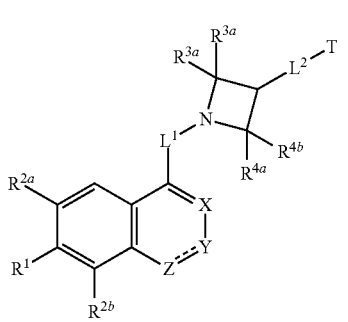
(I'l) or
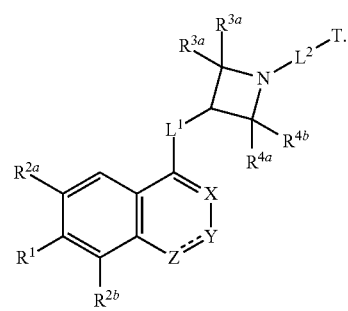
(I'm)
In some embodiments, compound has one of the following structures (I'j), (I'k), (I'l) or (I'm):
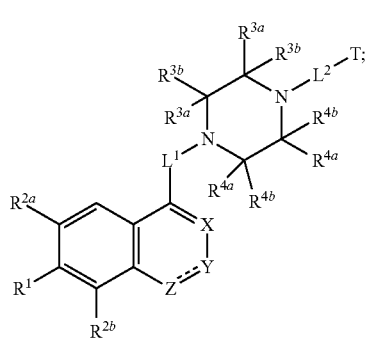
(I'j)
In some embodiments, the compound has the following structure (I"):
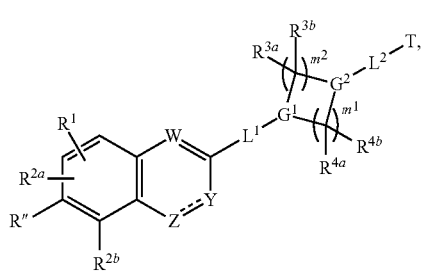
(I")
wherein R' is $R^1$ and R" is $R^{2c}$ or R' is H and R" is $R^1$.

In some embodiments, the compound has one of the following structures (I″b), (I″c), (I″d) or (I″e):
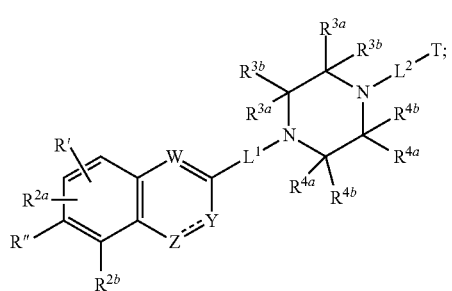
(I′b)
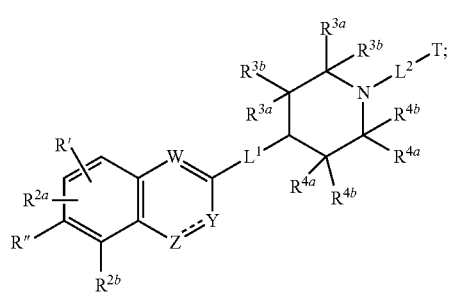
(I′c)
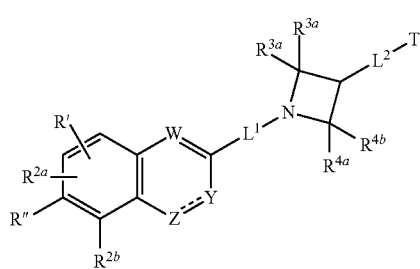
(I′d)
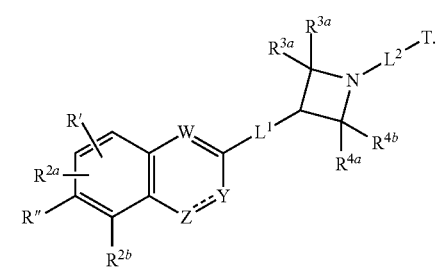
(I′e)
In some embodiments, the compound has one of the following structures (I″f), (I″g), (I″h) or (I″i):
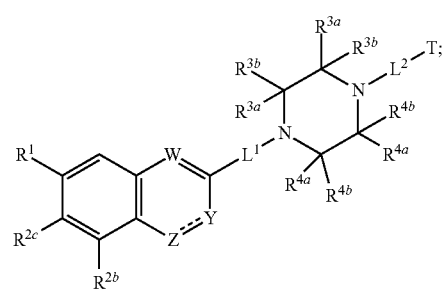
(I″f)
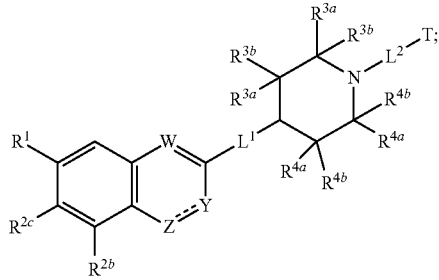
(I″g)
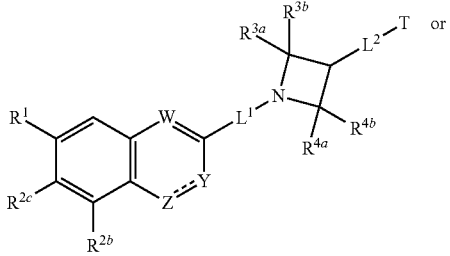
(I″h)
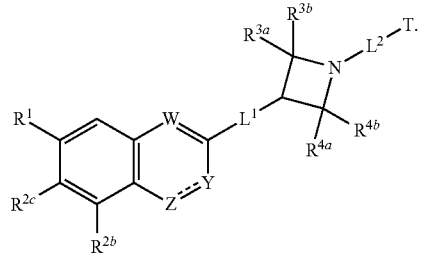
(I″i)
In some embodiments, the compound has one of the following structures (I″j), (I″k), (I″l) or (I″m):
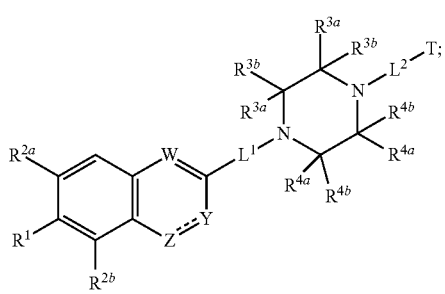
(I″j)
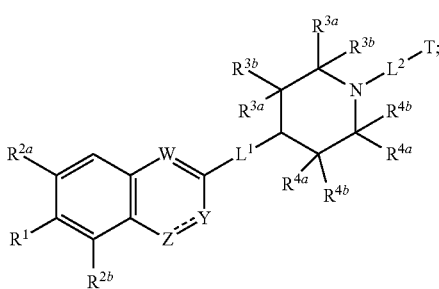
(I″k)

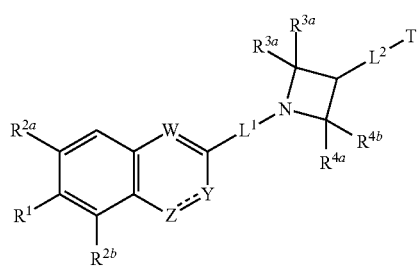
(I″l)
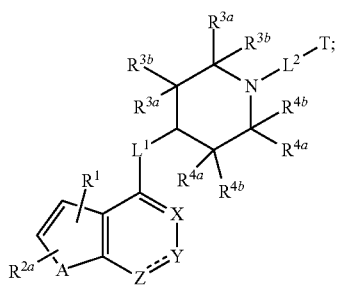
(I‴c)
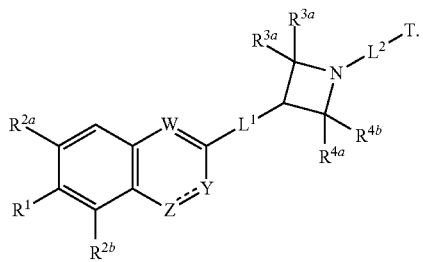
(I″m)
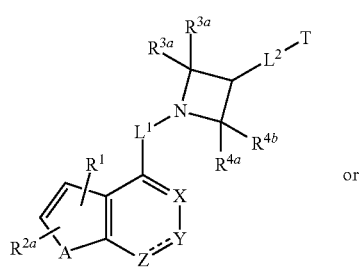
(I‴d)
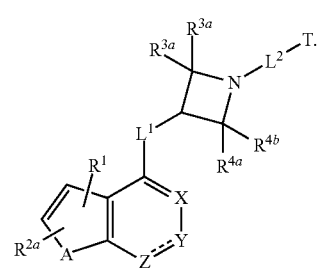
(I‴e)
In some embodiments, the compound has the following structure (I‴):
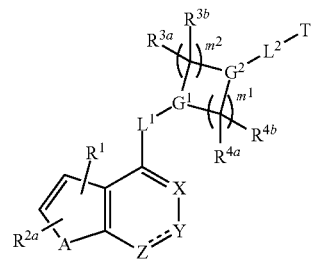
(I‴)
wherein A is NH or S.
In some embodiments, the compound has one of the following structures (I‴b), (I‴c), (I‴d) or (I‴e):
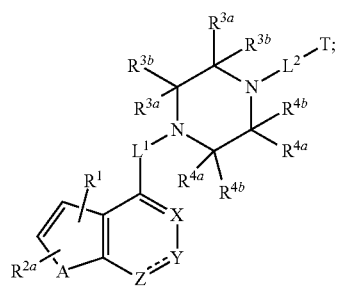
(I‴b)
In some embodiments, the compound has one of the following structures (I‴f), (I‴g), (I‴h) or (I‴i):
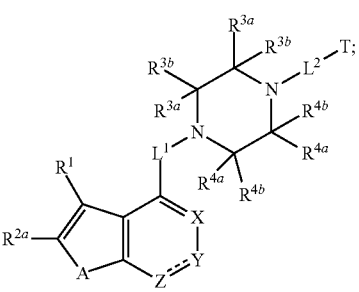
(I‴f)
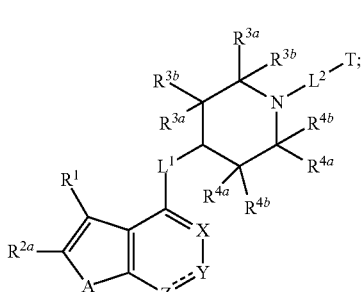
(I‴g)

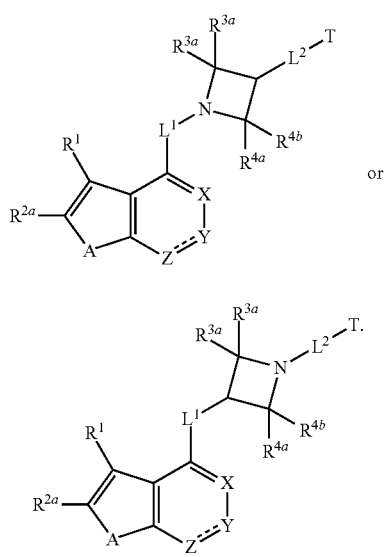

In some embodiments of the compounds provided herein, $R^1$ is aryl, for example $R^1$ is phenyl, or $R^1$ is napthyl. In some embodiments, $R^1$ is unsubstituted. In other embodiments, $R^1$ is substituted with one or more substituents. In some embodiments, the substituents are selected from halo, cyano, cyano$C_1$-$C_6$alkyl, cyano$C_3$-$C_8$cycloalkyl, hydroxyl, $C_1$-$C_6$alkyl, $C_1$-$C_6$alkylcycloalkyl, $C_2$-$C_6$alkynyl, $C_1$-$C_6$alkoxy, $C_1$-$C_6$haloalkoxy, $C_1$-$C_6$alkylaminyl, $C_1$-$C_6$alkylcarbonylaminyl, $C_1$-$C_6$hydroxylalkyl, $C_1$-$C_6$haloalkyl, $C_1$-$C_6$alkoxyalkyl, aminosulfone, aminocarbonyl, aminocarbonyl$C_1$-$C_6$alkyl, aminocarbonyl$C_3$-$C_8$cycloalkyl, $C_1$-$C_6$alkylaminocarbonyl, $C_3$-$C_8$cycloalkylaminocarbonyl, $C_3$-$C_8$cycloalkylalkyl and $C_3$-$C_8$cycloalkyl, $C_3$-$C_8$fused cycloalkyl and heteroaryl. For example, in some embodiments, the substituents are selected from fluoro, chloro, bromo, cyano, hydroxyl, hydroxylmethyl, methoxy, methoxymethyl, ethyl, isopropyl, trifluoromethyl, aminocarbonyl and cyclopropyl. In some embodiments, $R^1$ has one of the following structures:

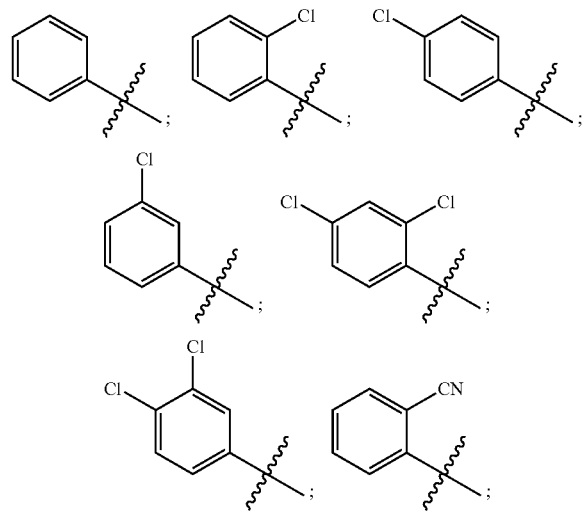

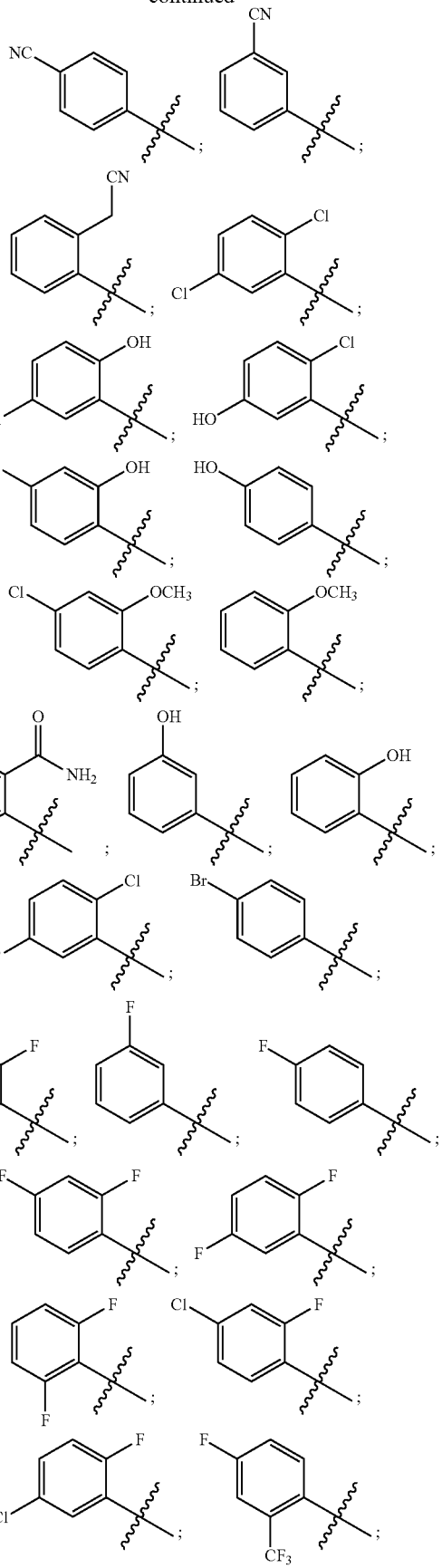

-continued
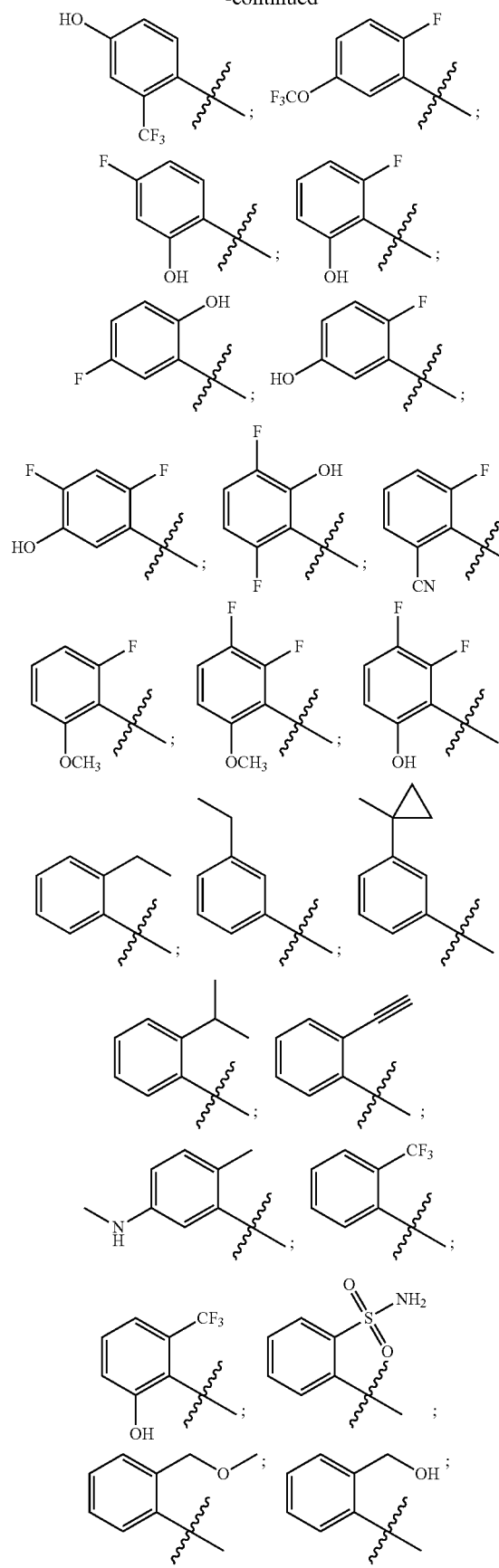
-continued
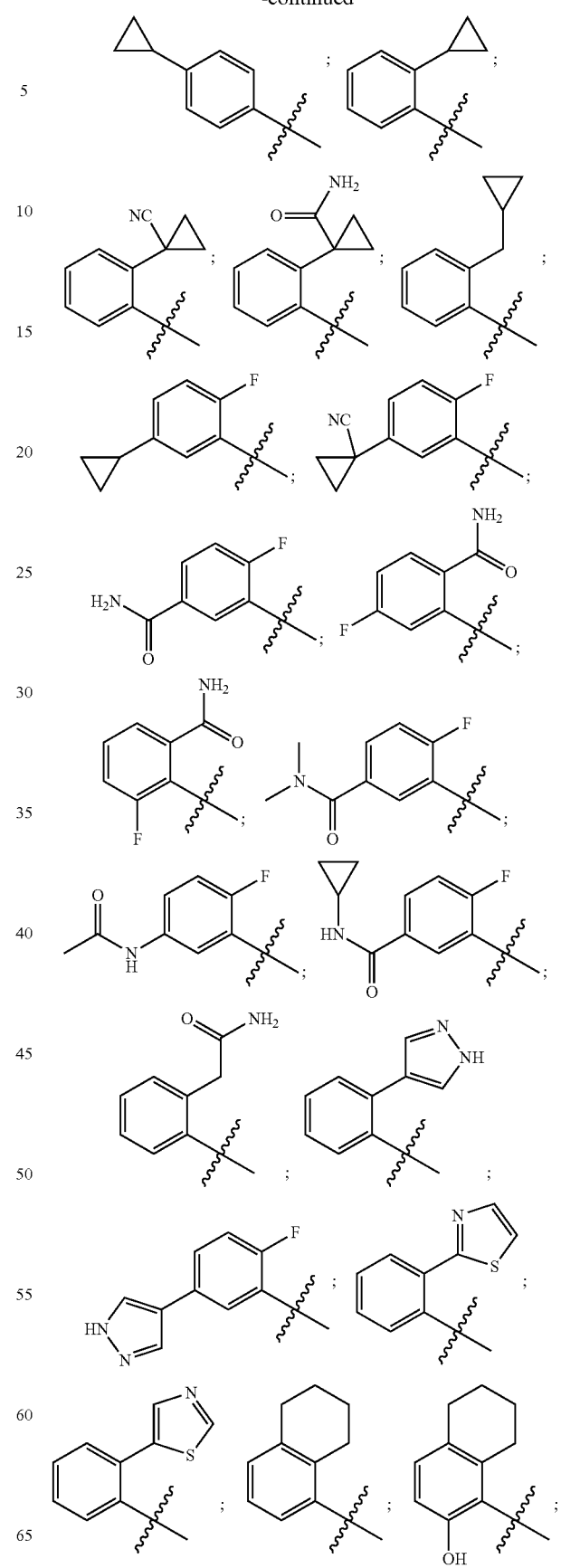

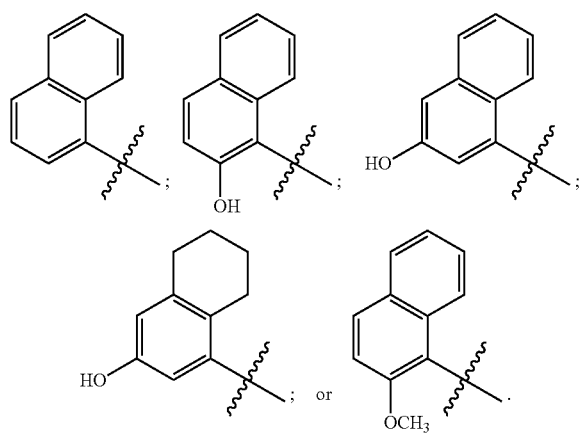

In some embodiments, R¹ is heteroaryl. In some embodiments, R¹ comprises oxygen, sulfur, nitrogen or combinations thereof. For example, in some cases, R¹ is thiophenyl, pyridinyl, pyridinonyl, pyrimidinyl, benzooxazolyl, benzoisoxazolyl, benzodioxazolyl, benzoimidazolyl, quinolinyl, quinolinonyl, dihydroquinolinonyl, tetrahydroquinolinyl, quinazolinyl, indazolyl, indolinonyl, benzothiophenyl, dihydrobenzodioxinyl. In some embodiments, R¹ is unsubstituted. In other embodiments, R¹ is substituted with one or more substituents. In some embodiments, the substituents are selected from halo, $C_1$-$C_6$alkyl, $C_1$-$C_6$alkoxy, or $C_2$-$C_6$alkenylcarbonylaminyl. For example, in some cases, the substituents are selected from fluoro, chloro, amino and methyl. In some embodiments, R¹ has one of the following structures:

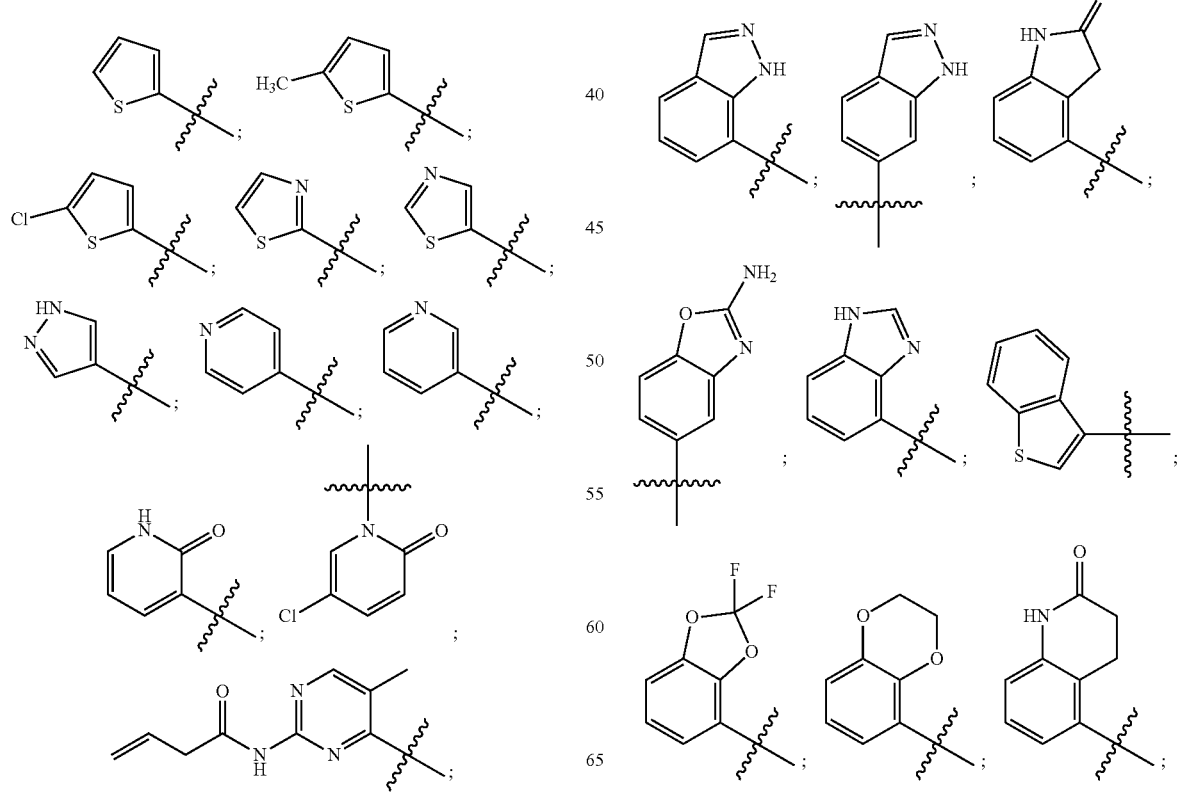

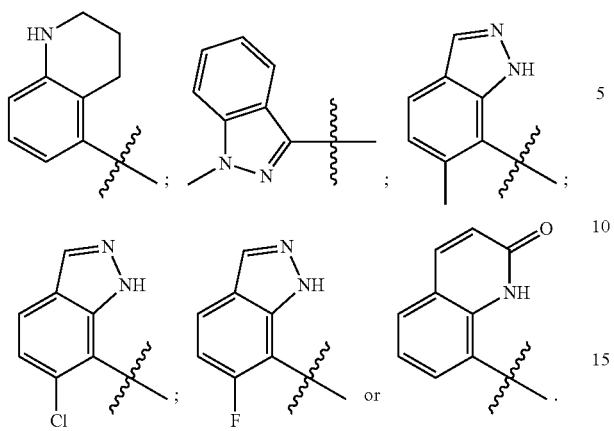

In some embodiments of the compounds disclosed herein, $R^{2a}$, when present, is H. In other embodiments, $R^{2a}$, when present, is halo, for example, chloro or fluoro. In some embodiments, $R^{2a}$, when present, is $C_1$-$C_6$alkyl. In some cases, $R^{2a}$, when present, is $C_3$-$C_8$ cycloalkyl, for example cyclopropyl.

In some embodiments of the compounds disclosed herein $R^{2b}$ and $R^{2c}$, when present, are H. In other embodiments, $R^{2b}$ and $R^{2c}$, when present, are each independently halo. In some cases, $R^{2b}$, when present, is halo. In some cases, $R^{2c}$, when present, is halo. In some embodiments, halo is chloro or fluoro.

In some embodiments of the compounds disclosed herein T is selected from the group consisting of:

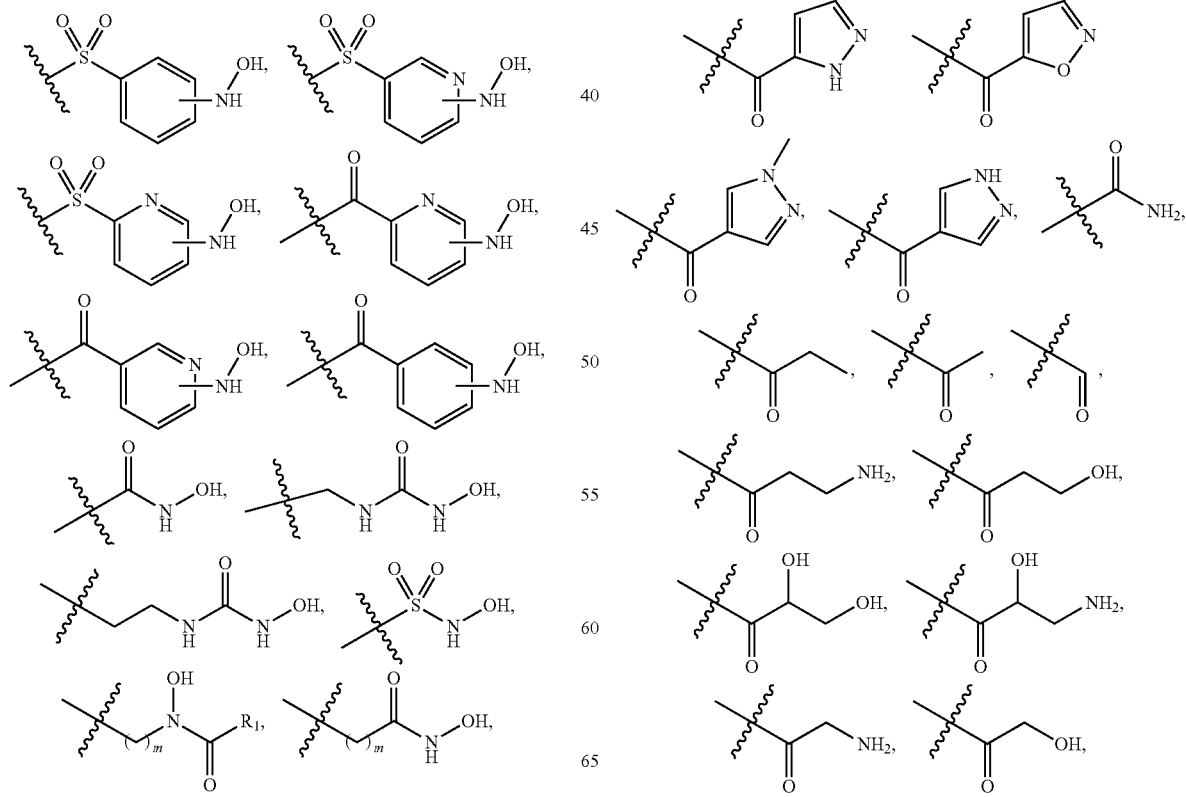

-continued

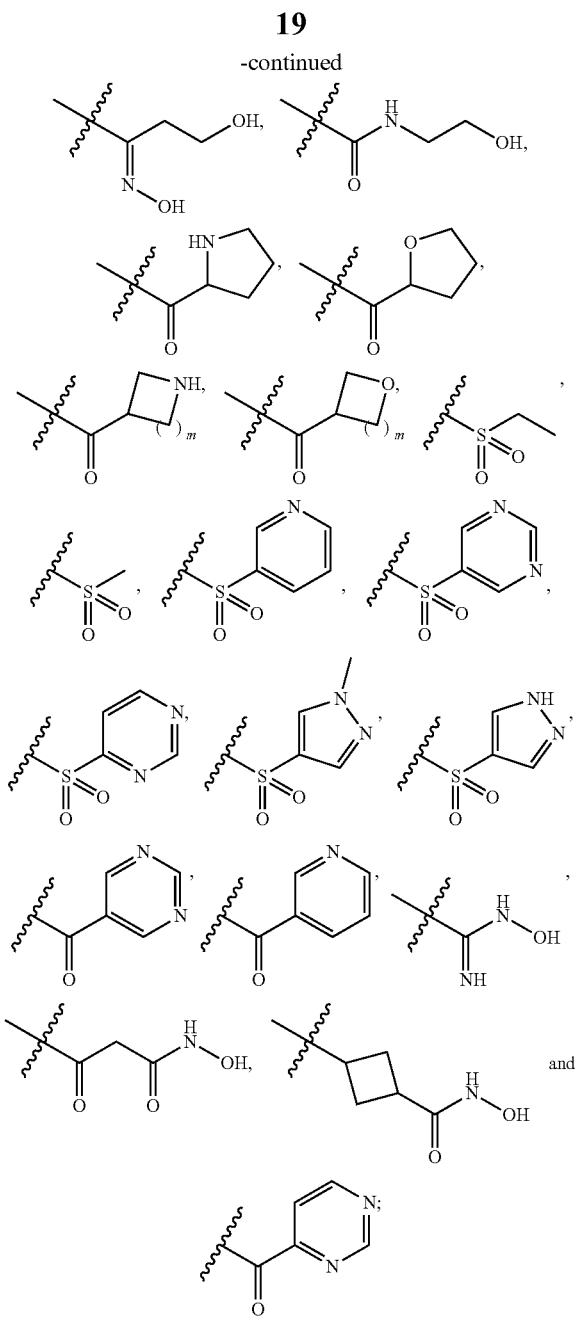

and m, when present, is 0, 1, 2, or 3. In some embodiments, T is selected from the group consisting of:

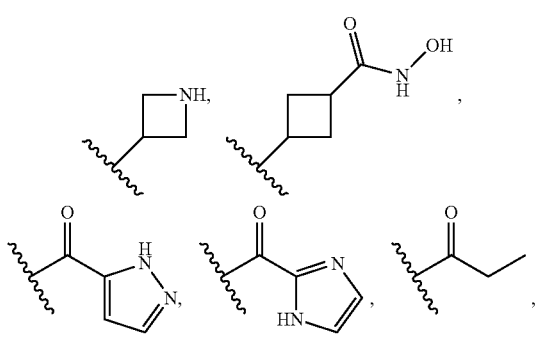

-continued

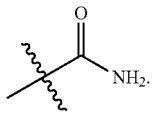

In some embodiments of the compounds disclosed herein $L^1$ is a bond. In other embodiments, $L^1$ is —$NR^7$—, for example, —NH—.

In some embodiments of the compounds disclosed herein $L^2$ is a bond. In other embodiments, $L^2$ is alkylene, for example, —$CH_2$— or —$CH_2CH_2$—.

In some embodiments, $R^{3a}$, $R^{3b}$, $R^{4a}$ and $R^{4b}$ are H.

In some embodiments, $R^{3a}$ or $R^{4a}$ is aminocarbonyl, for example,

In some embodiments, $R^{3a}$ or $R^{4a}$ is cyano.

In some embodiments of the compounds provided herein, Z is N. In some embodiments, X is N. In some embodiments, Y is N. In some cases, Y is $CR^6$, wherein $R^6$ is H and W is $CR^6$, wherein $R^6$ is a bond to $L^1$. In some cases, Y is $CR^6$, wherein $R^6$ is H, W is $CR^6$, wherein $R^6$ is a bond to $L^1$ and X is $CR^6$, wherein $R^6$ is cyano, methoxy or amino. In some cases, X is $CR^6$ and $R^6$ is cyano. In some cases, W is $CR^6$, wherein $R^6$ is a bond to $L^1$ and X is $CR^6$, wherein $R^6$ is H.

In some embodiments of the compounds provided herein, Z is a bond. In some cases, Y is $NR^5$. In some embodiments, $R^5$ is H.

In some embodiments of the compounds provided herein, X or Y is $CR^6$. In some cases, $R^6$ is cyano, methoxy or amino.

In some embodiments, the compound is selected from the group of compounds shown in Table 1. In some embodiments, the compound is selected from a compound in Table 2.

In one aspect, the disclosure provides a pharmaceutical composition comprising a pharmaceutically acceptable carrier and a compound in accordance with an embodiment of the present invention. In some embodiments, the pharmaceutical composition is suitable for oral administration. In some embodiments, the pharmaceutical composition is suitable for injection.

In one aspect, the disclosure provides a method for regulating activity of a K-Ras, H-Ras or N-Ras mutant protein. In one embodiment, the method comprises contacting the K-Ras, H-Ras or N-Ras mutant protein with a compound in accordance with an embodiment of the present invention.

In one aspect, the disclosure provides a method of treating a disorder in a subject in need thereof. In one embodiment, the method comprises (a) determining if the subject has a K-Ras, H-Ras or N-Ras mutation; and (b) if the subject is determined to have the K-Ras, H-Ras or N-Ras mutation then administering to the subject a therapeutically effective dose of a pharmaceutical composition comprising at least one compound in accordance with an embodiment of the present invention or a salt thereof. In some embodiments, the disorder is cancer, such as pancreatic cancer, colon cancer, MYH associated polyposis, colorectal cancer, lung cancer or NSCLC. In some embodiments, the method further comprises administering another anti-cancer agent.

In one aspect, the disclosure provides a method of preparing a labeled K-Ras, H-Ras or N-Ras mutant protein. In one embodiment, the method comprises contacting the K-Ras, H-Ras or N-Ras mutant protein with a compound in accordance with an embodiment of the invention, to result in the labeled K-Ras, H-Ras or N-Ras protein.

In some embodiments of the compounds provided herein, T is capable of forming a complex with a metal ion that is complexed with the Ras protein. In some embodiments, T is capable of forming an interaction with a mutation residue in the Ras protein, for example, G12D.

In some embodiments, provided herein is a compound having the following structure (I):

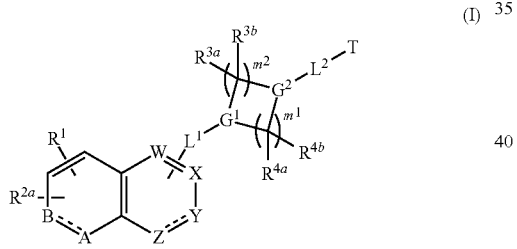
(I)

or a pharmaceutically acceptable salt, tautomer, prodrug or stereoisomer thereof, wherein: A is $CR^1$, $CR^{2b}$, $NR^5$ or S; B is a bond, $CR^1$ or $CR^{2c}$; $G^1$ and $G^2$ are each independently N or CH; W, X and Y are each independently N, $NR^5$ or $CR^6$; Z is a bond, N or $CR^6$; $L^1$ is a bond or $NR^7$; $L^2$ is a bond or alkylene; $R^1$ is H, cyano, halo, heterocyclyl, heteroaryl, aryloxy or aryl; $R^{2a}$, $R^{2b}$ and $R^{2c}$ are each independently H, halo, hydroxyl, $C_1$-$C_6$ alkyl, $C_1$-$C_6$ haloalkyl, $C_3$-$C_8$ cycloalkyl or aryl; $R^{3a}$ and $R^{3b}$ are, at each occurrence, independently H, —OH, —$NH_2$, —$CO_2H$, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl; or $R^{3a}$ and $R^{3b}$ join to form oxo or a carbocyclic or heterocyclic ring; or $R^{3a}$ is H, —OH, —$NH_2$, —$CO_2H$, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl, and $R^{3b}$ joins with $R^{4b}$ to form a carbocyclic or heterocyclic ring; $R^{4a}$ and $R^{4b}$ are, at each occurrence, independently H, —OH, —$NH_2$, —$CO_2H$, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl; or $R^{4a}$ and $R^{4b}$ join to form oxo or a carbocyclic or heterocyclic ring; or $R^{4a}$ is H, —OH, —$NH_2$, —$CO_2H$, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl, and $R^{4b}$ joins with $R^{3b}$ to form a carbocyclic or heterocyclic ring; $R^5$ and $R^7$ are each independently H or $C_1$-$C_6$ alkyl; $R^6$ is, at each occurrence, independently H, oxo, cyano, cyanoalkyl, amino, aminylalkyl, aminylalkylaminyl, aminocarbonyl, alkylaminyl, halo alkylamino, hydroxylalkyamino, amindinylalkyl, amidinylalkoxy, amindinylalkylaminyl, guanidinylalkyl, guanidinylalkoxy, guanidinylalkylaminyl, $C_1$-$C_6$ alkoxy, aminylalkoxy, alkylcarbonylaminylalkoxy, $C_1$-$C_6$ alkyl, heterocyclyl, heterocyclyloxy, heterocyclylalkyloxy, heterocyclylamino, heterocyclylalkylamino, heteroaryl, heteroaryloxy, heteroarylalkyloxy, heteroarylamino, heteroarylalkylamino, aryl, aryloxy, arylamino, arylalkylamino, arylalkyloxy or a bond to $L^1$; $m^1$ and $m^2$ are each independently 1, 2 or 3; ----- indicates a single or double bond such that all valences are satisfied; and T is H or a polar group capable of forming a complex with a Ras protein via an interaction other than one resulting in a covalent bond with the cysteine residue at position 12 of a K-Ras, H-Ras or N-Ras G12C mutant protein; wherein at least one of W, X, Y or Z is $CR^6$ where $R^6$ is a bond to $L^1$; and provided that when $R^1$, $R^{2a}$, $R^{2b}$ and $R^{2c}$ are all independently selected from H and halo, then X and Z are both N and at least one of $R^{3a}$, $R^{3b}$, $R^{4a}$ or $R^{4b}$ is not H, and provided that at least one of $R^{2a}$, $R^{2b}$ or $R^{2c}$ is not H when $R^1$ is pyridyl.

In some embodiments, the compound has one of the following structures (I'j), (I'k), (I'l) or (I'm):

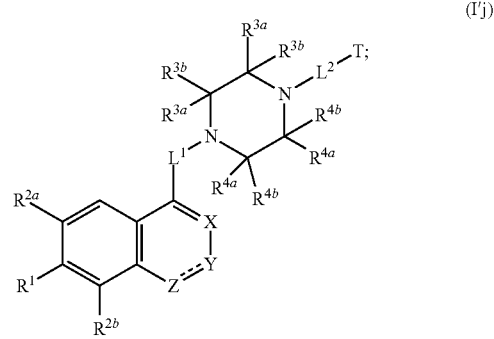
(I'j)

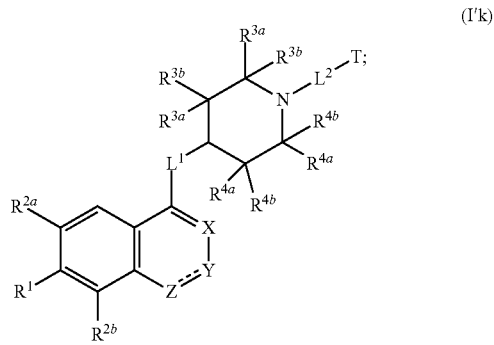
(I'k)

23
-continued

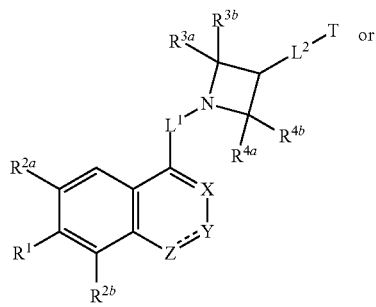
(I'l)

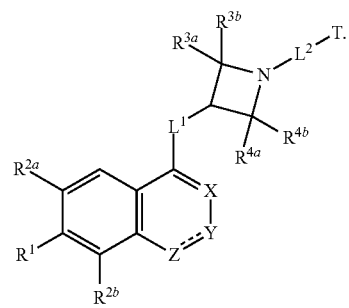
(I'm)

In some embodiments of the compounds provided herein, R¹ is aryl or heteroaryl. In some embodiments, R¹ is substituted with one or more substituents, for example, fluoro, chloro, bromo, cyano, hydroxyl, hydroxylmethyl, methoxy, methoxymethyl, ethyl, isopropyl, trifluoromethyl, aminocarbonyl and cyclopropyl. In some embodiments, T is selected from the group consisting of H, —NH$_2$, —OH, —NHR⁵,

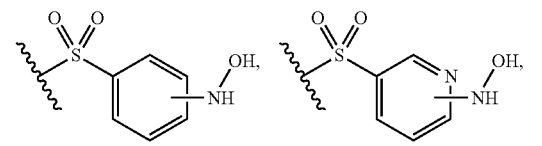

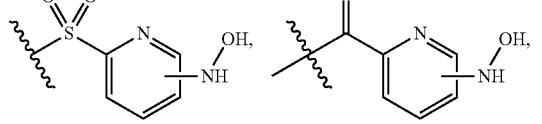

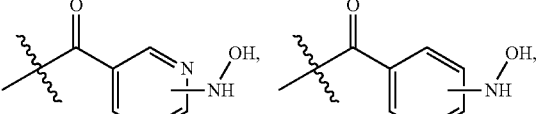

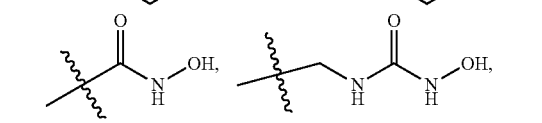

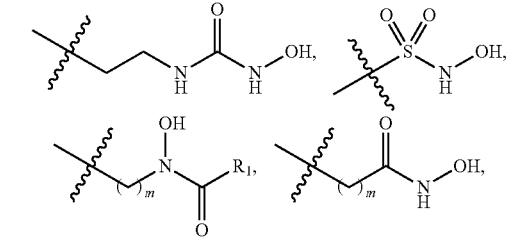

24
-continued

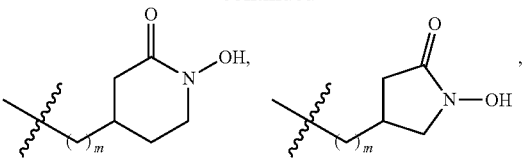

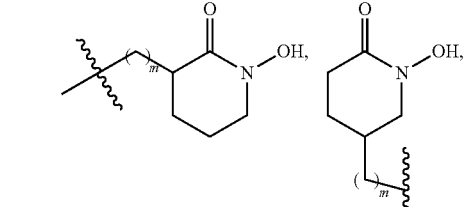

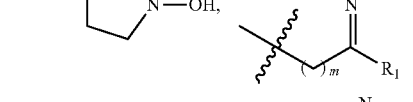

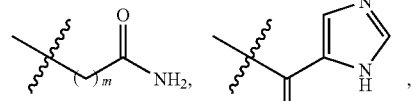

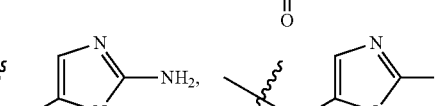

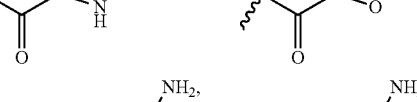

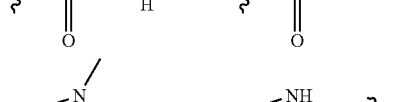

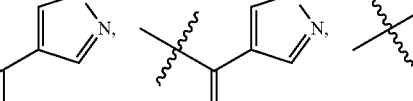

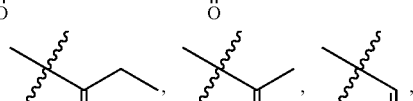

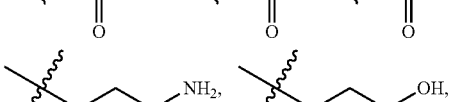

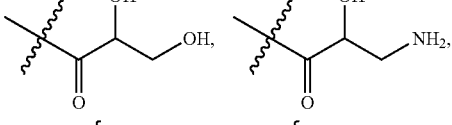

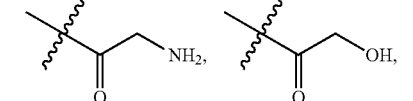

-continued

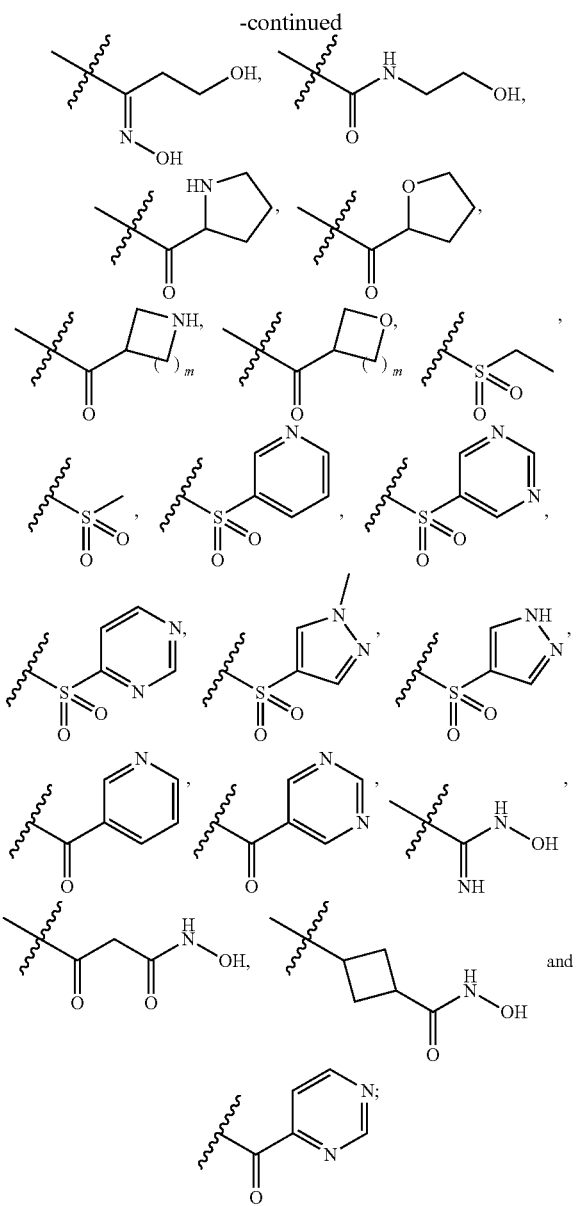

and m, when present, is 0, 1, 2, or 3.

In some embodiments of the compounds provided herein, $L^1$ is a bond. In some embodiments, $L^2$ is a bond. In some embodiments, Z is N. In some embodiments, X is N. In some embodiments, $R^{3a}$ and $R^{3b}$ join to form oxo. In some embodiments, $R^{4a}$ and $R^{4b}$ join to form oxo.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 Shows some common oncogenes, their respective tumor type and cumulative mutation frequencies (all tumors).

DETAILED DESCRIPTION

Figure 1:
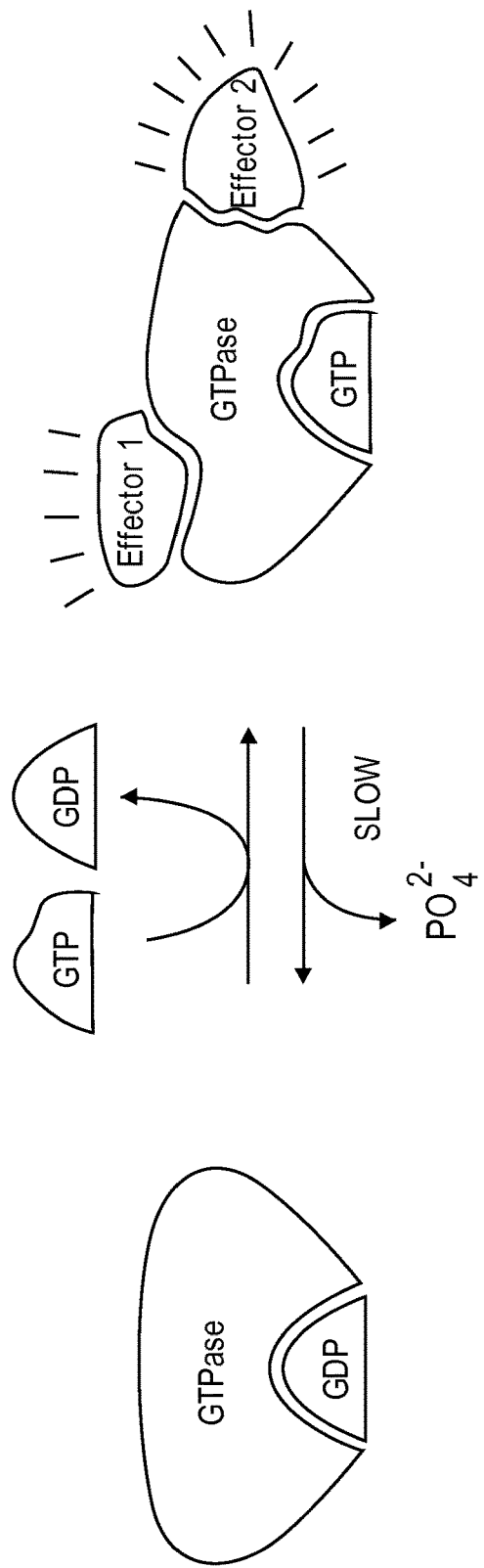
FIG. 1 Shows the enzymatic activity of Ras.
Figure 2:
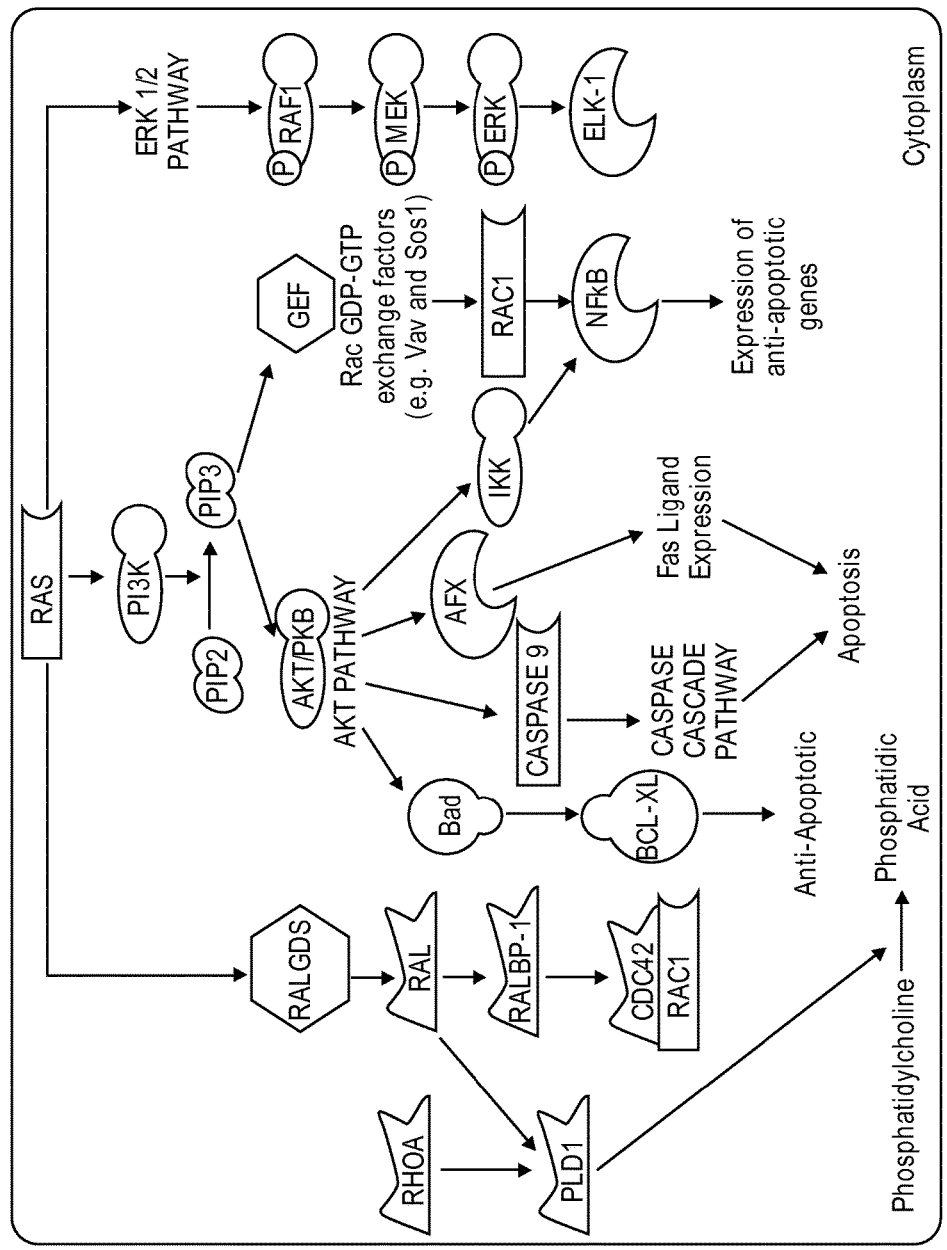
FIG. 2 Shows a signal transduction pathway for Ras.

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" include plural references unless the context clearly dictates otherwise.

"Amino" refers to the —$NH_2$ radical.

"Carboxy" or "carboxyl" refers to the —$CO_2H$ radical.

"Cyano" refers to the —CN radical.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butyryl, pentynyl, hexynyl, and the like. Alkyl includes alkenyls (one or more carbon-carbon double bonds) and alkynyls (one or more carbon-carbon triple bonds). Unless stated otherwise specifically in the specification, an alkyl group is optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain is optionally substituted.

"Alkenylene" is an alkylene, as defined above, which comprises one or more carbon-carbon double bonds. Unless stated otherwise specifically in the specification, an alkenylene is optionally substituted "Alkylenecarbonyl" refers to a radical of the formula —C(=O)$R_a$—, where $R_a$ is an alkylene chain as defined above. Unless stated otherwise specifically in the specification, an alkylenecarbonyl is optionally substituted.

"Alkenylenecarbonyl" refers to an alkylenecarbonyl, as defined above, which comprises one or more carbon-carbon double bonds. Unless stated otherwise specifically in the specification, an alkenylenecarbonyl is optionally substituted.

"Alkoxy" refers to a radical of the formula —OR$_a$ where R$_a$ is an alkyl radical as defined above containing one to twelve carbon atoms. Unless stated otherwise specifically in the specification, an alkoxy group is optionally substituted.

"Alkylamino" refers to a radical of the formula —NHR$_a$ or —NR$_a$R$_a$ where each R$_a$ is, independently, an alkyl radical as defined above containing one to twelve carbon atoms. Unless stated otherwise specifically in the specification, an alkylamino group is optionally substituted.

"Aminoalkyl" refers to an alkyl group comprising at least one amino substituent. The amino substituent can be on a tertiary, secondary or primary carbon. Unless stated otherwise specifically in the specification, an aminoalkyl group is optionally substituted.

"Alkylaminoalkyl" refers to an alkyl group comprising at least one alkylamino substituent. The alkylamino substituent can be on a tertiary, secondary or primary carbon. Unless stated otherwise specifically in the specification, an alkylaminoalkyl group is optionally substituted.

"Aminocarbonyl" refers to a radical of the formula —C(=O)NR$_a$R$_b$, where R$_a$ and R$_b$ are each independently H or alkyl. Unless stated otherwise specifically in the specification, an alkoxy group is optionally substituted.

"Aryl" refers to a hydrocarbon ring system radical comprising hydrogen, 6 to 18 carbon atoms and at least one aromatic ring. For purposes of this invention, the aryl radical is a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Arylene" refers to a divalent aryl group which links the rest of the molecule (e.g., compound of structure I) to a radical group and/or to the rest of the molecule. Unless stated specifically otherwise, an arylene is optionally substituted.

"Aralkyl" refers to a radical of the formula —R$_b$-R$_c$ where R$_b$ is an alkylene chain as defined above and R$_c$ is one or more aryl radicals as defined above, for example, benzyl, diphenylmethyl and the like. Unless stated otherwise specifically in the specification, an aralkyl group is optionally substituted.

"Carboxyalkyl" refers to a radical of the formula —R$_b$-R$_c$ where R$_b$ is an alkylene chain as defined above and R$_c$ is a carboxy group as defined above. Unless stated otherwise specifically in the specification, carboxyalkyl group is optionally substituted.

"Cyanoalkyl" refers to a radical of the formula —R$_b$-R$_c$ where R$_b$ is an alkylene chain as defined above and R$_c$ is a cyano group as defined above. Unless stated otherwise specifically in the specification, a cyanoalkyl group is optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1] heptanyl, and the like. A "cycloalkenyl" is a cycloalkyl comprising one or more carbon-carbon double bonds within the ring. Unless otherwise stated specifically in the specification, a cycloalkyl (or cycloalkenyl) group is optionally substituted.

The term "bicycloalkyl" refers to a structure consisting of two cycloalkyl moieties, unsubstituted or substituted, that have two or more atoms in common. If the cycloalkyl moieties have exactly two atoms in common they are said to be "fused". Examples include, but are not limited to, bicyclo [3.1.0]hexyl, perhydronaphthyl, and the like. If the cycloalkyl moieties have more than two atoms in common they are said to be "bridged". Examples include, but are not limited to, bicyclo[3.2.1]heptyl ("norbornyl"), bicyclo [2.2.2]octyl, and the like.

As used herein, the term "heteroatom" or "ring heteroatom" is meant to include oxygen (O), nitrogen (N), sulfur (S), and phosphorus (P).

The term "heteroalkyl," by itself or in combination with another term, means, unless otherwise stated, a straight or branched chain, or cyclic hydrocarbon radical, or combinations thereof, comprising of at least one carbon atoms and at least one heteroatom selected from the group comprising of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. The alkyl portion of the moiety is unsubstituted or substituted.

"Heteroalkylene" refers to an alkylene group comprising at least one heteroatom (e.g., N, O or S). In some embodiments, the heteroatom is within the alkylene chain (i.e., the heteroalkylene comprises at least one carbon-heteroatom-carbon bond. In other embodiments, the heteroatom is at a terminus of the alkylene and thus serves to join the alkylene to the remainder of the molecule (e.g., M1-H-A-M2, where M1 and M2 are portions of the a molecule, H is a heteroatom and A is an alkylene). Unless stated otherwise specifically in the specification, a heteroalkylene is optionally substituted.

"Heteroalkylenecarbonyl" refers to a radical of the formula —C(=O)R$_a$—, where R$_a$ is a heteroalkylene chain as defined above. Unless stated otherwise specifically in the specification, a heteroalkylenecarbonyl is optionally substituted.

The term "heterobicycloalkyl" refers to a bicycloalkyl structure, which is unsubstituted or substituted, in which at least one carbon atom is replaced with a heteroatom independently selected from oxygen, nitrogen, and sulfur.

The term "spiroalkyl" refers to a structure, which is unsubstituted or substituted, which comprises at least two cycloalkyl units joined at single carbon. In various embodiments the spiroalkyl rings can be 1-18 carbons.

The term "heterospiroalkyl" refers to a spiroalkyl structure, which is unsubstituted or substituted, in which at least one carbon atom is replaced with a heteroatom independently selected from oxygen, nitrogen, and sulfur.

"Cycloalkylalkyl" refers to a radical of the formula —R$_b$R$_d$ where R$_b$ is an alkylene chain as defined above and R$_d$ is a cycloalkyl radical as defined above. Unless stated otherwise specifically in the specification, a cycloalkylalkyl group is optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring is replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group is optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical is a monocyclic, bicyclic, tricyclic or tetracyclic ring system, which may include fused or bridged ring systems; and the nitrogen, carbon or sulfur atoms in the heterocyclyl radical is optionally oxidized; the nitrogen atom is optionally quaternized; and the heterocyclyl radical is partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification. Unless stated otherwise specifically in the specification, a heterocyclyl group is optionally substituted.

"Heterocycloalkylene" refers to a divalent saturated heterocyclyl group which links the rest of the molecule (e.g., compound of structure I) to a radical group and/or to the rest of the molecule. Unless stated specifically otherwise, a heterocycloalkylene is optionally substituted.

"Heterocycloalkylenecarbonyl" refers to a radical of the formula —R$_a$C(=O)—, wherein R$_a$ is a heterocycloalkylene as defined above. Unless stated specifically otherwise, a heterocycloalkylenecarbonyl is optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group is optionally substituted.

"Heterocyclylalkyl" or "heterocycloalkyl" refers to a radical of the formula —R$_b$R$_e$ where R$_b$ is an alkylene chain as defined above and R$_e$ is a heterocyclyl radical as defined above, and if the heterocyclyl is a nitrogen-containing heterocyclyl, the heterocyclyl is optionally attached to the alkyl radical at the nitrogen atom. Unless stated otherwise specifically in the specification, a heterocyclylalkyl group is optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group is optionally substituted.

"Heteroarylene" refers to a divalent saturated heteroaryl group which links the rest of the molecule (e.g., compound of structure I) to a radical group and/or to the rest of the molecule. Unless stated specifically otherwise, a heteroarylene is optionally substituted.

"Heteroarylenecarbonyl" refers to a radical of the formula —R$_a$C(=O)—, wherein R$_a$ is a heteroarylene as defined above. Unless stated specifically otherwise, a heteroarylenecarbonyl is optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group is optionally substituted.

"Heteroarylalkyl" refers to a radical of the formula —R$_b$R$_f$ where R$_b$ is an alkylene chain as defined above and R$_f$ is a heteroaryl radical as defined above. Unless stated otherwise specifically in the specification, a heteroarylalkyl group is optionally substituted.

"Hydroxylalkyl" refers to an alkyl group comprising at least one hydroxyl substituent. The —OH substituent may be on a primary, secondary or tertiary carbon. Unless stated otherwise specifically in the specification, a hydroxylalkyl group is optionally substituted.

"Thioalkyl" refers to a radical of the formula —SR$_a$ where R$_a$ is an alkyl radical as defined above containing one to twelve carbon atoms. Unless stated otherwise specifically in the specification, a thioalkyl group is optionally substituted.

The term "substituted" used herein means any of the above groups (e.g., alkyl, alkylene, alkenylene, alkenylenecarbonyl, alkoxy, alkylamino, aminoalkyl, alkylaminoalkyl, thioalkyl, aryl, arylene, aralkyl, carboxyalkyl, cyanoalkyl, cycloalkyl, cycloalkylalkyl, heteroalkyl, heteroalkylene, heteroalkylenecarbonyl, heterobicycloalkyl, spiroalkyl, heterospiroalkyl, haloalkyl, heterocyclyl, heterocycloalkylene, heterocycloalkylenecarbonyl, N-heterocyclyl, heterocyclylalkyl, heteroaryl, heteroarylene, heteroarylenecarbonyl, N-heteroaryl, hydroxylalkyl, thioalkyl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$.

"Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents is optionally substituted with one or more of the above substituents.

"Electrophile" or "electrophilic moiety" is any moiety capable of reacting with a nucleophile (e.g., a moiety having a lone pair of electrons, a negative charge, a partial negative charge and/or an excess of electrons, for example a —SH group). Electrophiles typically are electron poor or comprise atoms which are electron poor. In certain embodiments an electrophile contains a positive charge or partial positive charge, has a resonance structure which contains a positive charge or partial positive charge or is a moiety in which delocalization or polarization of electrons results in one or more atom which contains a positive charge or partial positive charge. In some embodiments, the electrophiles comprise conjugated double bonds, for example an α,β-unsaturated carbonyl or α,β-unsaturated thiocarbonyl compound.

A "polar group" refers to a moiety with one or more dipoles as a result of opposing charges from one or more polar bonds arranged asymmetrically. A polar bond is any bond between non-identical atoms. A polar group can be a group that is more hydrophilic than an alkyl group. In some embodiments, a polar group is a metal chelator or a metal chelator moiety. In some embodiments, a polar group comprises at least one heteroatom selected from S, O, and N. For example, a polar group can be an alkyl group that is substituted with one or more functional groups comprising a heteroatom. For example, a polar group can be an alkyl group substituted with one or more alcohol, ether, amine, hydroxyamine, aldehyde, ketone, ester, carboxylic acid, thiol, thioether, thiocarbonyl, sulfonate, sulfunite, phosphonate ester, amide, heterocycle and/or oxime.

The term "metal chelator" or "metal chelator moiety" is any moiety capable of forming two or more separate coordinate bonds between the metal chelator group and a single central metal atom or metal ion. Metal chelators typically have at least one pair of unbonded electrons which can bind to a metal atom or metal ion. In certain embodiments, a metal chelator moiety comprises at least two heteroatoms selected from S, O, and N. In some embodiments, the metal chelator moiety is a bidentate or tridentate functional group. In some embodiments, a metal chelator moiety comprises a bidentate functional group selected from the group consisting of hydroxyamine, hydroxyamide, sulfonamide, urea, amide and oxime. In some embodiments, a metal chelator moiety comprises two or more monodentate functional groups selected from the group consisting of hydroxy, amino, ether, aldehyde, ketone, amide, thiol, thioether, heterocycle (e.g. imidazole) or oxime.

The term "forming a complex" refers to two or more moieties having interactions that can occur through a direct association, an indirect association, or a combination thereof. Direct association includes, for example, covalent bonds, noncovalent bonds, Lewis acid/base interactions, hydrogen bonding, or a ligand interaction with a metal atom or ion. Indirect association includes, for example, bridging, association through an amino acid of a protein, or association through one or more molecules of a solvent, for example water.

The term "effective amount" or "therapeutically effective amount" refers to that amount of a compound described herein that is sufficient to effect the intended application including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refer to an approach for obtaining beneficial or desired results with respect to a disease, disorder or medical condition including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The terms "antagonist" and "inhibitor" are used interchangeably, and they refer to a compound having the ability to inhibit a biological function of a target protein, whether by inhibiting the activity or expression of the protein, such as K-Ras, H-Ras or N-Ras G12C. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

As used herein, "agent" or "biologically active agent" refers to a biological, pharmaceutical, or chemical compound or other moiety. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "selective inhibition" or "selectively inhibit" refers to a biologically active agent refers to the agent's ability to preferentially reduce the target signaling activity as compared to off-target signaling activity, via direct or indirect interaction with the target.

"Subject" refers to an animal, such as a mammal, for example a human. The methods described herein can be useful in both human therapeutics and veterinary applications. In some embodiments, the subject is a mammal, and in some embodiments, the subject is human.

"Mammal" includes humans and both domestic animals such as laboratory animals and household pets (e.g., cats, dogs, swine, cattle, sheep, goats, horses, rabbits), and non-domestic animals such as wildlife and the like.

"Radiation therapy" means exposing a subject, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including without limitation x-rays, gamma rays, and neutrons.

"Prodrug" is meant to indicate a compound that may be converted under physiological conditions or by solvolysis to a biologically active compound described herein (e.g., compound of structure (I)). Thus, the term "prodrug" refers to a precursor of a biologically active compound that is pharmaceutically acceptable. In some aspects, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "in vivo" refers to an event that takes place in a subject's body.

The invention disclosed herein is also meant to encompass all pharmaceutically acceptable compounds of structure (I) being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action, or binding affinity to pharmacologically important site of action. Certain isotopically-labeled compounds of structure (I), for example, those incorporating a radioactive isotope, are useful in drug and/or substrate tissue distribution studies.

The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence are preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

Often crystallizations produce a solvate of the compound of the invention. As used herein, the term "solvate" refers to an aggregate that comprises one or more molecules of a compound of the invention with one or more molecules of solvent. In some embodiments, the solvent wise water, in which case the solvate is a hydrate. Alternatively, in other embodiments, the solvent is an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. In some aspects, the compound of the invention is a true solvate, while in other cases, the compound of the invention merely retains adventitious water or is a mixture of water plus some adventitious solvent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The compounds of the invention, or their pharmaceutically acceptable salts may contain one or more asymmetric centers and may thus give rise to enantiomers, diastereomers, and other stereoisomeric forms that are defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

The present invention includes all manner of rotamers and conformationally restricted states of a compound of the invention.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The chemical naming protocol and structure diagrams used herein are a modified form of the I.U.P.A.C. nomenclature system, using the ACD/Name Version 9.07 software program and/or ChemDraw Ultra Version 11.0.1 software naming program (CambridgeSoft). For complex chemical names employed herein, a substituent group is typically named before the group to which it attaches. For example, cyclopropylethyl comprises an ethyl backbone with a cyclopropyl substituent. Except as described below, all bonds are identified in the chemical structure diagrams herein, except for all bonds on some carbon atoms, which are assumed to be bonded to sufficient hydrogen atoms to complete the valency.

Compounds

In an aspect, the invention provides compounds which are capable of selectively binding to and/or modulating a Ras protein. In some embodiments, the Ras protein includes but is not limited to a mutant K-Ras, H-Ras or N-Ras protein. In some embodiments, the compounds modulate the Ras protein by binding to or interacting with one or more amino acids and/or one or more metal ion. Some subject compounds may also perturb the switch I conformation. The binding of these compounds may disrupt Ras (non-limiting examples include, K-Ras, H-Ras or N-Ras) downstream signaling.

In some embodiments, provided herein is a compound having the structure (I):

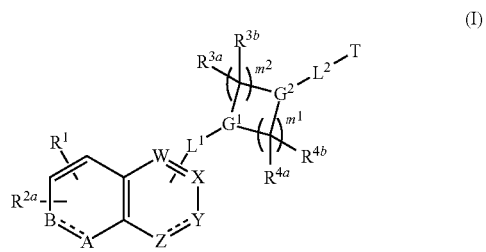

or a pharmaceutically acceptable salt, tautomer, prodrug or stereoisomer thereof, wherein:

A is $CR^1$, $CR^{2b}$, $NR^5$ or S;

B is a bond, $CR^1$ or $CR^{2c}$;

$G^1$ and $G^2$ are each independently N or CH;

W, X and Y are each independently N, $NR^5$ or $CR^6$;

Z is a bond, N or $CR^6$;

$L^1$ is a bond or $NR^7$;

$L^2$ is a bond or alkylene;

$R^1$ is H, cyano, halo, $C_1$-$C_6$alkyl, $C_1$-$C_6$alkylamino, $C_3$-$C_8$ cycloalkyl, $C_1$-$C_6$alkenyl or $C_3$-$C_8$cycloalkenyl, heterocyclyl, heteroaryl, aryloxy or aryl;

$R^{2a}$, $R^{2b}$ and $R^{2c}$ are each independently H, halo, hydroxyl, $C_1$-$C_6$ alkyl, $C_1$-$C_6$ haloalkyl $C_3$-$C_8$ cycloalkyl or aryl;

$R^{3a}$ and $R^{3b}$ are, at each occurrence, independently H, —OH, —$NH_2$, —$CO_2H$, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl; or $R^{3a}$ and $R^{3b}$ join to form a carbocyclic or heterocyclic ring; or $R^{3a}$ is H, —OH, —$NH_2$, —$CO_2H$, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl, and $R^{3b}$ joins with $R^{4b}$ to form a carbocyclic or heterocyclic ring;

$R^{4a}$ and $R^{4b}$ are, at each occurrence, independently H, —OH, —$NH_2$, —$CO_2H$, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl; or $R^{4a}$ and $R^{4b}$ join to form a carbocyclic or heterocyclic ring; or $R^{4a}$ is H, —OH, —$NH_2$, —$CO_2H$, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl, and $R^{4b}$ joins with $R^{3b}$ to form a carbocyclic or heterocyclic ring;

$R^5$ and $R^7$ are each independently H or $C_1$-$C_6$ alkyl;

$R^6$ is, at each occurrence, independently H, oxo, cyano, cyanoalkyl, amino, aminylalkyl, aminylalkylaminyl, aminocarbonyl, alkylaminyl, halo alkyl amino, hydroxylalkyamino, amindinylalkyl, amidinylalkoxy, amindinylalkylaminyl, guanidinylalkyl, guanidinylalkoxy, guanidinylalkylaminyl, $C_1$-$C_6$ alkoxy, aminylalkoxy, alkylcarbonylaminylalkoxy, $C_1$-$C_6$ alkyl, heterocyclyl, heterocyclyloxy, heterocyclylalkyloxy, heterocyclylamino, heterocyclylalkylamino, heteroaryl, heteroaryloxy, heteroarylalkyloxy, heteroarylamino, heteroarylalkylamino, aryl, aryloxy, arylamino, arylalkylamino, arylalkyloxy or a bond to $L^1$;

$m^1$ and $m^2$ are each independently 1, 2 or 3;

---- indicates a single or double bond such that all valences are satisfied; and T is a polar group capable of forming a complex with a Ras protein via an interaction other than one resulting in a covalent bond with the cysteine residue at position 12 of a K-Ras, H-Ras or N-Ras G12C mutant protein;

wherein at least one of W, X, Y or Z is $CR^6$ where $R^6$ is a bond to $L^1$, and provided that when $R^1$, $R^{2a}$, $R^{2b}$ and $R^{2c}$ are all independently selected from H and halo, then X and Z are both N and at least one of $R^{3a}$, $R^{3b}$, $R^{4a}$ or $R^{4b}$ is not H, and provided that at least one of $R^{2a}$, $R^{2b}$ or $R^{2c}$ is not H when $R^1$ is pyridyl.

In some embodiments, provided herein is a compound having the structure (I):

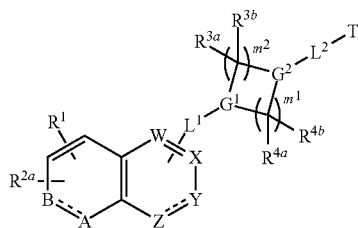

(I)

or a pharmaceutically acceptable salt, tautomer, prodrug or stereoisomer thereof, wherein:

A is $CR^1$, $CR^{2b}$, $NR^5$ or S;

B is a bond, $CR^1$ or $CR^{2c}$;

$G^1$ and $G^2$ are each independently N or CH;

W, X and Y are each independently N, $NR^5$ or $CR^6$;

Z is a bond, N or $CR^6$;

$L^1$ is a bond or $NR^7$;

$L^2$ is a bond or alkylene;

$R^1$ is H, cyano, halo, $C_1$-$C_6$alkyl, $C_1$-$C_6$alkylamino, $C_3$-$C_8$ cycloalkyl, $C_1$-$C_6$alkenyl or $C_3$-$C_8$cycloalkenyl, heterocyclyl, heteroaryl, aryloxy or aryl;

$R^{2a}$, $R^{2b}$ and $R^{2c}$ are each independently H, halo, hydroxyl, $C_1$-$C_6$ alkyl, $C_1$-$C_6$ haloalkyl $C_3$-$C_8$ cycloalkyl or aryl;

$R^{3a}$ and $R^{3b}$ are, at each occurrence, independently H, —OH, —$NH_2$, —$CO_2H$, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl; or $R^{3a}$ and $R^{3b}$ join to form oxo or a carbocyclic or heterocyclic ring; or $R^{3a}$ is H, —OH, —$NH_2$, —$CO_2H$, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl, and $R^{3b}$ joins with $R^{4b}$ to form a carbocyclic or heterocyclic ring;

$R^{4a}$ and $R^{4b}$ are, at each occurrence, independently H, —OH, —$NH_2$, —$CO_2H$, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl; or $R^{4a}$ and $R^{4b}$ join to form oxo or a carbocyclic or heterocyclic ring; or $R^{4a}$ is H, —OH, —$NH_2$, —$CO_2H$, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl, and $R^{4b}$ joins with $R^{3b}$ to form a carbocyclic or heterocyclic ring;

$R^5$ and $R^7$ are each independently H or $C_1$-$C_6$alkyl;

$R^6$ is, at each occurrence, independently H, oxo, cyano, cyanoalkyl, amino, aminylalkyl, aminylalkylaminyl, aminocarbonyl, alkylaminyl, halo alkyl amino, hydroxylalkyamino, amindinylalkyl, amidinylalkoxy, amindinylalkylaminyl, guanidinylalkyl, guanidinylalkoxy, guanidinylalkylaminyl, $C_1$-$C_6$ alkoxy, aminylalkoxy, alkylcarbonylaminylalkoxy, $C_1$-$C_6$ alkyl, heterocyclyl, heterocyclyloxy, heterocyclylalkyloxy, heterocyclylamino, heterocyclylalkylamino, heteroaryl, heteroaryloxy, heteroarylalkyloxy, heteroarylamino, heteroarylalkylamino, aryl, aryloxy, arylamino, arylalkylamino, arylalkyloxy or a bond to $L^1$;

$m^1$ and $m^2$ are each independently 1, 2 or 3;

---- indicates a single or double bond such that all valences are satisfied; and T is H or a polar group capable of forming a complex with a Ras protein via an interaction other than one resulting in a covalent bond with the cysteine residue at position 12 of a K-Ras, H-Ras or N-Ras G12C mutant protein;

wherein at least one of W, X, Y or Z is $CR^6$ where $R^6$ is a bond to $L^1$, and provided that when $R^1$, $R^{2a}$, $R^{2b}$ and $R^{2c}$ are all independently selected from H and halo, then X and Z are both N and at least one of $R^{3a}$, $R^{3b}$, $R^{4a}$ or $R^{4b}$ is not H, and provided that at least one of $R^{2a}$, $R^{2b}$ or $R^{2c}$ is not H when $R^1$ is pyridyl.

In some other embodiments of the foregoing compound of structure (I):

A is $CR^{2b}$, $NR^5$ or S;

B is a bond or $CR^{2c}$;

$G^1$ and $G^2$ are each independently N or CH;

W, X and Y are each independently N, $NR^5$ or $CR^6$;

Z is a bond, N or $CR^6$;

$L^1$ is a bond or $NR^7$;

$L^2$ is a bond or alkylene;

$R^1$ is cyano, $C_1$-$C_6$alkyl, $C_1$-$C_6$alkylamino, $C_3$-$C_8$ cycloalkyl, $C_1$-$C_6$alkenyl or $C_3$-$C_8$ cycloalkenyl, heterocyclyl or aryl;

$R^{2a}$, $R^{2b}$ and $R^{2c}$ are each independently H, halo, $C_1$-$C_6$alkyl or $C_3$-$C_8$ cycloalkyl;

$R^{3a}$ and $R^{3b}$ are, at each occurrence, independently H, —OH, —$NH_2$, —$CO_2H$, halo, cyano, hydroxylalkyl, aminoalkyl, cyanoalkyl, carboxyalkyl or aminocarbonyl; or $R^{3a}$ and $R^{3b}$ join to form a carbocyclic or heterocyclic ring; or R is H, —OH, —$NH_2$, —$CO_2H$, halo, cyano, hydroxylalkyl, aminoalkyl, cyanoalkyl, carboxyalkyl or aminocarbonyl, and $R^{3b}$ joins with $R^{4b}$ to form a carbocyclic or heterocyclic ring;

$R^{4a}$ and $R^{4b}$ are, at each occurrence, independently H, —OH, —$NH_2$, —$CO_2H$, halo, cyano, hydroxylalkyl, aminoalkyl, cyanoalkyl, carboxyalkyl or aminocarbonyl; or $R^{4a}$ and $R^{4b}$ join to form a carbocyclic or heterocyclic ring; or $R^{4a}$ is H, —OH, —$NH_2$, —$CO_2H$, halo, cyano, hydroxylalkyl, aminoalkyl, cyanoalkyl, carboxyalkyl or aminocarbonyl, and $R^{4b}$ joins with $R^{3b}$ to form a carbocyclic or heterocyclic ring;

$R^5$ and $R^7$ are each independently H or $C_1$-$C_6$alkyl;

$R^6$ is, at each occurrence, independently H, oxo, cyano, cyanoalkyl, amino, aminylalkyl, aminylalkylaminyl, aminocarbonyl, alkylaminyl, halo alkyl amino, hydroxylalkyamino, amindinylalkyl, amidinylalkoxy, amindinylalkylaminyl, guanidinylalkyl, guanidinylalkoxy, guanidinylalkylaminyl, $C_1$-$C_6$ alkoxy, aminylalkoxy, alkylcarbonylaminylalkoxy, $C_1$-$C_6$ alkyl, heterocyclyl, heterocyclyloxy, heterocyclylalkyloxy, heterocyclylamino, heterocyclylalkylamino, heteroaryl, heteroaryloxy, heteroarylalkyloxy, heteroarylamino, heteroarylalkylamino, aryl, aryloxy, arylamino, arylalkylamino, arylalkyloxy or a bond to $L^1$;

$m^1$ and $m^2$ are each independently 1, 2 or 3;

---- indicates a single or double bond such that all valences are satisfied; and T is a polar group capable of forming a complex with a Ras protein via an interaction other than one resulting in a covalent bond with the cysteine residue at position 12 of a K-Ras, H-Ras or N-Ras G12C mutant protein, wherein at least one of W, X or Y is $CR^6$ where $R^6$ is a bond to $L^1$.

In still other embodiments of the foregoing compound of structure (I), $R^1$ is H, cyano, halo, heterocyclyl, heteroaryl, aryloxy or aryl.

In certain embodiments of the foregoing, T is not E, and E has the following structure:

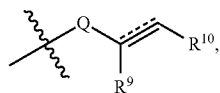

wherein:

---- represents a double or triple bond; Q is —C(=O)—, —$NR^8$C(=O)—, —S(=O)$_2$— or —$NR^8$S(=O)$_2$—;

$R^8$ is H, $C_1$-$C_6$alkyl or hydroxylalkyl; and when === is a double bond then $R^9$ and $R^{10}$ are each independently H, cyano, carboxyl, $C_1$-$C_6$alkyl, alkoxycarbonyl, aminoalkyl, alkylaminoalkyl, or hydroxylalkyl or $R^9$ and $R^{10}$ join to form a carbocyclic or heterocyclic ring; when === is a triple bond; then $R^9$ is absent and $R^{10}$ is H, $C_1$-$C_6$alkyl, aminoalkyl, alkylaminoalkyl or hydroxylalkyl. In certain embodiments when === is a double bond then $R^9$ and $R^{10}$ are each independently H, cyano, $C_1$-$C_6$alkyl, aminoalkyl, alkylaminoalkyl, or hydroxylalkyl or $R^9$ and $R^{10}$ join to form a carbocyclic or heterocyclic ring.

In some embodiments, T is a polar group capable of forming a complex with a Ras protein via an interaction other than one resulting in a covalent bond with the cysteine residue at position 12 of a K-Ras, H-Ras or N-Ras G12C mutant protein. The T group can form a direct or indirect (i.e. through one or more water molecules) complex with a Ras protein. In some embodiments, T is a polar group capable of forming a bond with a metal ion, wherein the metal ion is complexed to a Ras protein. In some embodiments, T is a metal chelating moiety. In some embodiments, T is a polar group capable of directly or indirectly (e.g. through water) forming one or more interactions with a beta-phosphate of nucleotide (GDP) or G12D residue of a Ras protein. In some embodiments, the Ras protein is a K-Ras, H-Ras or N-Ras wild-type protein. In other embodiments, the Ras protein is a K-Ras, H-Ras or N-Ras mutant protein. In some embodiments, the Ras protein is a K-Ras, H-Ras or N-Ras G12C mutant protein.

In some embodiments, T has a molecular weight less than 400, 350, 300, 250, 200, 190, 180, 170, 160, 150, 140, 130, 120, 110, 100, 90, 80, 70, 60, or 50 Daltons. For example, in some embodiments, T has a molecular weight less than 200 daltons. In some embodiments, T has a molecular weight of greater than 40, 50, 60, 70, 80, 90, 100, or 110 Daltons. For example, in some embodiment, T has a molecular weight of greater than 50 Daltons. In some embodiments, T has a molecular weight between about 50 and 300, 50 and 250, 50 and 200, 50 and 150, or 50 and 100 Daltons.

In some embodiments, T is an optionally substituted alkyl group comprising at least 1, 2, 3, 4, 5, 6, 7, 8, or 9 heteroatoms selected from N, O, and S. In some embodiments, T is an optionally substituted alkyl group comprising at least 1, 2, 3, 4, or 5 nitrogen atoms. In some embodiments, T is an optionally substituted alkyl group comprising at least 1, 2, 3, 4, or 5 oxygen atoms. In some embodiments, T is an optionally substituted alkyl group comprising at least 1, 2, 3, 4, or 5 sulfur atoms. In some embodiments, T is an optionally substituted alkyl group comprising at least 1, 2, 3, 4, 5, 6, 7, 8, or 9 heteroatoms selected from N, O, and S, wherein T has a molecular weight between 50 and 300 Daltons, and wherein T does not comprise an electrophilic group capable of forming a covalent bond with a cysteine. In some embodiments, T does not comprise a Michael acceptor. In some embodiments, T does not comprise an alpha-beta unsaturated carbonyl group.

In some cases, T is selected from the group consisting of

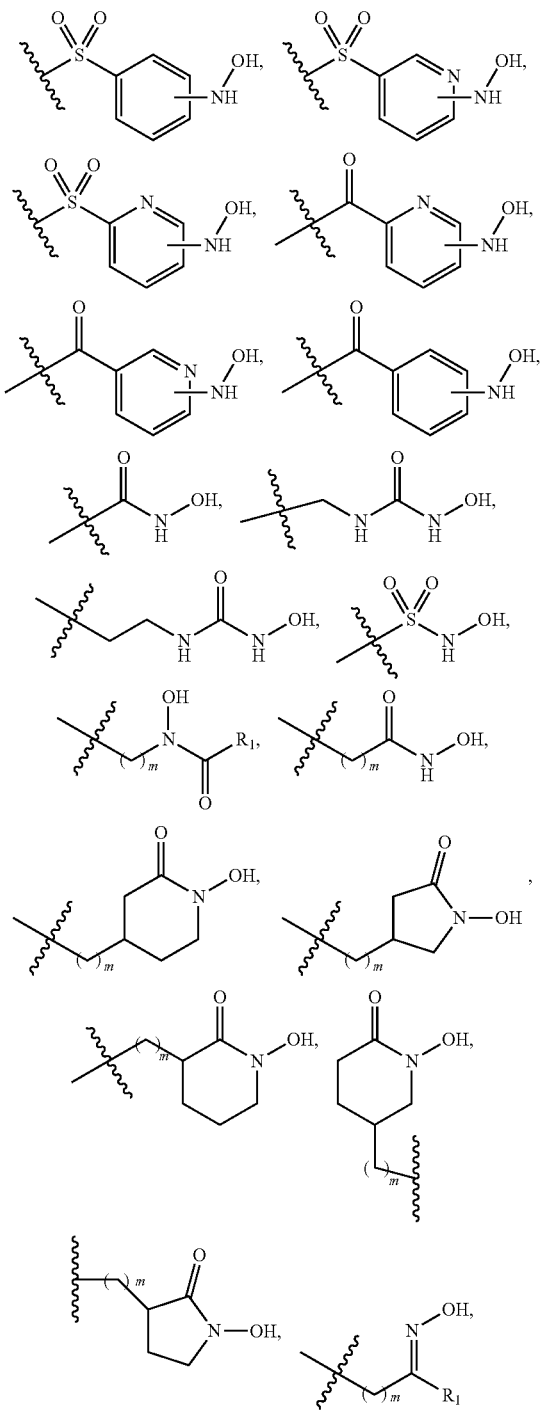

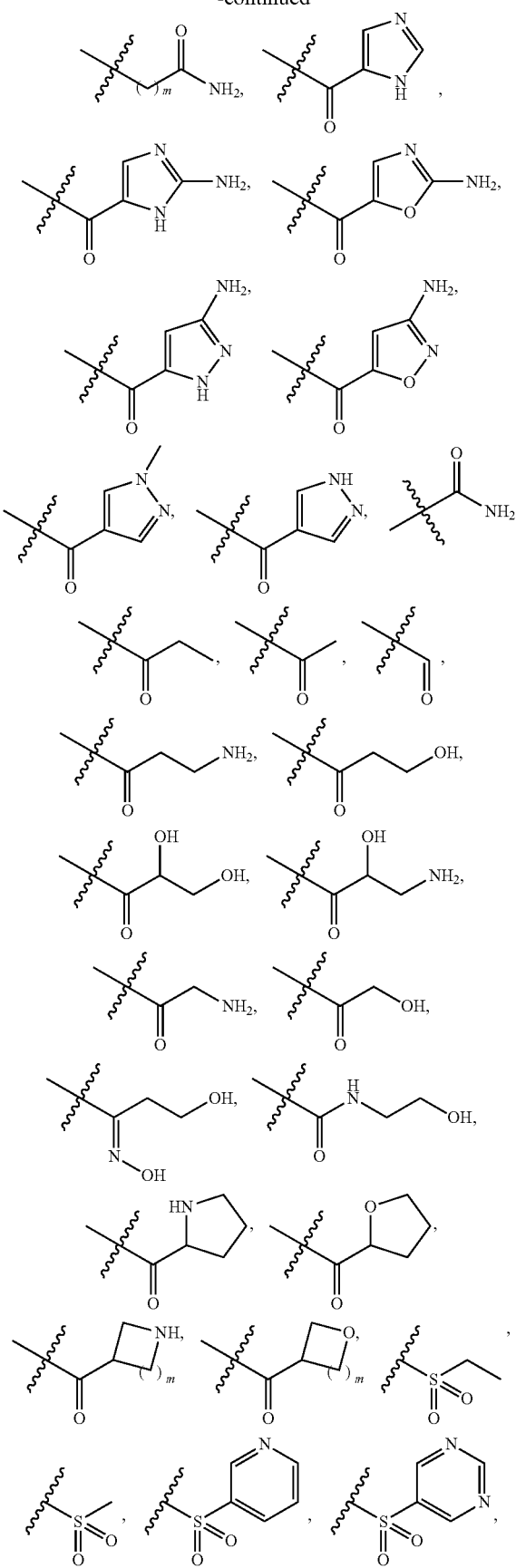
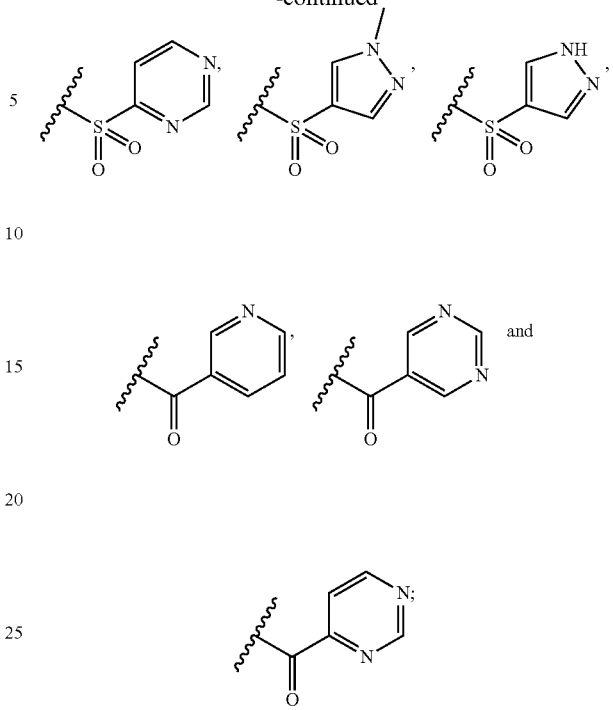
and m, when present, is 0, 1, 2, or 3. In some embodiments, m is 0. In some embodiments, m is 1. In some embodiments, m is 2. In some embodiments, m is 3. In some embodiments, m is 1, 2, or 3. In some embodiments, m is 1 or 2.
In some embodiments, T is
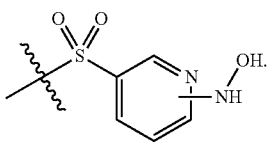
In some embodiments, T is
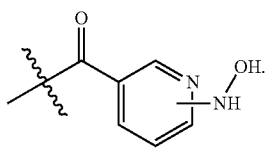
In some embodiments, T is selected from
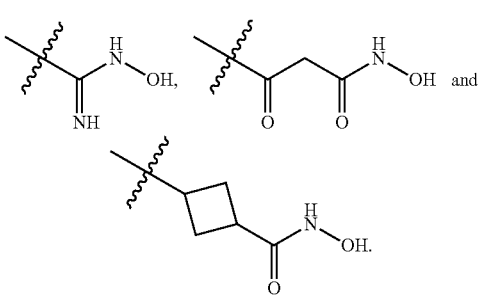

In some embodiments, the compound has the following structure (I'):

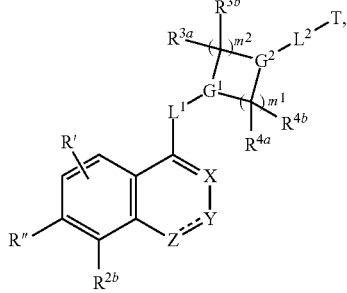
(I')

wherein R' is $R^1$ and R" is $R^{2c}$ or R' is H and R" is $R^1$.

In still more embodiments of the foregoing compounds, the compound has one of the following structures (I'b), (I'c), (I'd) or (I'e):

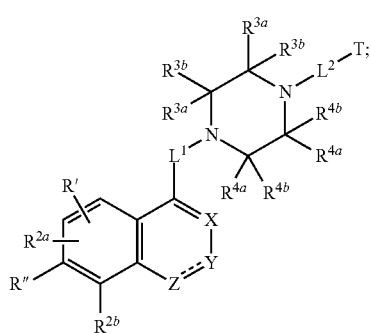
(I'b)

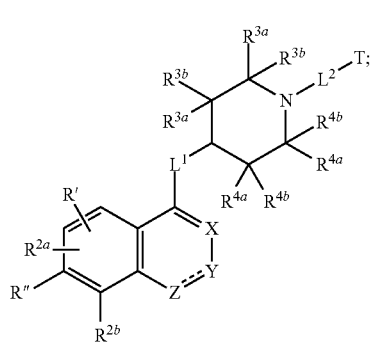
(I'c)

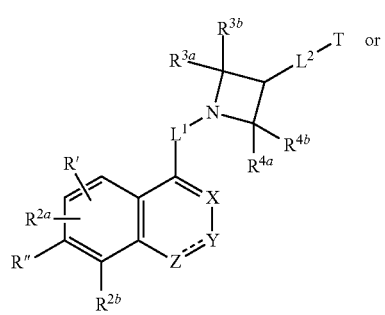
(I'd) or

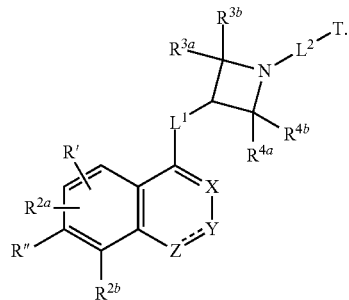
(I'e)

In still more embodiments of the foregoing compounds, the compound has one of the following structures (I'f), (I'g), (I'h) or (I'i):

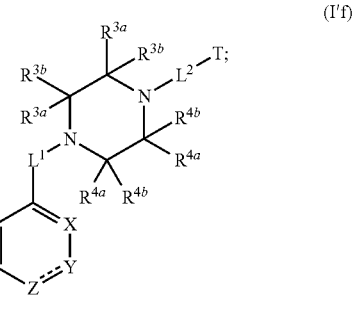
(I'f)

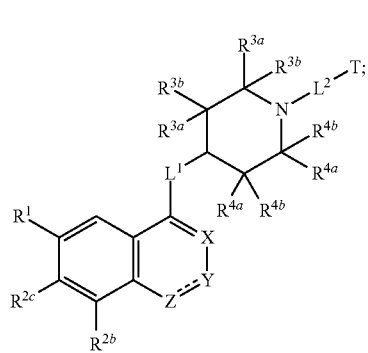
(I'g)

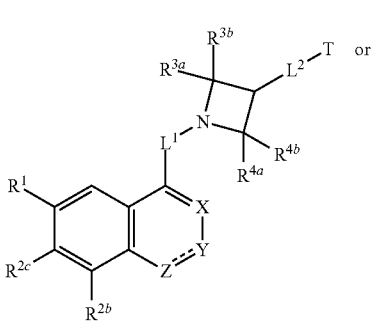
(I'h) or (I'i)

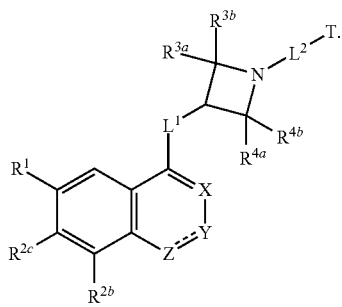

In some embodiments of the compounds of structures (I'f), (I'g), (I'h) or (I'i), $R^1$ is aryl and $R^{2c}$ and $R^{2b}$ are independently selected from H and halo, for example in some further embodiments $R^1$ is aryl and $R^{2c}$ and $R^{2b}$ are independently selected from halo.

In still more embodiments of the foregoing compounds, the compound has one of the following structures (I'j), (I'k), (I'l) or (I'm):

(I'j)

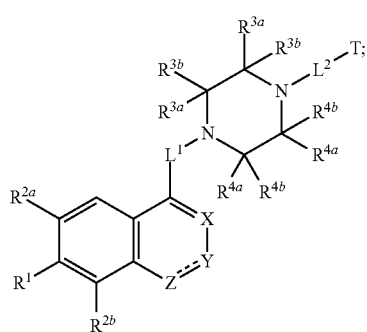

(I'k)

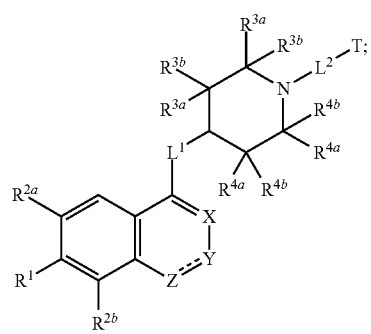

(I'l)

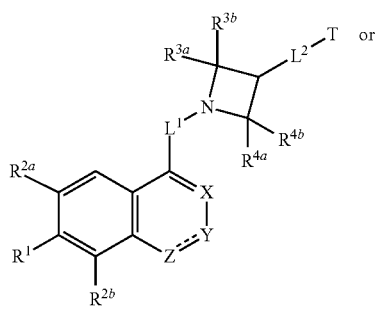

or (I'm)

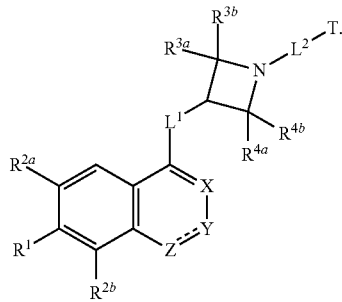

In some embodiments of the compounds of structures (I'j), (I'k), (I'l) or (I'm), $R^1$ is aryl and $R^{2a}$ and $R^{2b}$ are independently selected from H and halo, for example in some further embodiments $R^1$ is aryl and $R^{2a}$ and $R^{2b}$ are independently selected from halo.

In some embodiments of the compounds of structure I, the compound has the structure:

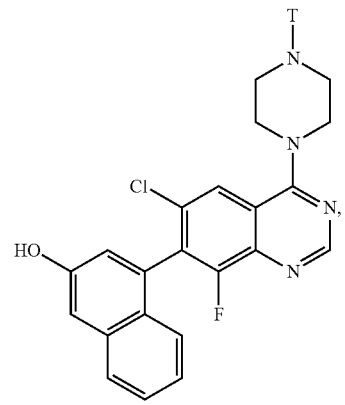

wherein T is as described herein. In some embodiments, T is selected from the group consisting of

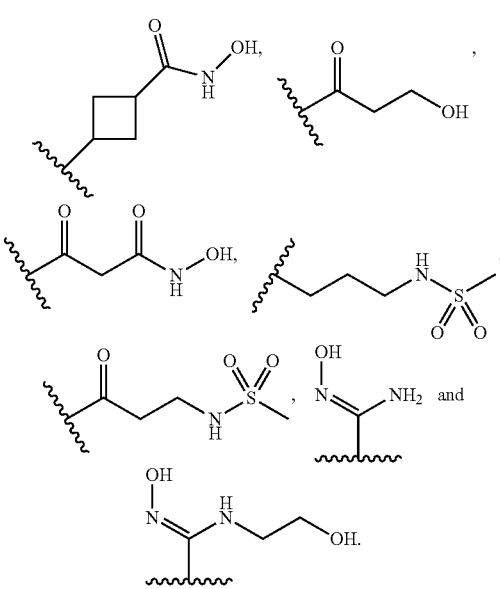

In some embodiments of the compounds of structure I, the compound has the structure:
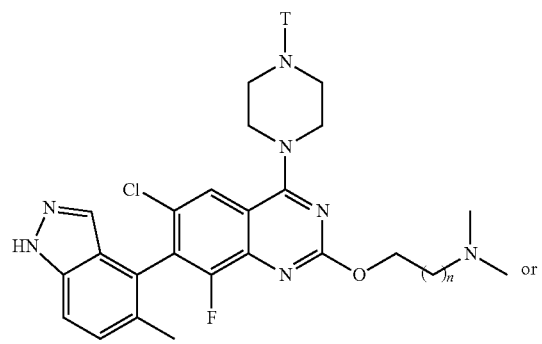
or
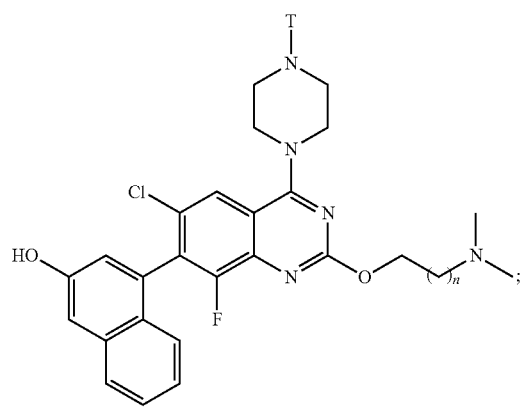
wherein n is 1, 2, or 3; and T is as described herein. In some embodiments, T is selected from the group consisting of:
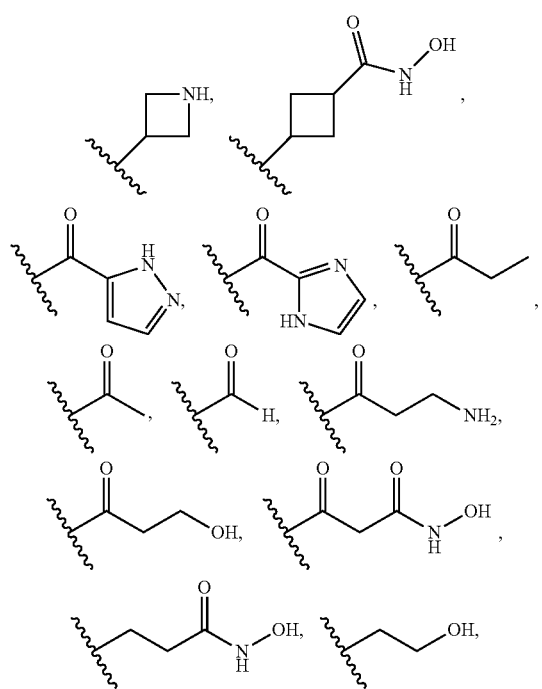
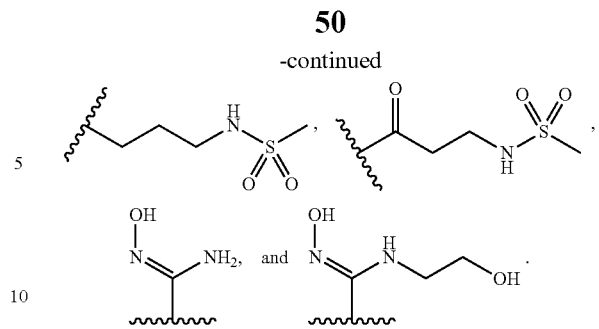
In some embodiments of the compounds of structure I, the compound has the structure:
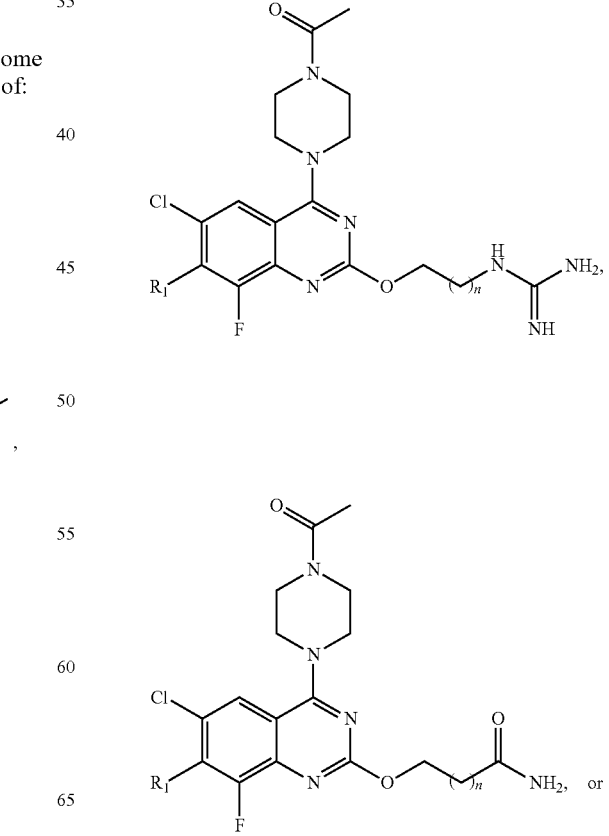

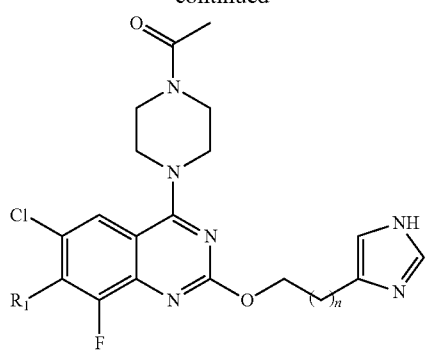
wherein n is 1, 2, or 3; and R¹ is as described herein. In some embodiments, R¹ is
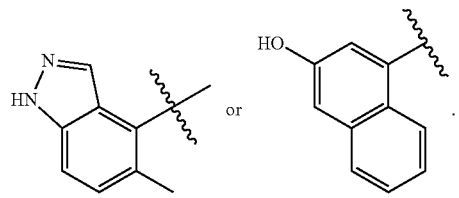 [SMILES: *c1c(C)ccc2[nH]ncc12 ; *c1cc(O)cc2ccccc12]
In other embodiments, the compound has the following structure (I"):
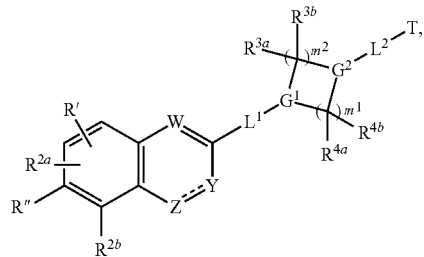
wherein R' is R¹ and R" is $R^{2c}$ or R' is H and R" is R¹.
In some embodiments, the compound has one of the following structures (I"b), (I"c), (I"d) or (I"e):
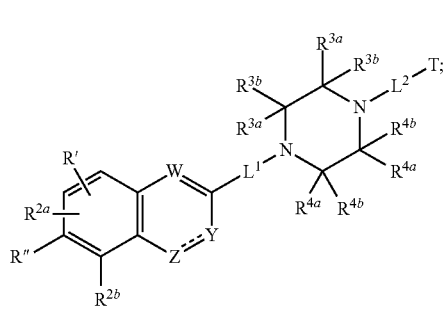
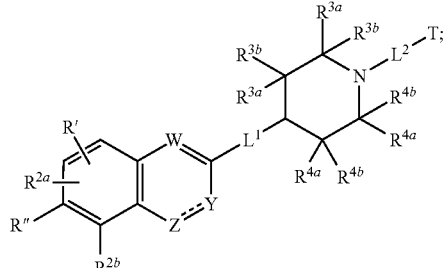
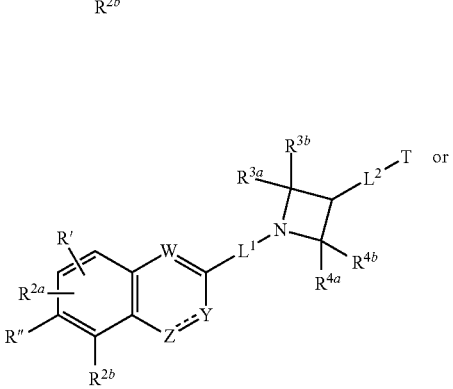
In other embodiments, the compound has one of the following structures (I"f), (I"g), (I"h) or (I"i):
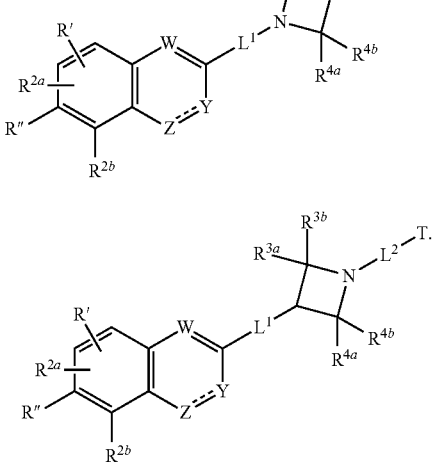
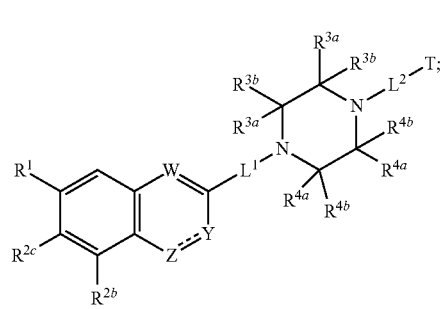
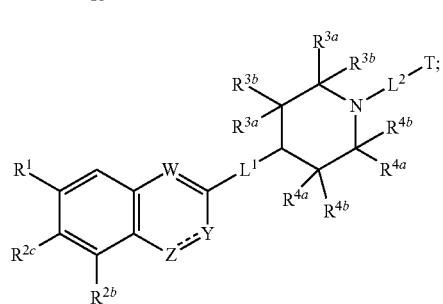

-continued
(I″h)
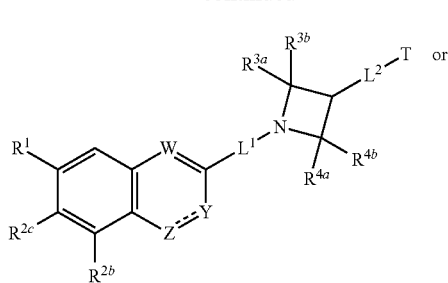
or
(I″i)
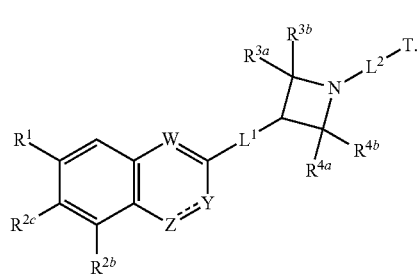
In some different embodiments, the compound has one of the following structures (I″j), (I″k), (I″l) or (I″m):
(I″j)
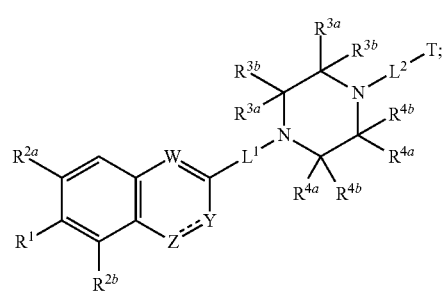
(I″k)
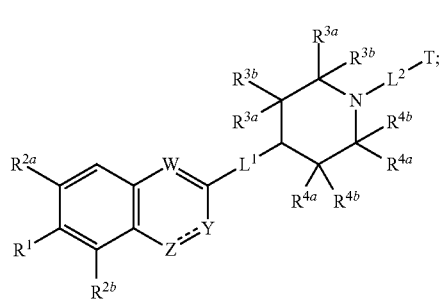
(I″l)
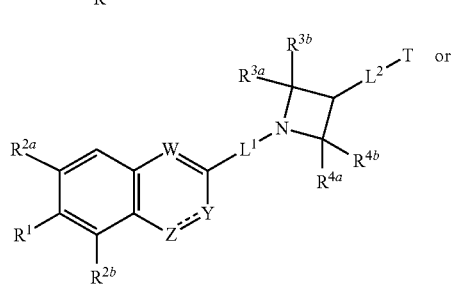
or
(I″m)
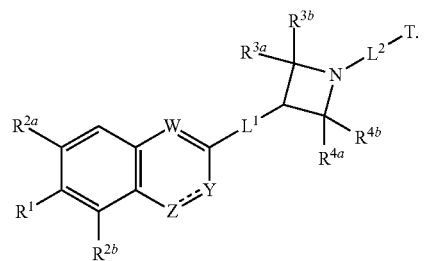
In other various embodiments, the compound has the following structure (I‴):
(I‴)
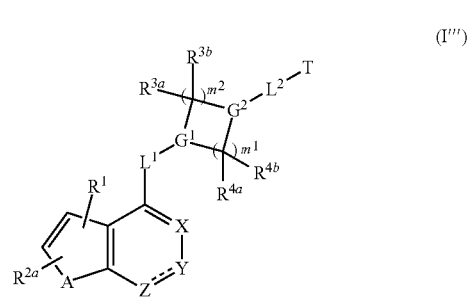
wherein A is NH or S.
In some embodiments, the compound has one of the following structures (I‴b), (I‴c), (I‴d) or (I‴e):
(I‴b)
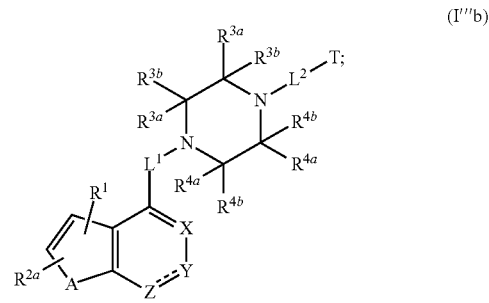
(I‴c)
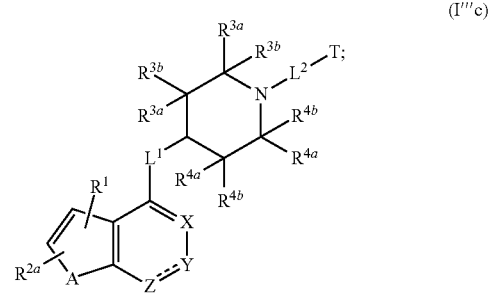

-continued (I'''d)
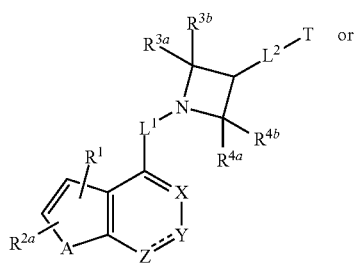

(I'''e)
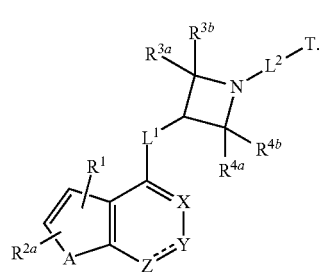

In other embodiments, the compound has one of the following structures (I'''f), (I'''g), (I'''h) or (I'''i):

(I'''f)
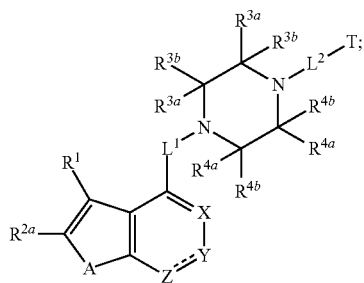

(I'''g)
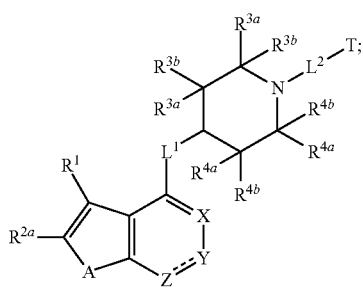

(I'''h)
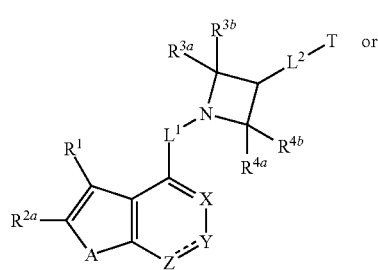

-continued (I'''i)
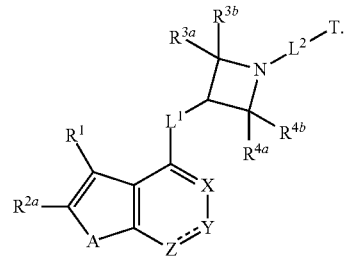

In still other embodiments, provided herein is a compound having the structure (II):

(II)
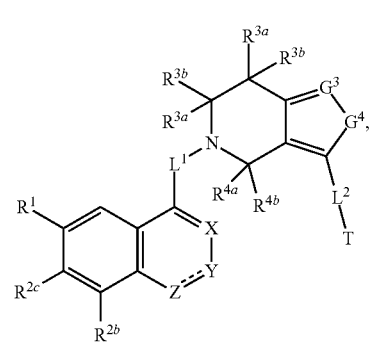

wherein $G^3$ is N or CH and $G^4$ is NH or $CH_2$.

In certain embodiments of any of the foregoing, at least one of $G^1$ or $G^2$ is N. In other embodiments, at least one of W, X or Y is N or $NR^5$. In other embodiments, at least one of W, X or Y is N and at least one of W, X or Y is $CR^6$. For example, in some embodiments two of W, X and Y are N and one of W, X and Y is $CR^6$.

For example, in some different embodiments, the compound has one of the following structures:

(I'n)
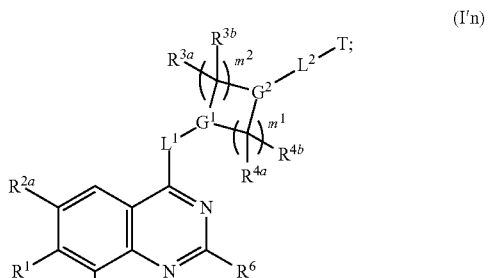

(I'o)
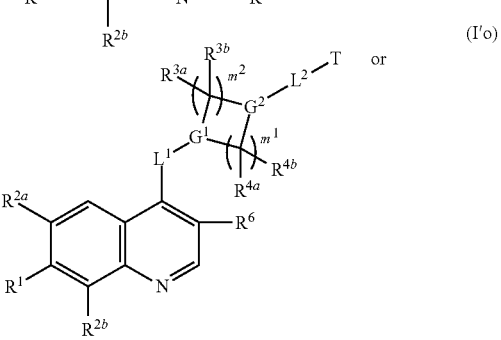

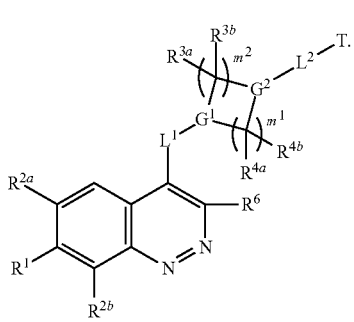

In some embodiments of the compounds of structures (I'n), (I'o) or (I'p), $R^1$ is aryl or heteroaryl and $R^{2a}$ and $R^{2b}$ are independently selected from H and halo, for example in some further embodiments $R^1$ is aryl or heteroaryl and $R^{2a}$ and $R^{2b}$ are independently selected from halo. In other embodiments $R^1$ is aryl or heteroaryl, one of $R^{2a}$ or $R^{2b}$ is halo and the other one of $R^{2a}$ or $R^{2b}$ is H. In other embodiments of the foregoing, $R^6$ is H, cyano, cyanoalkyl, amino, or $C_1$-$C_6$ alkyl.

In yet more of any of the foregoing embodiments, T is not E, and E has the following structure:

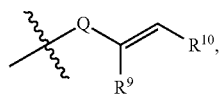

wherein: Q is —C(=O)—, —NR$^8$C(=O)—, —S(=O)$_2$— or —NR$^8$S(=O)$_2$—; $R^8$ is H, $C_1$-$C_6$alkyl or hydroxylalkyl; and $R^9$ and $R^{10}$ are each independently H, cyano, $C_1$-$C_6$alkyl, aminoalkyl, alkylaminoalkyl, or hydroxylalkyl or $R^9$ and $R^{10}$ join to form a carbocyclic or heterocyclic ring.

In still other of any of the foregoing embodiments, T is not E, and E has the following structure:

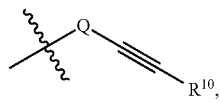

wherein: Q is —C(=O)—, —NR$^8$C(=O)—, —S(=O)$_2$— or —NR$^8$S(=O)$_2$—; $R^8$ is H, $C_1$-$C_6$alkyl or hydroxylalkyl; and $R^{10}$ is H, $C_1$-$C_6$ alkyl, aminoalkyl, alkylaminoalkyl or hydroxylalkyl.

In some embodiments $m^1$ is 1. In other embodiments $m^1$ is 2. In still more embodiments, $m^1$ is 3. In different embodiments, $m^2$ is 1. In some other embodiments, $m^2$ is 2. In yet still more embodiments, $m^2$ is 3. In some other particular embodiments of any of the foregoing compounds, $m^1$ is 1, and $m^2$ is 1. In other embodiments, $m^1$ is 1 and, $m^2$ is 2. In still other embodiments $m^1$ is 2, and $m^2$ is 2. In more embodiments, $m^1$ is 1, and $m^2$ is 3.

In any of the foregoing embodiments, $G^1$ and $G^2$ are each independently selected from N and CH. In some embodiments, at least one of $G^1$ or $G^2$ is N. In some embodiments, each of $G^1$ and $G^2$ are N. In some embodiments, each of $G^1$ and $G^2$ are N and $m^1$ and $m^2$ are each 2. In some other embodiments, at least one of $G^1$ or $G^2$ is CH. In other embodiments, each of $G^1$ and $G^2$ are CH.

Without wishing to be bound by a theory, the correct selection of the $R^1$ substituent may play a part in the compounds' inhibitory activity (e.g., against K-Ras, H-Ras or N-Ras G12C). In some embodiments, $R^1$ is selected from aryl and heterocyclyl (e.g., heteroaryl or aliphatic heterocyclyl), each of which is optionally substituted with one or more substituents. In some embodiments, $R^1$ is capable of reversible interaction with K-Ras, H-Ras or N-Ras G12C mutant protein. In some embodiments $R^1$ has high affinity towards K-Ras, H-Ras or N-Ras and is highly specific towards G12C K-Ras, H-Ras or N-Ras. In some embodiments $R^1$ is capable of hydrophobic interaction with K-Ras, H-Ras or N-Ras G12C. In some embodiments $R^1$ is able to form hydrogen bonds with various residues of G12C K-Ras, H-Ras or N-Ras protein.

In other of the foregoing embodiments, $R^1$ is heterocyclyl, heteroaryl or aryl.

In certain embodiments of any of the foregoing, $R^1$ is aryl. For example, in some embodiments $R^1$ is phenyl. In other embodiments, $R^1$ is naphthyl. In some of these embodiments, $R^1$ is unsubstituted aryl, such as unsubstituted phenyl or unsubstituted naphthyl. In other embodiments, $R^1$ is substituted with one or more substituents. In some of these embodiments, the substituents are selected from halo, cyano, hydroxyl, $C_1$-$C_6$alkyl, $C_1$-$C_6$alkoxy and $C_3$-$C_8$cycloalkyl. In other more specific embodiments, the substituents are selected from fluoro, chloro, bromo, hydroxyl, methoxy and cyclopropyl.

In other embodiments, the $R^1$ substituents are selected from halo, cyano, cyano$C_1$-$C_6$alkyl, cyano$C_3$-$C_8$cycloalkyl, hydroxyl, $C_1$-$C_6$alkyl, $C_1$-$C_6$alkylcycloalky, $C_2$-$C_6$alkynyl, $C_1$-$C_6$alkoxy, $C_1$-$C_6$haloalkoxy, $C_1$-$C_6$alkylaminyl, $C_1$-$C_6$ alkyl carbonylaminyl, $C_1$-$C_6$hydroxylalkyl, $C_1$-$C_6$haloalkyl, $C_1$-$C_6$alkoxyalkyl, aminosulfone, aminocarbonyl, aminocarbonyl$C_1$-$C_6$alkyl, aminocarbonyl$C_3$-$C_8$cycloalkyl, $C_1$-$C_6$alkylaminocarbonyl, $C_3$-$C_8$cycloalkylaminocarbonyl, $C_3$-$C_8$cycloalkylalkyl and $C_3$-$C_8$cycloalkyl, $C_3$-$C_8$fused cycloalkyl and heteroaryl.

In still other embodiments, the $R^1$ substituents are selected from fluoro, chloro, bromo, cyano, hydroxyl, hydroxylmethyl, methoxy, methoxymethyl, ethyl, isopropyl, trifluoromethyl, aminocarbonyl and cyclopropyl.

In certain embodiments, $R^1$ has one of the following structures:

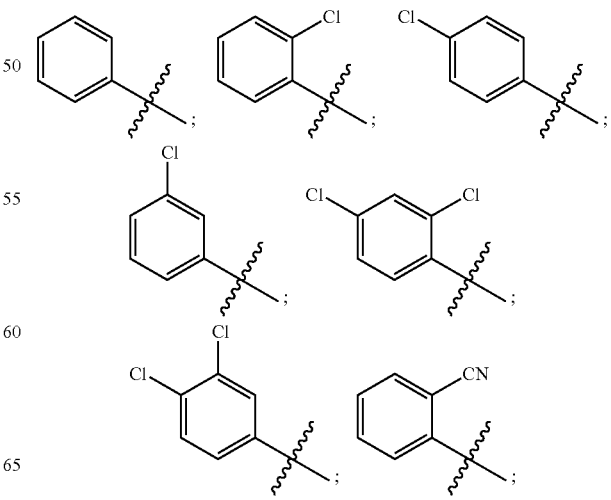

-continued
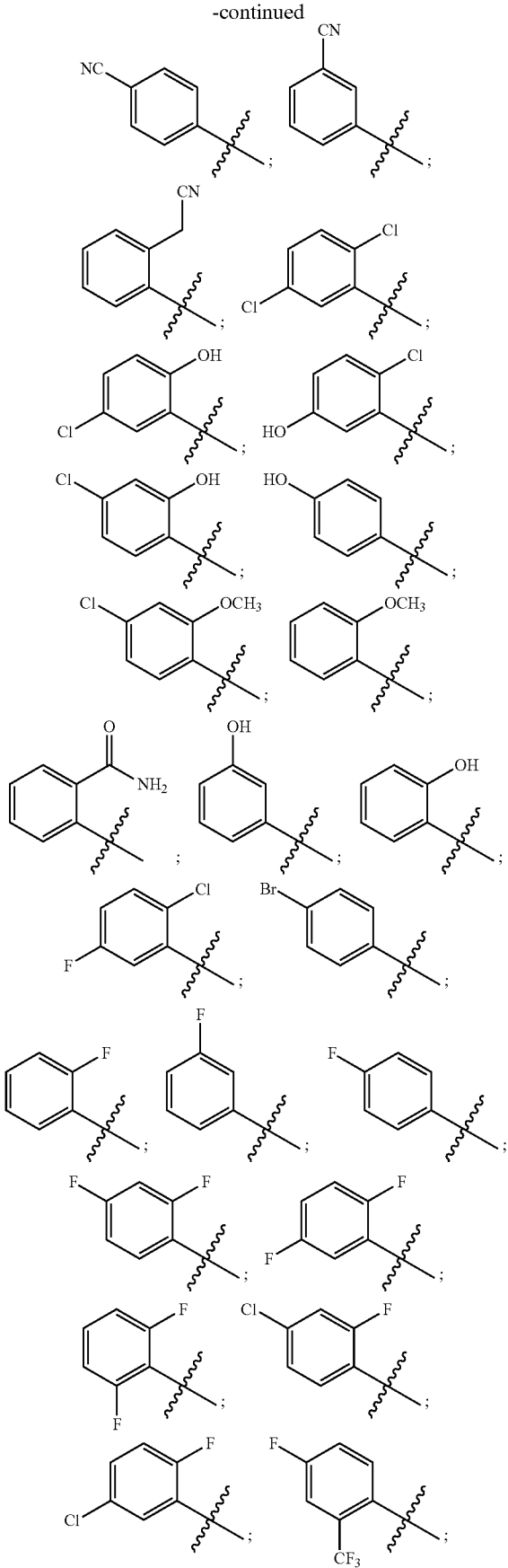
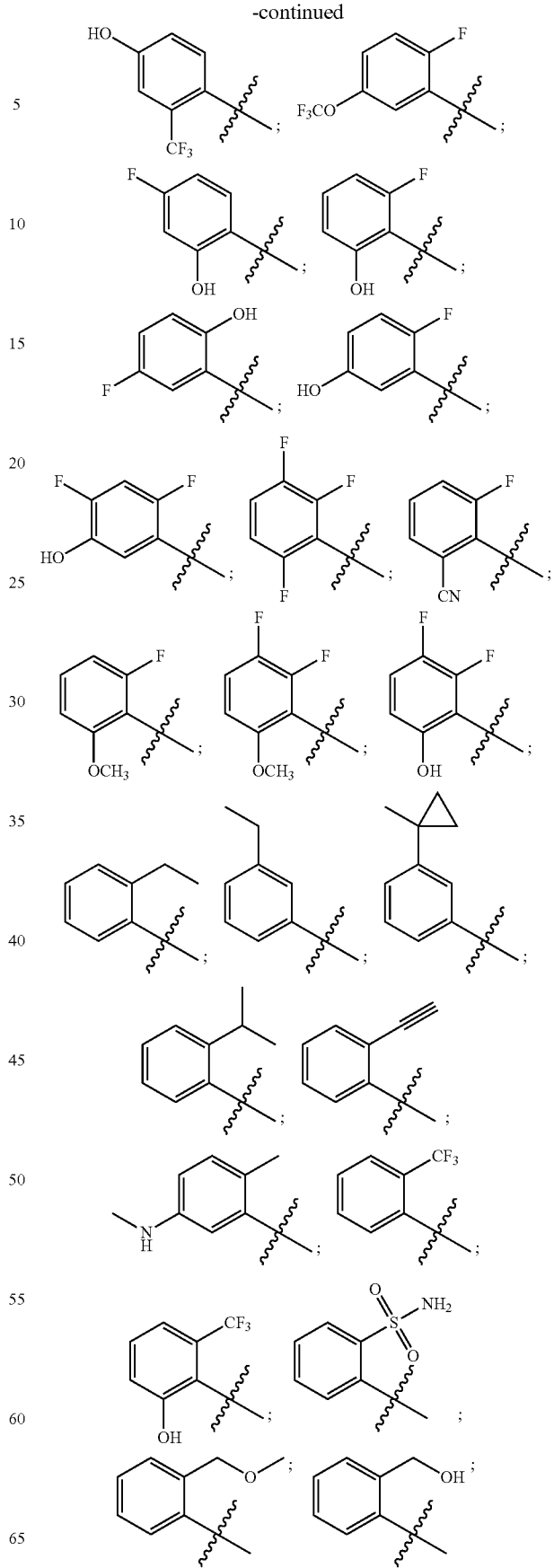

61
-continued
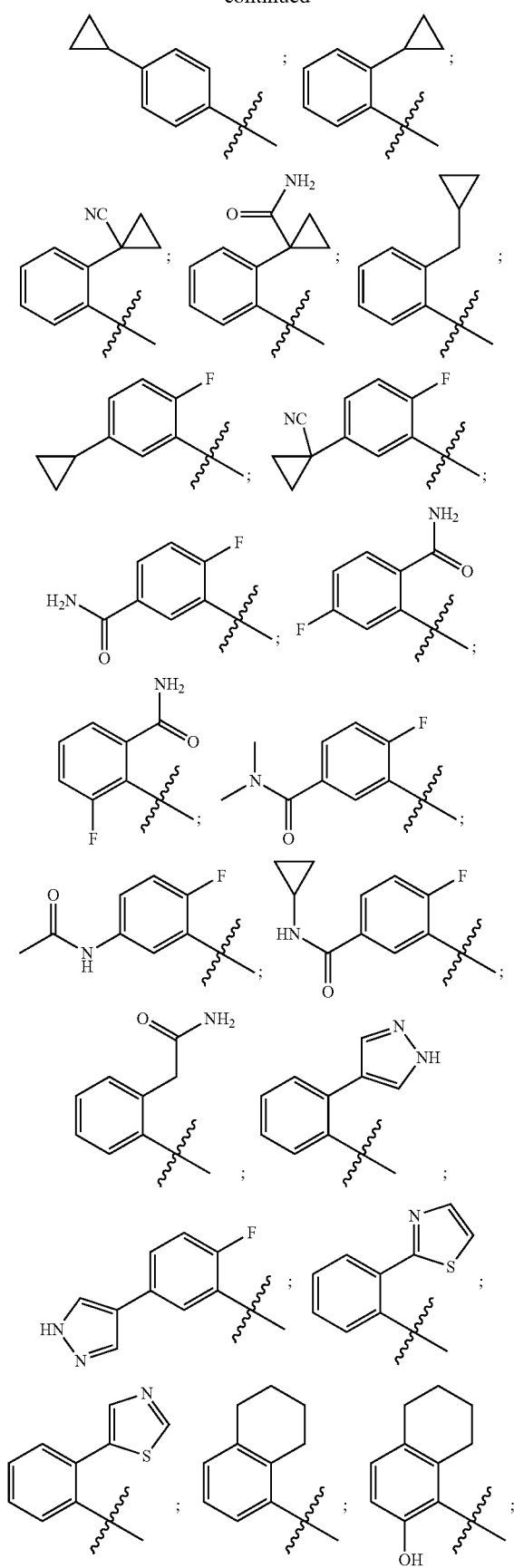
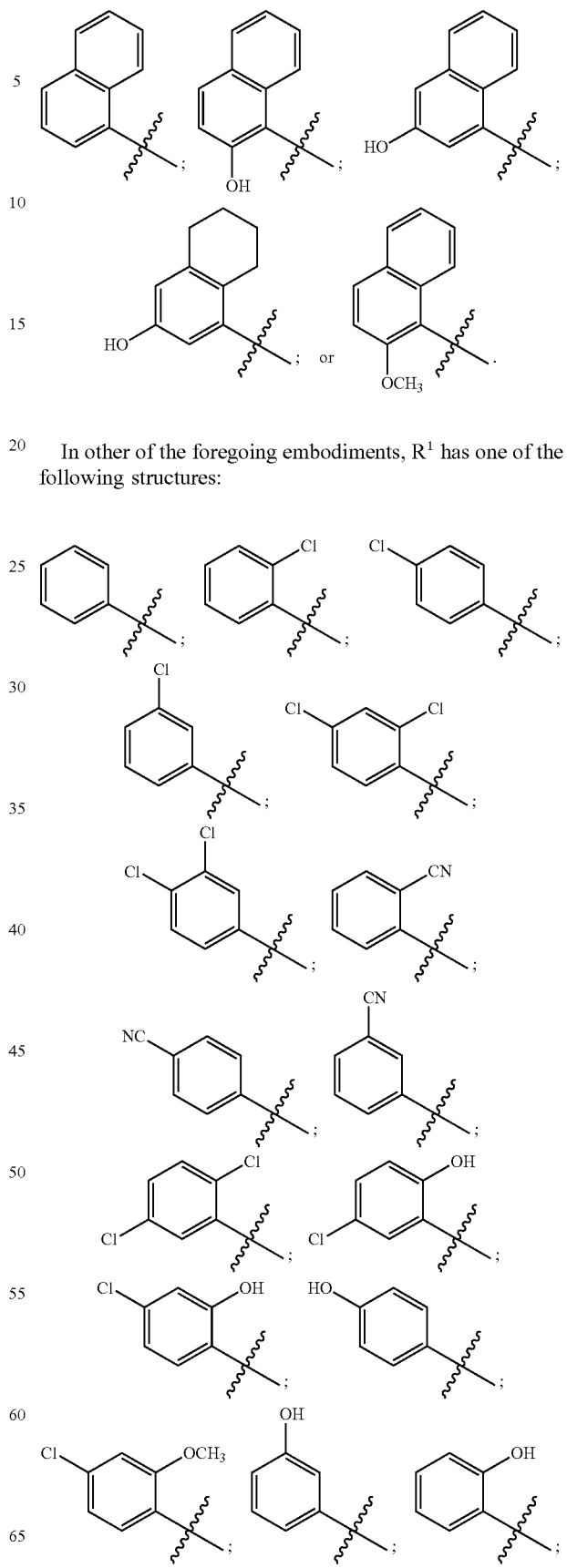
62
-continued
In other of the foregoing embodiments, R[1] has one of the following structures:

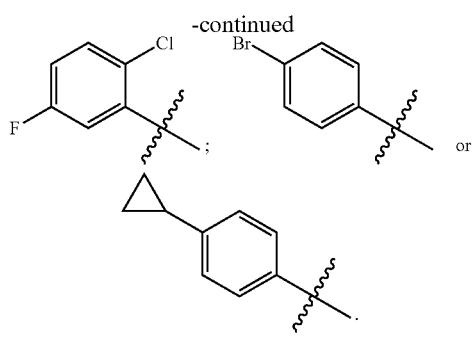

In some different embodiments of any of the foregoing, $R^1$ is heteroaryl. In certain embodiments, $R^1$ comprises oxygen, sulfur, nitrogen or combinations thereof. In some of these embodiments, $R^1$ comprises sulfur or nitrogen. In certain embodiments, $R^1$ is thiophenyl, pyridinyl, pyridinonyl, pyrimidinyl, benzooxazolyl, benzoisoxazolyl, benzodioxazolyl, benzoimidazolyl, quinolinyl, quinolinonyl, dihydroquinolinonyl, tetrahydroquinolinyl, quinazolinyl, indazolyl, indolinonyl, benzothiophenyl or dihydrobenzodioxinyl.

For example, in some embodiments $R^1$ is pyridinyl. In some embodiments $R^1$ is unsubstituted pyridinyl, for example unsubstituted pyridin-4-yl or unsubstituted pyridin-3-yl. In other embodiments $R^1$ is thiophenyl. In some embodiments $R^1$ is unsubstituted thiophenyl, for example unsubstituted thiophen-2-yl.

In other embodiments, $R^1$ is substituted with one or more substituents. For example, in some embodiments, the substituents are selected from halo, $C_1$-$C_6$alkyl, $C_1$-$C_6$alkoxy, or $C_2$-$C_6$alkenylcarbonylaminyl. In some of these embodiments, the substituents are selected from halo and $C_1$-$C_6$alkyl. In other embodiments, the substituents are selected from fluoro, chloro, amino and methyl. For example, in more specific embodiments, the substituents are selected from chloro and methyl.

In certain embodiments, $R^1$ has one of the following structures:

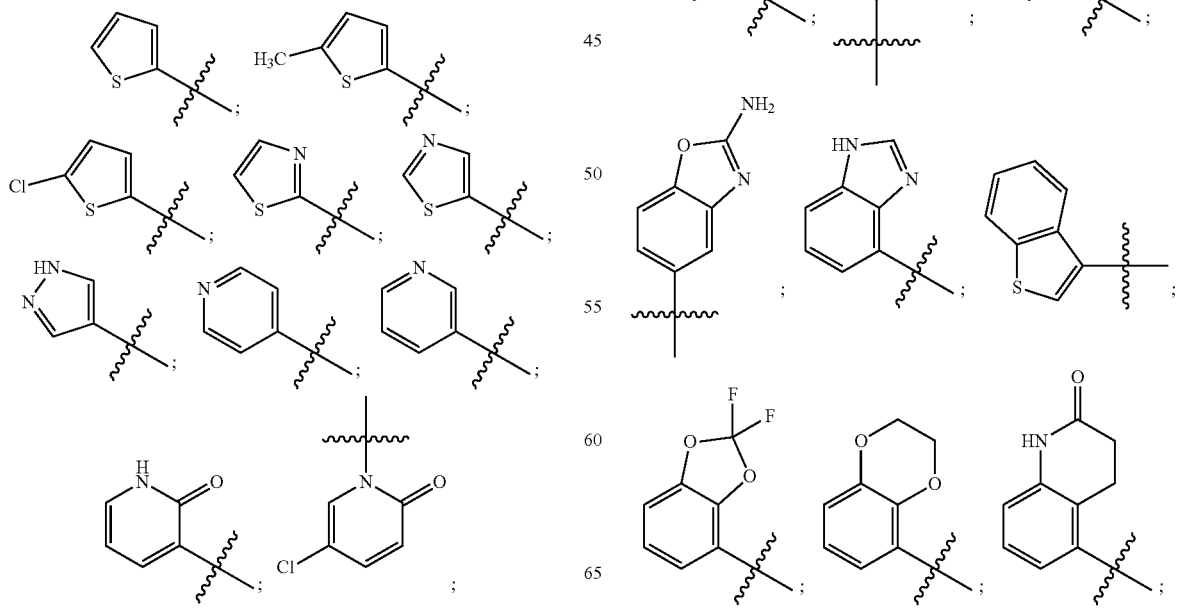

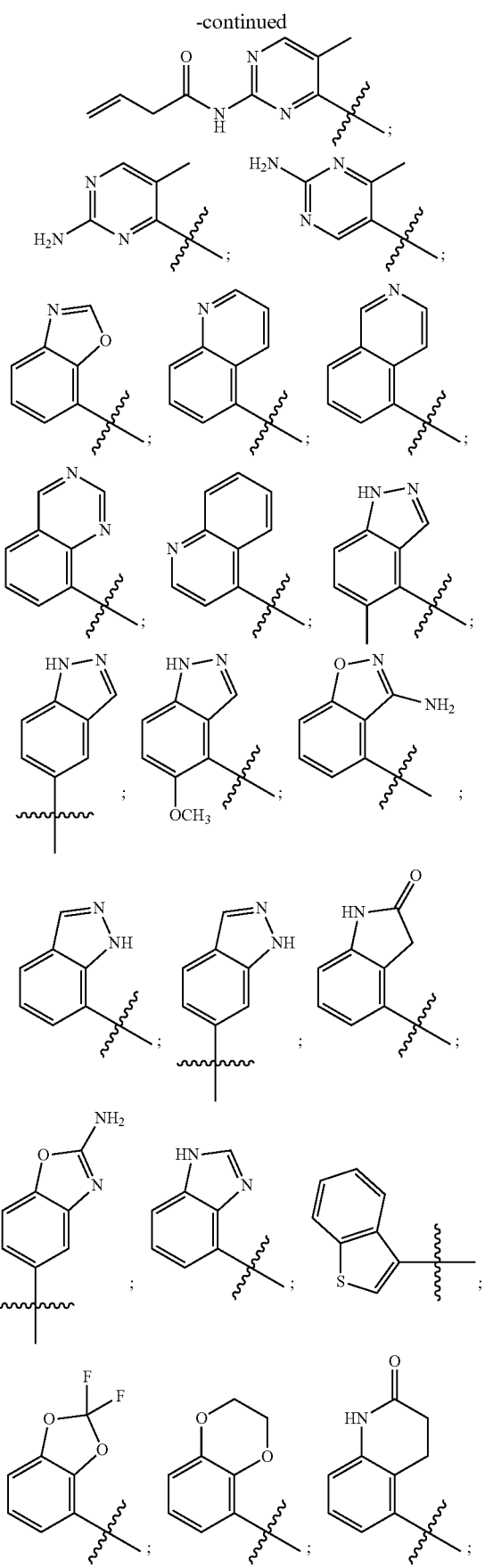

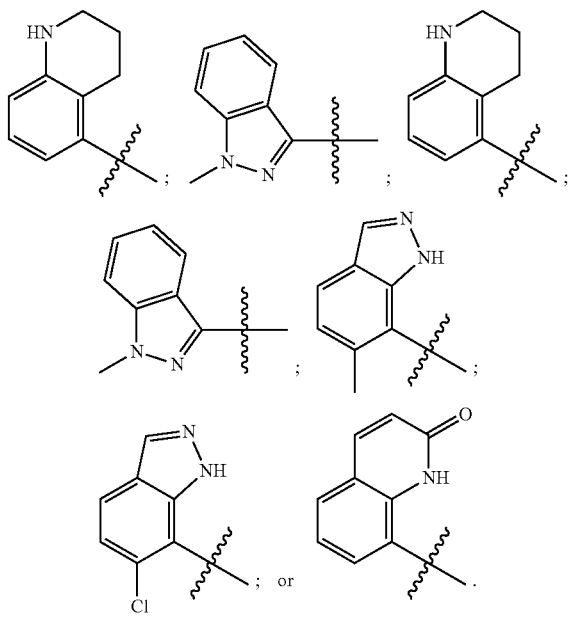

In some embodiments, R¹ has the structure

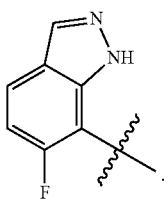 [SMILES: *c1c(F)ccc2cn[nH]c12]

In some of the foregoing embodiments, R¹ has one of the following structures:

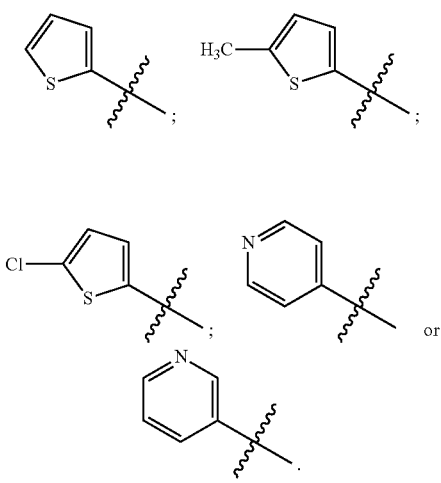

In still other embodiments, R¹ is aliphatic heterocyclyl. In some embodiments the aliphatic heterocyclyl comprises oxygen and/or nitrogen. In some further embodiments, R¹ is morpholinyl. For example, in some embodiments R¹ has the following structure:

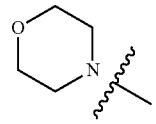

In various embodiments of the foregoing, R¹ is unsubstituted.

In some of the foregoing embodiments, $R^{2a}$ is H. In other embodiments, $R^{2a}$ is halo, for example in some embodiments $R^{2a}$ is chloro or fluoro. In still other embodiments of the foregoing, $R^{2a}$ is $C_1$-$C_6$alkyl. In some embodiments $R^{2a}$ is $C_3$-$C_8$ cycloalkyl, such as cyclopropyl.

In other embodiments of the foregoing compounds, $R^{2b}$ and $R^{2c}$, when present, are H. In different embodiments, $R^{2b}$ and $R^{2c}$, when present, are each independently halo. In yet other embodiments, $R^{2b}$, when present, is halo. In more embodiments, $R^{2c}$, when present, is halo. In certain of the foregoing embodiments, halo is chloro or fluoro.

In certain embodiments of any of the foregoing, $R^6$ is H.

The Q moiety is typically selected to optimize the reactivity (i.e., electrophilicity) of E. In certain of the foregoing embodiments, Q is —C(=O)—. In other embodiments, Q is —S(=O)$_2$—. In still more embodiments, Q is —NR$^8$C(=O)—. In still more different embodiments, Q is —NR$^8$S(=O)$_2$—.

In some of the immediately foregoing embodiments, $R^8$ is H. In other of these embodiments, $R^8$ is hydroxylalkyl, for example in some embodiments the hydroxylalkyl is 2-hydroxylalkyl.

In some of any one of the foregoing embodiments, at least one of $R^9$ or $R^{10}$ is H. For example, in some embodiments each of $R^9$ and $R^{10}$ are H.

In other of the foregoing embodiments, $R^{10}$ is alkylaminoalkyl. In some of these embodiments, $R^{10}$ has the following structure:

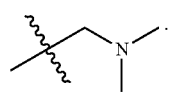

In other embodiments, $R^{10}$ is hydroxylalkyl, such as 2-hydroxylalkyl.

In some other different embodiments of the foregoing embodiments, $R^9$ and $R^{10}$ join to form a carbocyclic ring. For example, in some of these embodiments the carbocyclic ring is a cyclopentene, cyclohexene or phenyl ring. In other embodiments, the carbocyclic ring is a cyclopentene or cyclohexene ring. In other embodiments, the carbocyclic ring is a phenyl ring, for example a phenyl ring having the following structure:

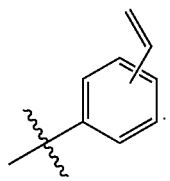

In some of any of the foregoing embodiments, T is not E, and E is an electrophile capable of bonding with a K-Ras, H-Ras or N-Ras protein comprising G12C mutation. In some embodiments, T is not E, and the electrophile E is capable of forming an irreversible covalent bond with a G12C mutant K-Ras, H-Ras or N-Ras protein. In some cases, the electrophile E may bind with the cysteine residue at the position 12 of a G12C mutant K-Ras, H-Ras or N-Ras protein. In various embodiments of any of the foregoing, T is not E, and E has one of the following structures:

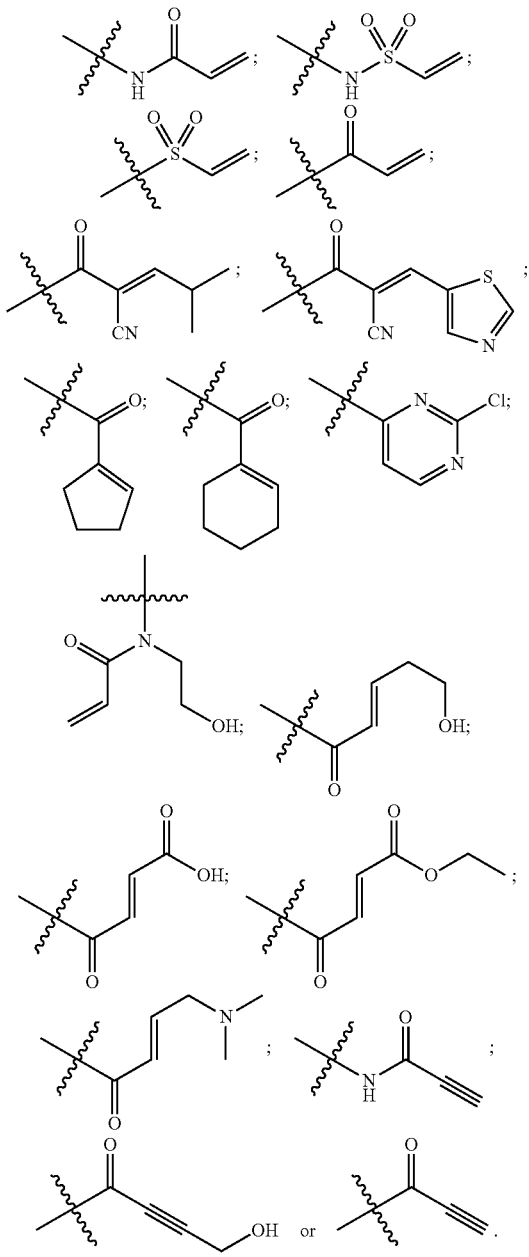

In different embodiments, T is not E, and E has the following structures:

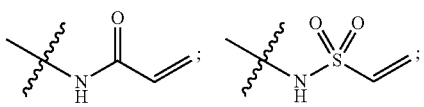

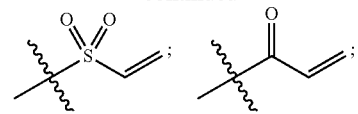

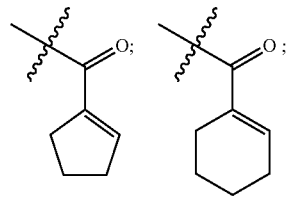

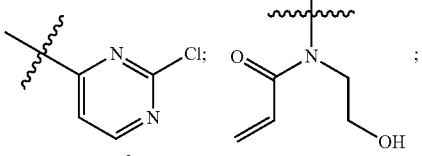

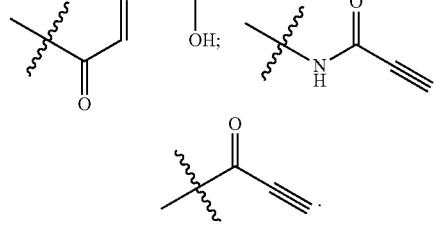

In some cases, T is not E, and E has one of the following structures:

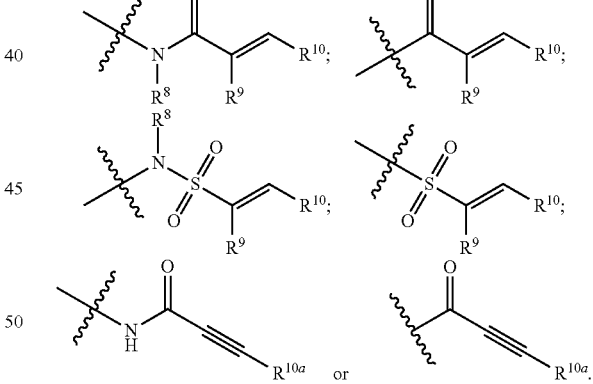

wherein:
$R^8$ is H or $C_1$-$C_6$alkyl;
$R^9$ is H, cyano or $C_1$-$C_6$alkyl, or $R^9$ joins with $R^{10}$ to form a carbocycle;
$R^{10}$ is H or $C_1$-$C_6$alkyl or $R^{10}$ joins with $R^9$ to form a carbocycle and
$R^{10a}$ is H or $C_1$-$C_6$alkyl. In some embodiments E is

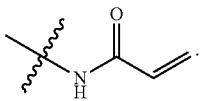

In some embodiments E is

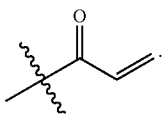 [SMILES: *C(=O)C=C]

In some embodiments, T is not E, and E is

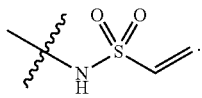 [SMILES: *NS(=O)(=O)C=C]

In some embodiments, T is a polar group capable of forming a complex with a Ras protein via an interaction other than one resulting in a covalent bond with the cysteine residue at position 12 of a K-Ras, H-Ras or N-Ras G12C mutant protein. The T group can form a direct or indirect (i.e. through one or more water molecules) complex with a Ras protein. In some embodiments, T is a polar group capable of forming a bond with a metal ion, wherein the metal ion is complexed to a Ras protein. In some embodiments, T is a metal chelating moiety. In some embodiments, T is a polar group capable of directly or indirectly (e.g. through water) forming one or more interactions with a beta-phosphate of nucleotide (GDP) or G12D residue of a Ras protein. In some embodiments, the Ras protein is a K-Ras, H-Ras or N-Ras wild-type protein. In other embodiments, the Ras protein is a K-Ras, H-Ras or N-Ras mutant protein. In some embodiments, the Ras protein is a K-Ras, H-Ras or N-Ras G12C mutant protein.

In some embodiments, T has a molecular weight less than 400, 350, 300, 250, 200, 190, 180, 170, 160, 150, 140, 130, 120, 110, 100, 90, 80, 70, 60, or 50 Daltons. For example, in some embodiments, T has a molecular weight less than 200 daltons. In some embodiments, T has a molecular weight of greater than 40, 50, 60, 70, 80, 90, 100, or 110 Daltons. For example, in some embodiment, T has a molecular weight of greater than 50 Daltons. In some embodiments, T has a molecular weight between about 50 and 300, 50 and 250, 50 and 200, 50 and 150, or 50 and 100 Daltons.

In some embodiments, T is an optionally substituted alkyl group comprising at least 1, 2, 3, 4, 5, 6, 7, 8, or 9 heteroatoms selected from N, O, and S. In some embodiments, T is an optionally substituted alkyl group comprising at least 1, 2, 3, 4, or 5 nitrogen atoms. In some embodiments, T is an optionally substituted alkyl group comprising at least 1, 2, 3, 4, or 5 oxygen atoms. In some embodiments, T is an optionally substituted alkyl group comprising at least 1, 2, 3, 4, or 5 sulfur atoms. In some embodiments, T is an optionally substituted alkyl group comprising at least 1, 2, 3, 4, 5, 6, 7, 8, or 9 heteroatoms selected from N, O, and S, wherein T has a molecular weight between 50 and 300 Daltons, and wherein T does not comprise an electrophilic group capable of forming a covalent bond with a cysteine. In some embodiments, T does not comprise a Michael acceptor. In some embodiments, T does not comprise an alpha-beta unsaturated carbonyl group.

In some cases, T is selected from the group consisting of

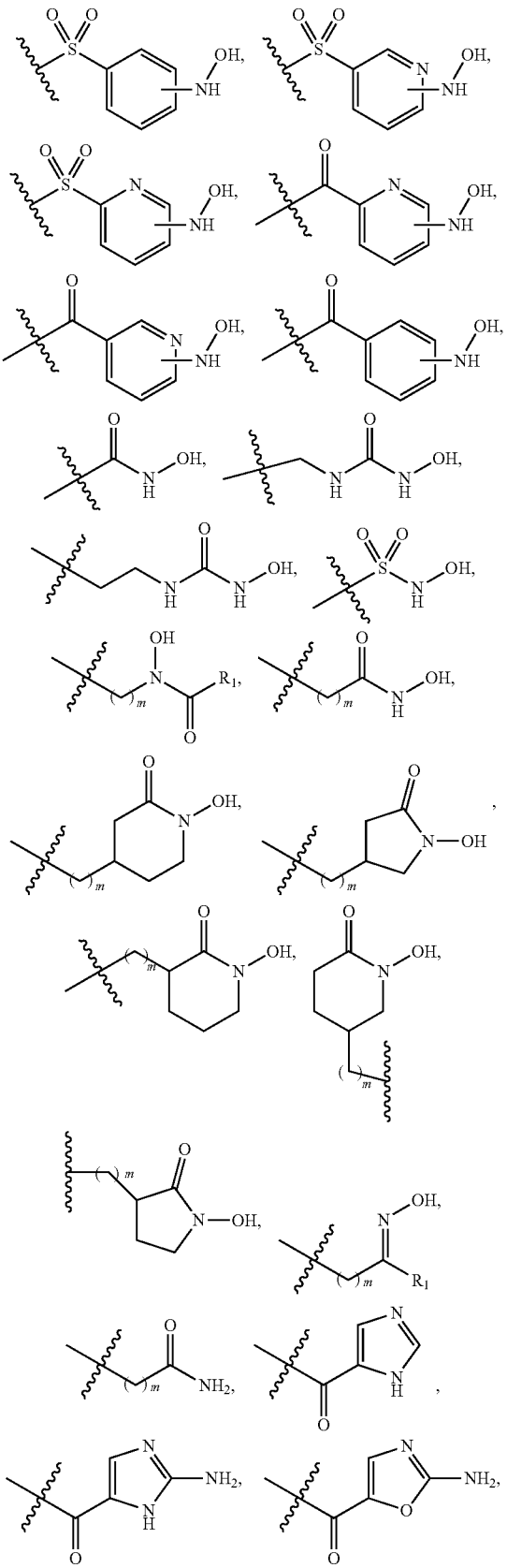

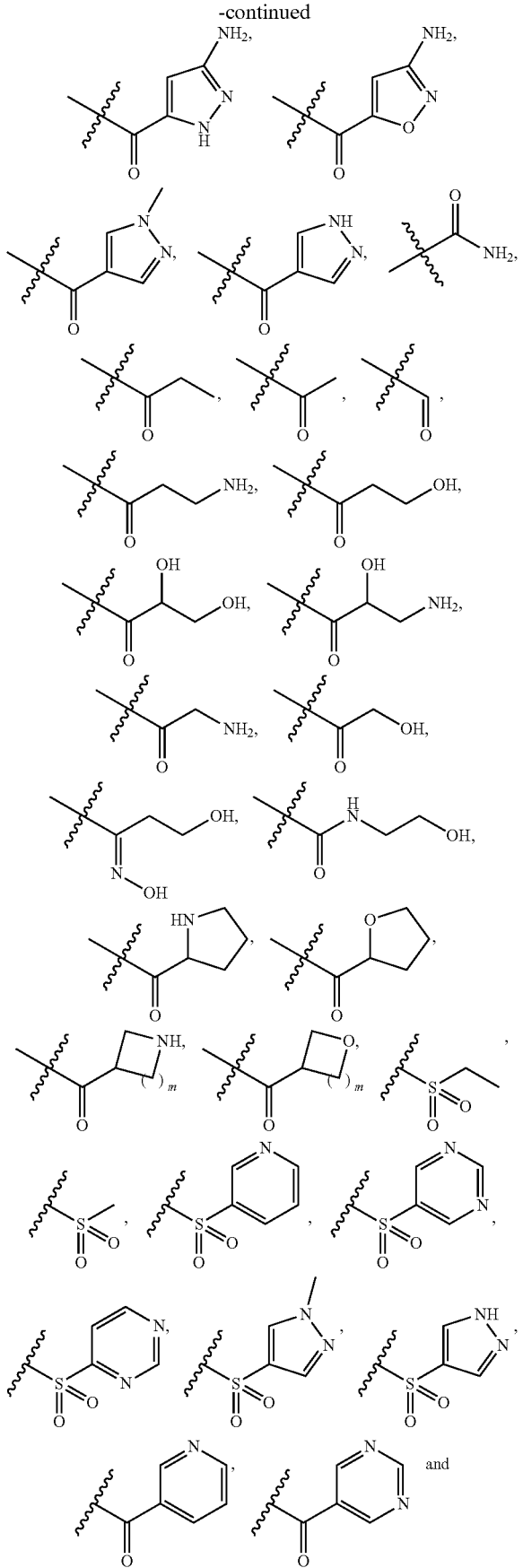
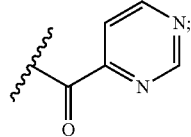
and m, when present, is 0, 1, 2, or 3. In some embodiments, m is 0. In some embodiments, m is 1. In some embodiments, m is 2. In some embodiments, m is 3. In some embodiments, m is 1, 2, or 3. In some embodiments, m is 1 or 2. In some embodiments, T is
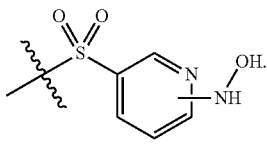
In some embodiments, T is
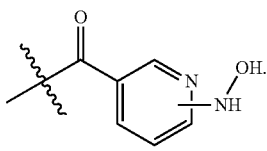
In some embodiments, T is selected from
In some embodiments, T is selected from the group consisting of:

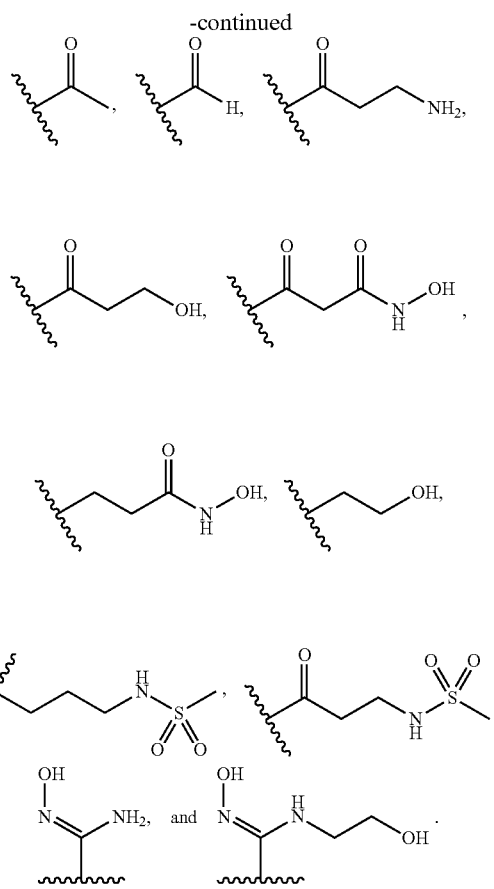

In some of any of the foregoing embodiments, $L^1$ is a bond. In other embodiments, $L^1$ is $NR^7$. For example, in some of these embodiments, $R^7$ is $C_1$-$C_6$alkyl. In other embodiments, $L^1$ is NH.

$L^2$ can be selected to provide proper spacing and/or orientation for the T group to form a complex with the K-Ras, H-Ras or N-Ras protein. In some of the foregoing embodiments, $L^2$ is a bond. In other of the foregoing embodiments, $L^2$ is alkylene. In some embodiments, the alkylene is substituted. In other embodiments the alkylene is unsubstituted. For example, in some embodiments $L^2$ is $CH_2$ or $CH_2CH_2$.

In certain embodiments, $R^{3a}$ and $R^{3b}$ are, at each occurrence, independently H, —OH, —$NH_2$, —$CO_2H$, halo, cyano, hydroxylalkyl, aminoalkyl, cyanoalkyl, carboxyalkyl or aminocarbonyl, and $R^{4a}$ and $R^{4b}$ are, at each occurrence, independently H, —OH, —$NH_2$, —$CO_2H$, halo, cyano, hydroxylalkyl, aminoalkyl, cyanoalkyl, carboxyalkyl or aminocarbonyl.

In other of the foregoing embodiments, $R^{3a}$ and $R^{4a}$ are, at each occurrence, independently H, —OH, hydroxylalkyl, cyano, or aminocarbonyl and $R^{3b}$ and $R^{4b}$ are H.

In certain other embodiments, $R^{3a}$ and $R^{4a}$ are H and $R^{3b}$ and $R^{4b}$ are, at each occurrence, independently H, —OH, —$NH_2$, —$CO_2H$, halo, cyano, hydroxylalkyl, aminoalkyl, cyanoalkyl, carboxyalkyl or aminocarbonyl.

In any of the foregoing embodiments, at least one of $R^{3a}$, $R^{3b}$, $R^{4a}$ or $R^{4b}$ is H. In some embodiments, each of $R^{3a}$, $R^{3b}$, $R^{4a}$ and $R^{4b}$ are H.

In some embodiments, $R^{3a}$ is —OH, —$NH_2$, —$CO_2H$, halo, cyano, hydroxylalkyl, aminoalkyl, cyanoalkyl, carboxyalkyl or aminocarbonyl, and $R^{3b}$, $R^{4a}$ and $R^{4b}$ are H.

In other embodiments, $R^{4a}$ is —OH, —$NH_2$, —$CO_2H$, halo, cyano, hydroxylalkyl, aminoalkyl, cyanoalkyl, carboxyalkyl or aminocarbonyl, and $R^{3a}$, $R^{3b}$ and $R^{4b}$ are H.

In other embodiments, $R^{3a}$ is H, —OH, —$NH_2$, —$CO_2H$, halo, cyano, hydroxylalkyl, aminoalkyl, cyanoalkyl, carboxyalkyl or aminocarbonyl, and $R^{3b}$ joins with $R^{4b}$ to form a carbocyclic or heterocyclic ring;

In still more embodiments, $R^{4a}$ is H, —OH, —$NH_2$, —$CO_2H$, halo, cyano, hydroxylalkyl, aminoalkyl, cyanoalkyl, carboxyalkyl or aminocarbonyl, and $R^{4b}$ joins with $R^{3b}$ to form a carbocyclic or heterocyclic ring.

In other embodiments, $R^{3a}$ and $R^{3b}$ join to form a carbocyclic or heterocyclic ring. In other embodiments, $R^{4a}$ and $R^{4b}$ join to form a carbocyclic or heterocyclic ring. In other embodiments, $R^{3a}$ and $R^{3b}$ join to form oxo. In other embodiments, $R^{4a}$ and $R^{4b}$ join to form oxo.

In still other embodiments, $R^{3a}$ or $R^{4a}$ is aminocarbonyl. For example, in certain embodiments, the amino carbonyl is

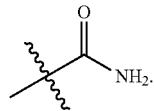

In other embodiments, $R^{3a}$ or $R^{4a}$ is cyano. In other embodiments, $R^{3a}$ or $R^{4a}$ is —OH. In other embodiments, $R^{3a}$ or $R^{4a}$ is hydroxylalkyl, for example hydroxylmethyl.

In some of the foregoing embodiments, X is N. In other of the foregoing embodiments, Z is N. In still more embodiments, X is N and Z is N.

In some embodiments, Z is N and Y is N. In other embodiments, X is N, Z is N, Y is $CR^6$, wherein $R^6$ is H and W is $CR^6$, wherein $R^6$ is a bond to $L^1$. In different embodiments, Z is N and Y is $CR^6$, wherein $R^6$ is H, W is $CR^6$, wherein $R^6$ is a bond to $L^1$ and X is $CR^6$, wherein $R^6$ is cyano, methoxy or amino.

In other embodiments, Z is N, X is $CR^6$ and $R^6$ is cyano, Y is $CR^6$, wherein $R^6$ is H and W is $CR^6$, wherein $R^6$ is a bond to $L^1$.

In other embodiments, Y is N, Z is N, W is $CR^6$, wherein $R^6$ is a bond to $L^1$ and X is $CR^6$, wherein $R^6$ is H.

In other of the foregoing embodiments, Z is a bond.

In certain embodiments, Y is $NR^5$. In some of these embodiments, $R^5$ is $C_1$-$C_6$alkyl. In other embodiments, $R^5$ is H.

In still other embodiments, X or Y is $CR^6$. In some of these embodiments, $R^6$ is, at each occurrence, independently H, cyano, amino, $C_1$-$C_6$alkoxy or a bond to $L^1$. In some other of these embodiments, $R^6$ is H. In other embodiments, $R^6$ is $C_1$-$C_6$alkoxy. In other embodiments, $R^6$ is cyano. In more embodiments, $R^6$ is methoxy. In other embodiments, $R^6$ is amino.

In various different embodiments, the compound has one of the structures set forth in Table 1 or Table 2 below:

TABLE 1

| Compound Number | Structure | Mass Characterization |
|---|---|---|
| 1 | 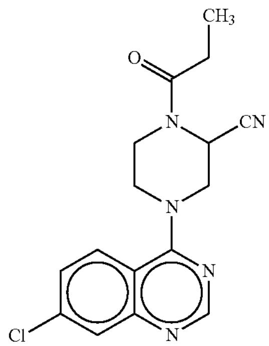 | 330.2 [M + H]+ |
| 2 | 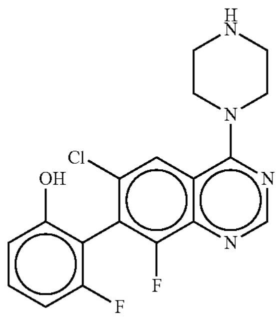 | 377 [M + H]+ |
| 3 | 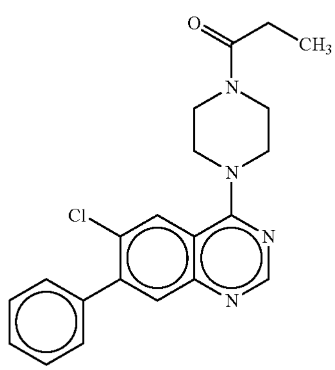 | 381.2 [M + H]+ |
| 4 | 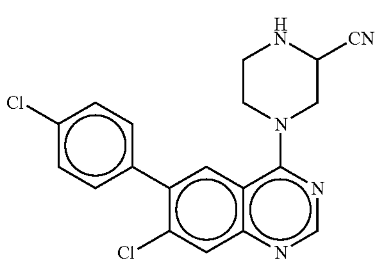 | 384.2 [M + H]+ |
| 5 | 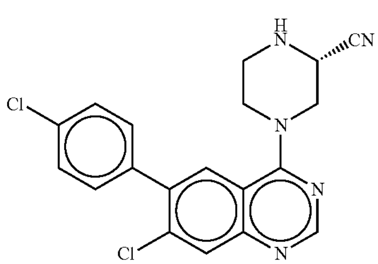 | 384.2 [M + H]+ |

TABLE 1-continued
| Compound Number | Structure | Mass Characterization |
|---|---|---|
| 6 | 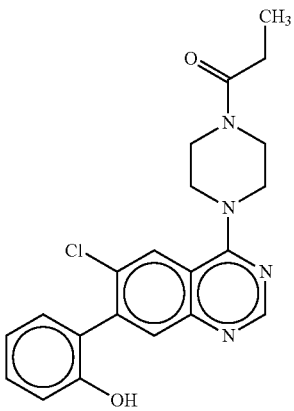 | 397.15 [M + H]+ |
| 7 | 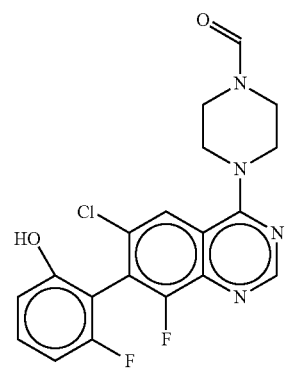 | 405.1 [M + H]+ |
| 8 | 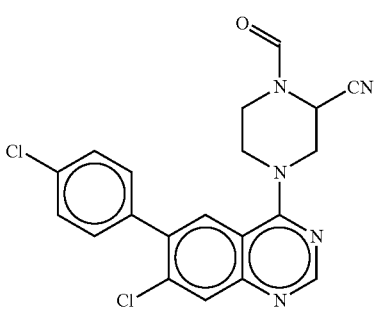 | 412.25 [M + H]+ |
| 9 | 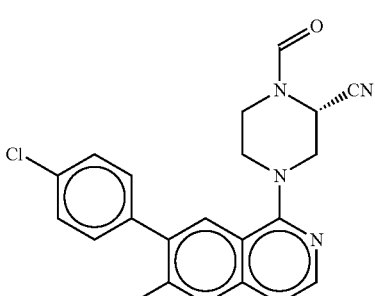 | 412.2 [M + H]+ |

TABLE 1-continued

| Compound Number | Structure | Mass Characterization |
|---|---|---|
| 10 | 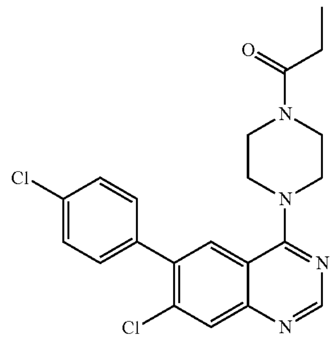 [SMILES: CCC(=O)N1CCN(c2ncnc3cc(Cl)c(-c4ccc(Cl)cc4)cc23)CC1] | 415.3 [M + H]+ |
| 11 | 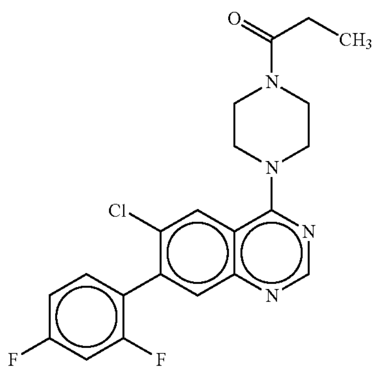 | 417.1 [M + H]+ |
| 12 | 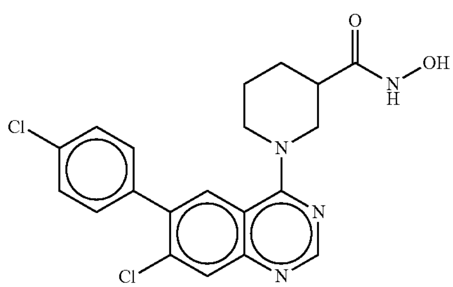 | 417.25 [M + H]+ |
| 13 | 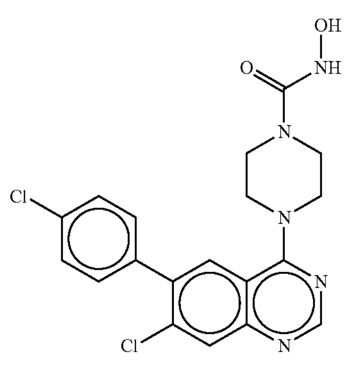 | 418.2 [M + H]+ |

TABLE 1-continued
| Compound Number | Structure | Mass Characterization |
|---|---|---|
| 14 | 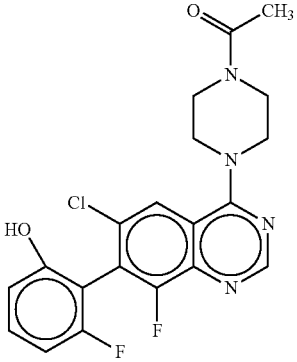 | 419.15 [M + H]+ |
| 15 | 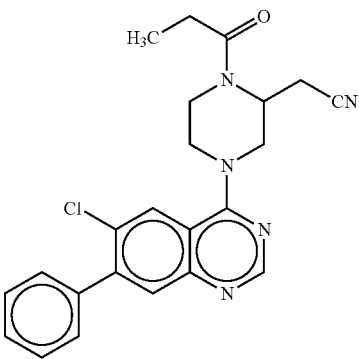 | 420.3 [M + H]+ |
| 16 | 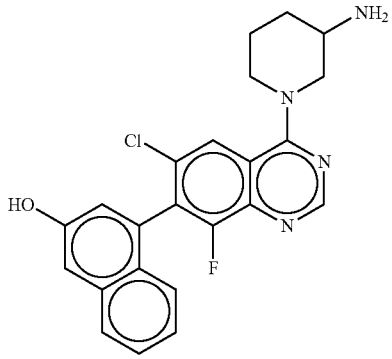 | 423.1 [M + H]+ |
| 17 | 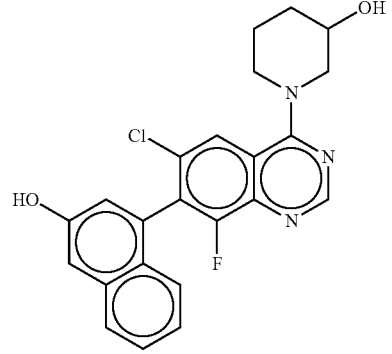 | 424.15 [M + H]+ |

TABLE 1-continued

| Compound Number | Structure | Mass Characterization |
|---|---|---|
| 18 | 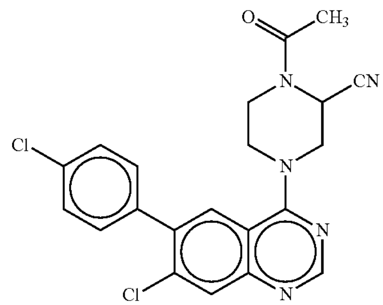 | 426.25 [M + H]+ |
| 19 | 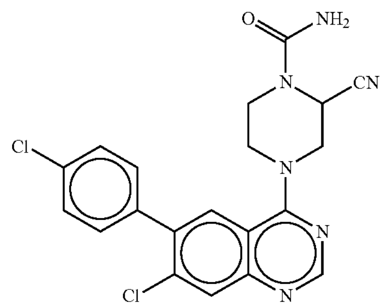 | 427.3 [M + H]+ |
| 20 | 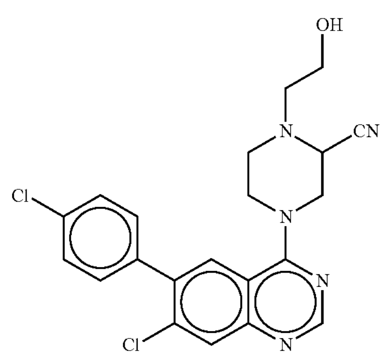 | 429.3 [M + H]+ |
| 21 | 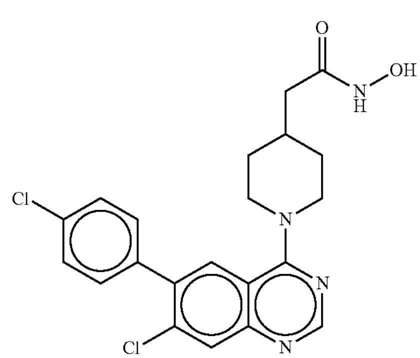 | 431.3 [M + H]+ |

TABLE 1-continued
| Compound Number | Structure | Mass Characterization |
|---|---|---|
| 22 | 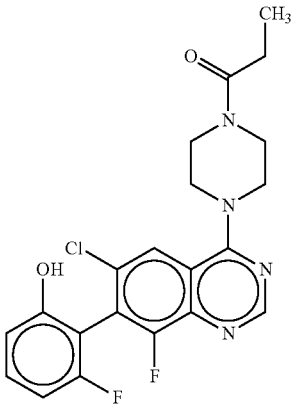 | 433.1 [M + H]+ |
| 23 | 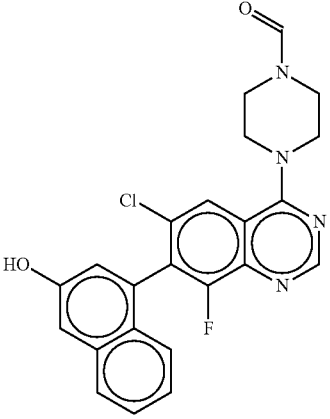 | 437.1 [M + H]+ |
| 24 | 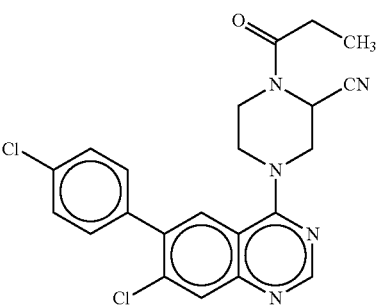 | 440.35 [M + H]+ |
| 25 | 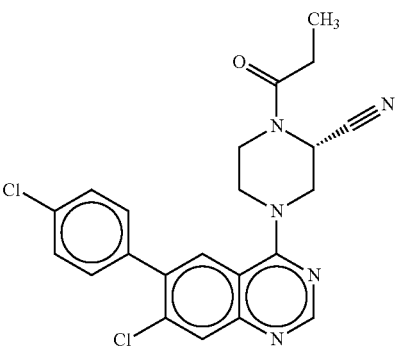 | 440.3 [M + H]+ |

TABLE 1-continued
| Compound Number | Structure | Mass Characterization |
|---|---|---|
| 26 | 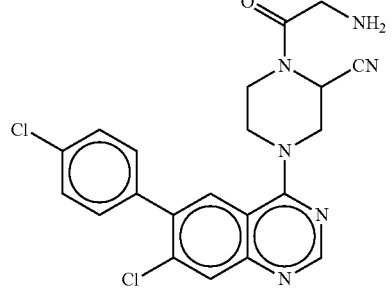 | 441.3 [M + H]+ |
| 27 | 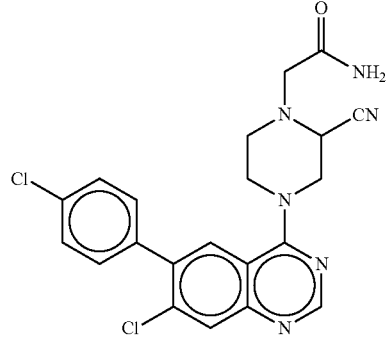 | 441.3 [M + H]+ |
| 28 | 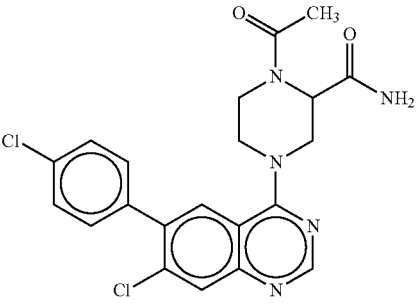 | 444.3 [M + H]+ |
| 29 | 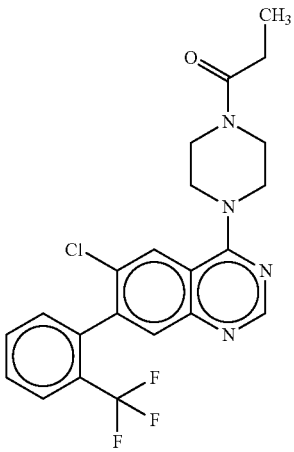 | 519.1 [M + H]+ |

TABLE 1-continued
| Compound Number | Structure | Mass Characterization |
|---|---|---|
| 30 | 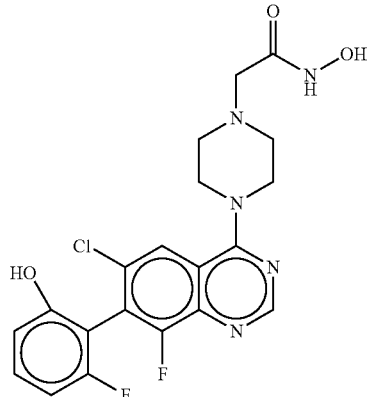 | 450.15 [M + H]+ |
| 31 | 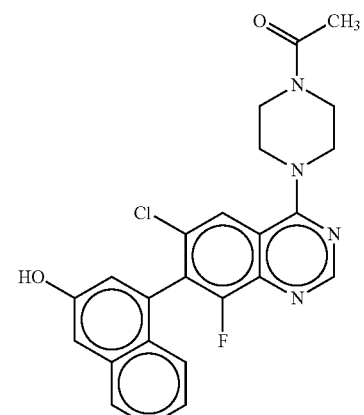 | 451.15 [M + H]+ |
| 32 | 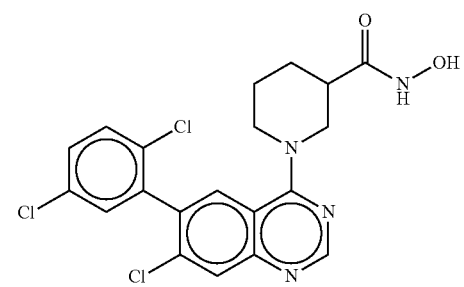 | 453.2 [M + H]+ |
| 33 | 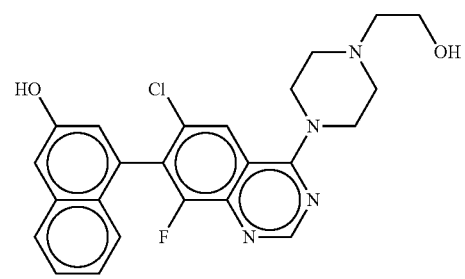 | 453.15 [M + H]+ |

TABLE 1-continued

| Compound Number | Structure | Mass Characterization |
|---|---|---|
| 34 | 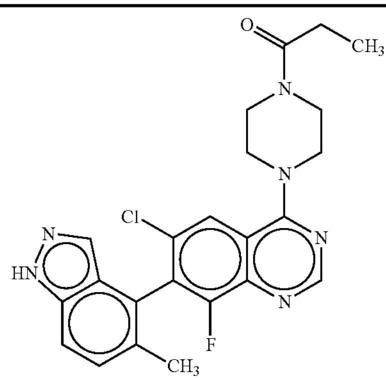 | 453.15 [M + H]+ |
| 35 | 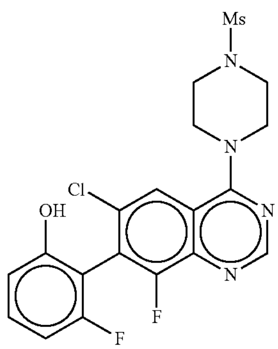 | 455 [M + H]+ |
| 36 | 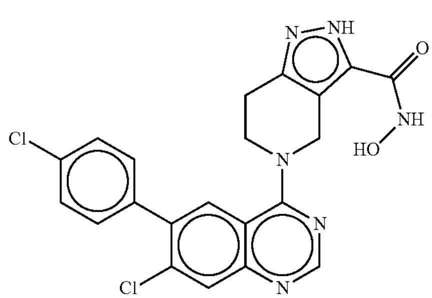 | 453.35 [M − H]− |
| 37 | 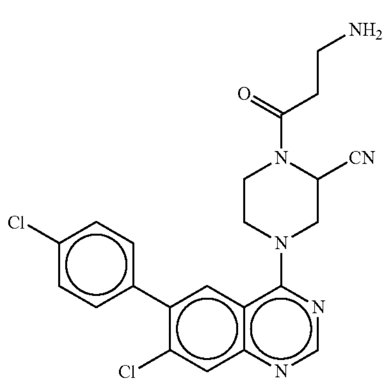 | 455.35 [M + H]+ |

TABLE 1-continued

| Compound Number | Structure | Mass Characterization |
|---|---|---|
| 38 | 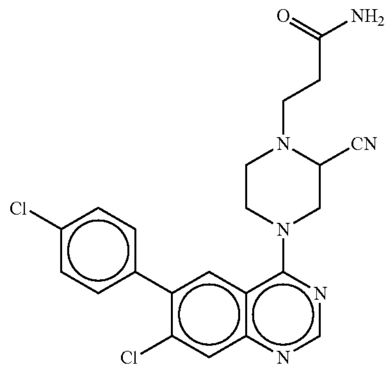 | 455.3 [M + H]+ |
| 39 | 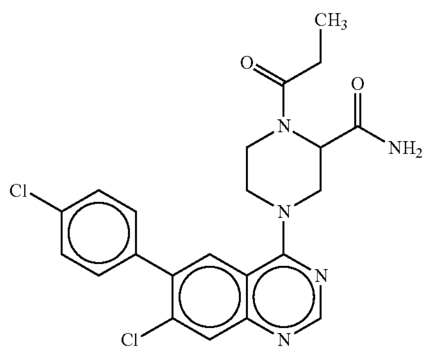 | 458.4 [M + H]+ |
| 40 | 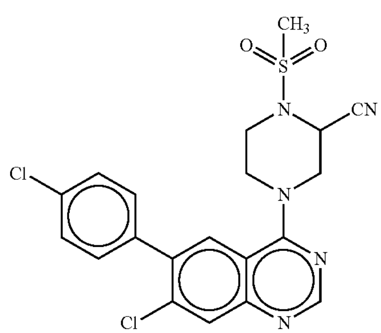 | 462.3 [M + H]+ |
| 41 | 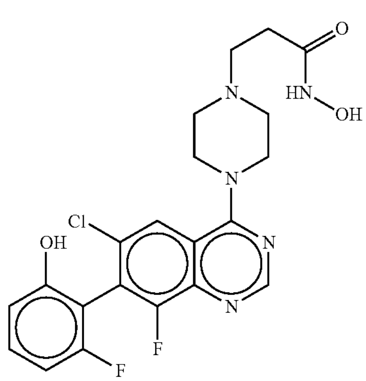 | 464.15 [M + H]+ |

TABLE 1-continued
| Compound Number | Structure | Mass Characterization |
|---|---|---|
| 42 | 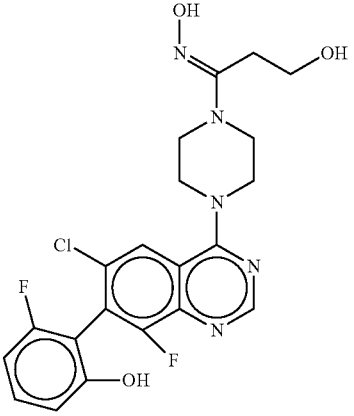 | 464.1 [M + H]+ |
| 43 | 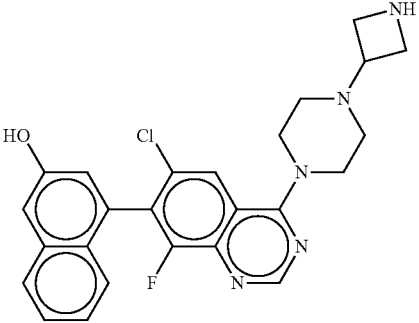 | 464.25 [M + H]+ |
| 44 | 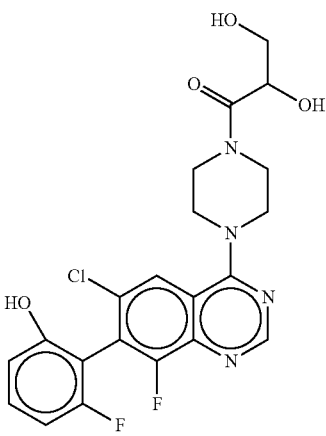 | 465.1 [M + H]+ |

TABLE 1-continued
| Compound Number | Structure | Mass Characterization |
|---|---|---|
| 45 | 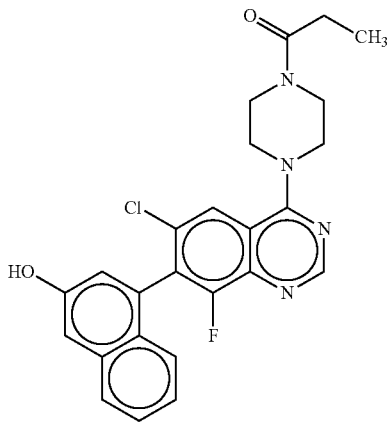 | 465.15 [M + H]+ |
| 46 | 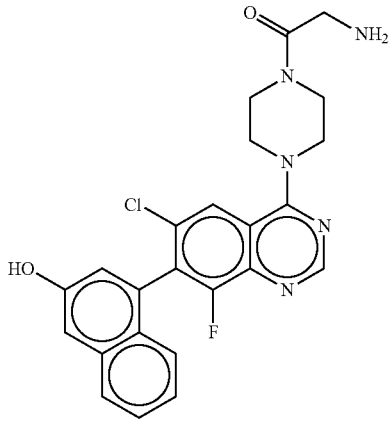 | 466.2 [M + H]+ |
| 47 | 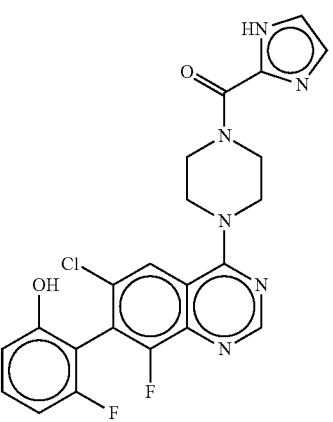 | 471.15 [M + H]+ |

TABLE 1-continued

| Compound Number | Structure | Mass Characterization |
|---|---|---|
| 48 | 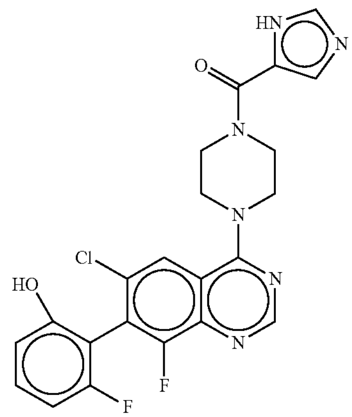 | 471.1 [M + H]+ |
| 49 | 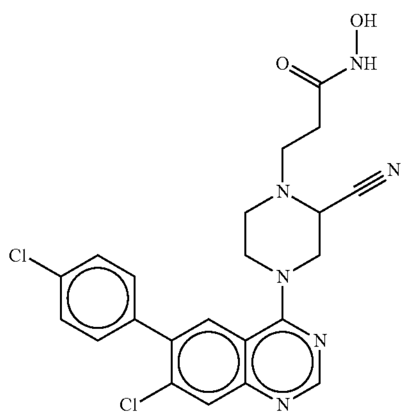 | 471.35 [M + H]+ |
| 50 | 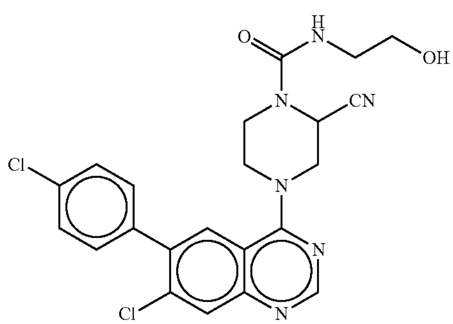 | 471.3 [M + H]+ |
| 51 | 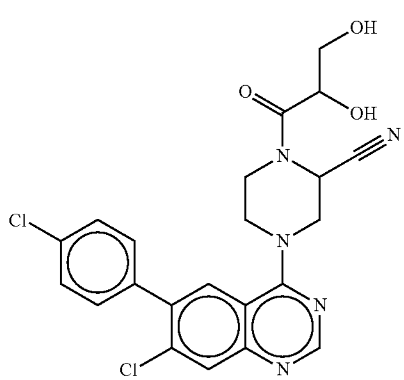 | 472.35 [M + H]+ |

TABLE 1-continued
| Compound Number | Structure | Mass Characterization |
|---|---|---|
| 52 | 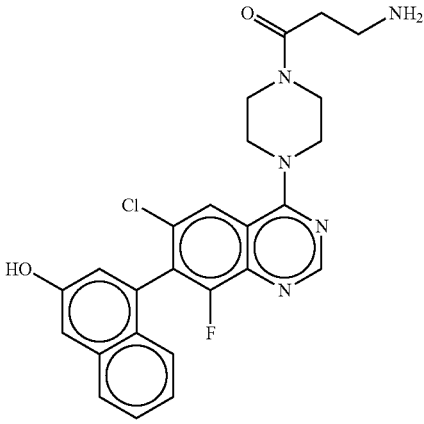 | 480.2 [M + H]+ |
| 53 | 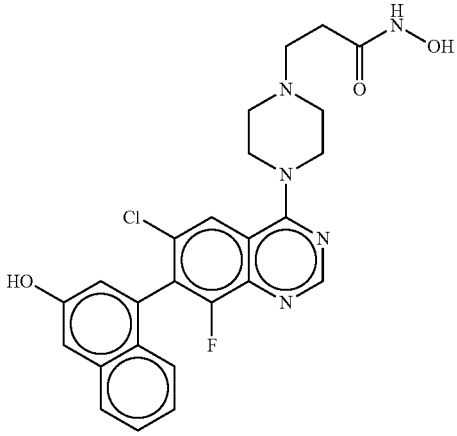 | 496.2 [M + H]+ |
| 54 | 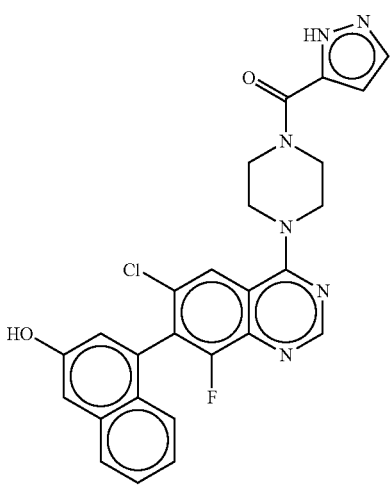 | 503.2 [M + H]+ |

TABLE 1-continued
| Compound Number | Structure | Mass Characterization |
|---|---|---|
| 55 | 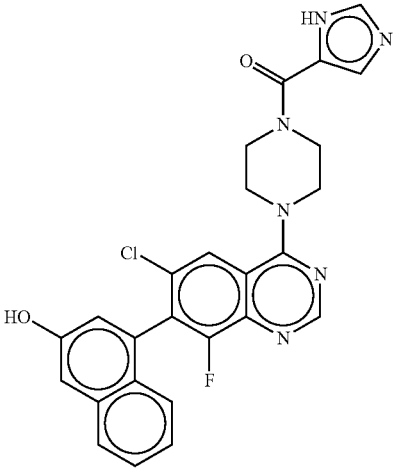 | 503.2 [M + H]+ |
| 56 | 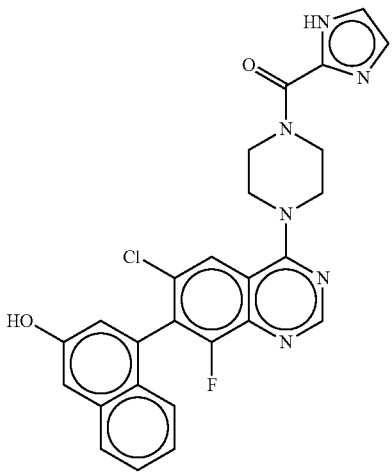 | 503.25 [M + H]+ |
| 57 | 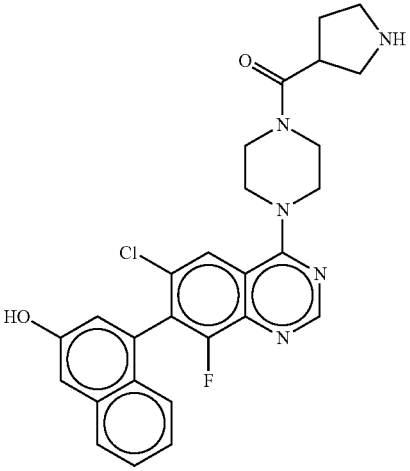 | 506.15 [M + H]+ |

TABLE 1-continued

| Compound Number | Structure | Mass Characterization |
|---|---|---|
| 58 | 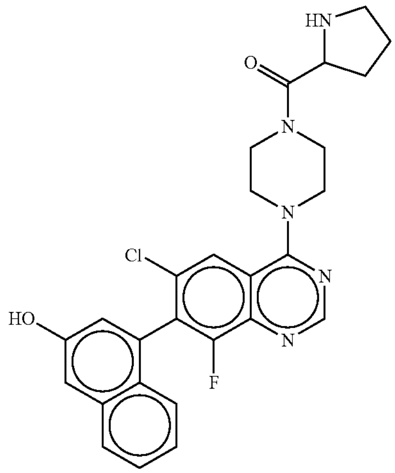 | 506.25 [M + H]+ |
| 59 | 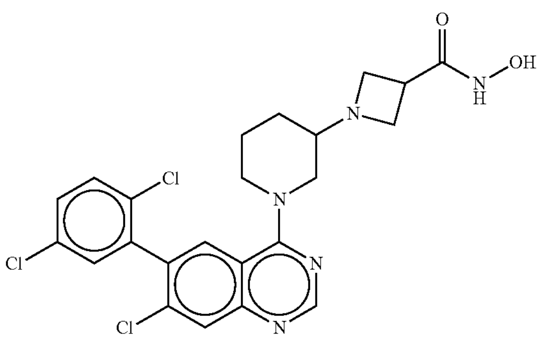 | 507.3 [M + H]+ |
| 60 | 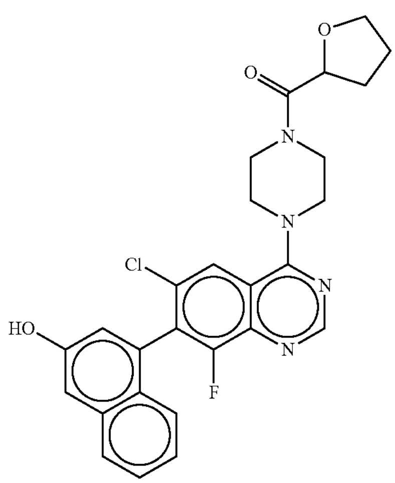 | 507.25 [M + H]+ |

TABLE 1-continued
| Compound Number | Structure | Mass Characterization |
|---|---|---|
| 61 | 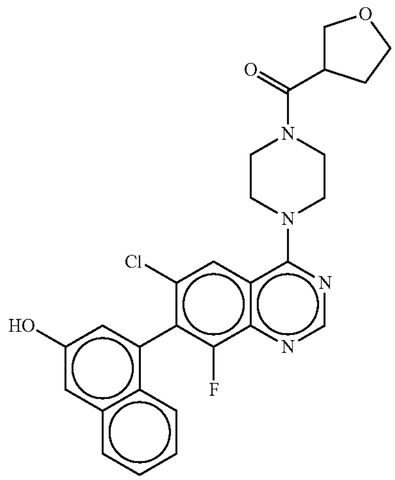 | 507.2 [M + H]+ |
TABLE 2
| Compound Number | Structure | Mass Characterization |
|---|---|---|
| 62 | 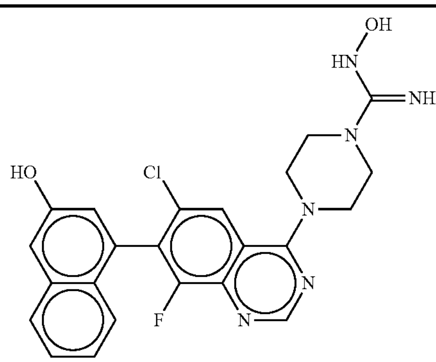 | 467.20 [M + H]+ |
| 63 | 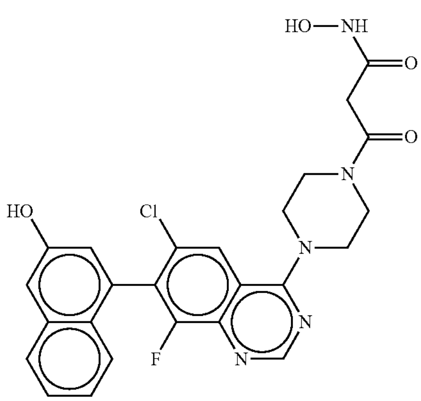 | 510.25 [M + H]+ |
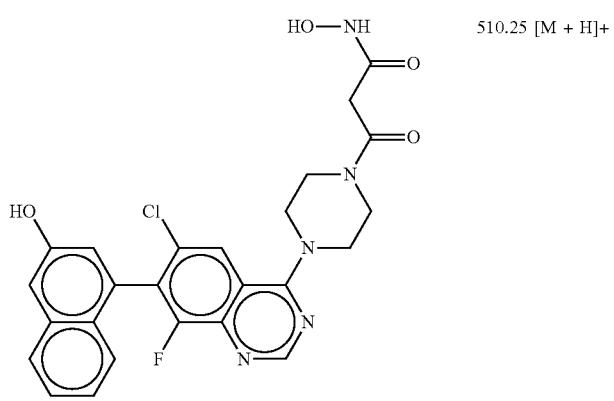

TABLE 2-continued
| Compound Number | Structure | Mass Characterization |
|---|---|---|
| 64 | 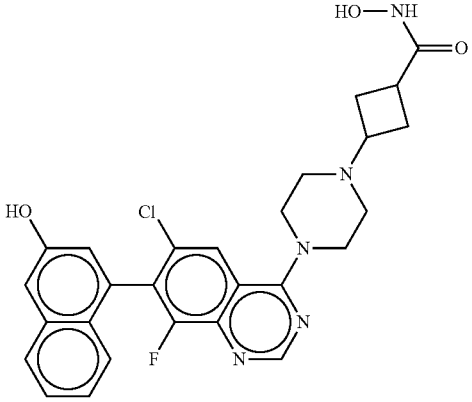 | 522.30 [M + H]+ |
| 65 | 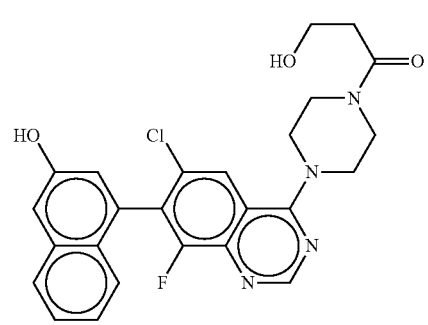 | 481.20 [M + H]+ |
| 66 | 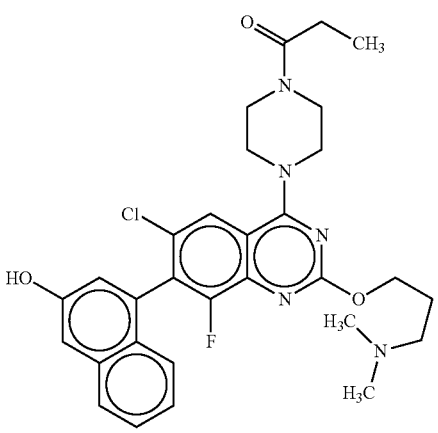 | 566.30 [M + H]+ |
| 67 | 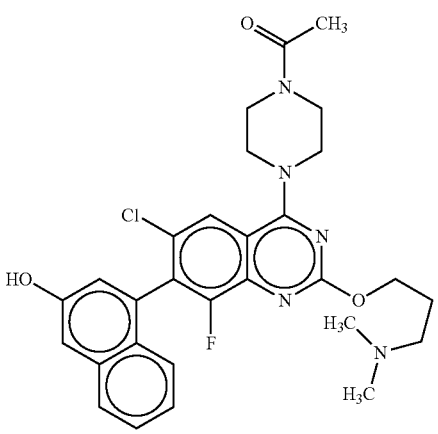 | 552.30 [M + H]+ |

TABLE 2-continued
| Compound Number | Structure | Mass Characterization |
|---|---|---|
| 68 | 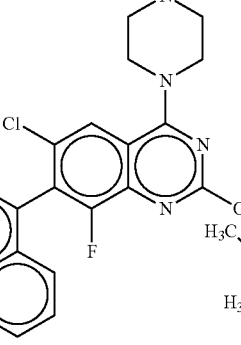 | 538.30 [M + H]+ |
| 69 | 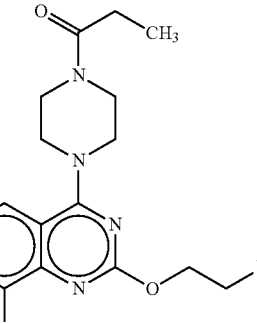 | 562.2 [M + H]+ |
| 70 | 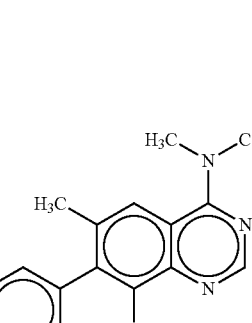 | 368.10 [M + Na]+ |
| 71 | 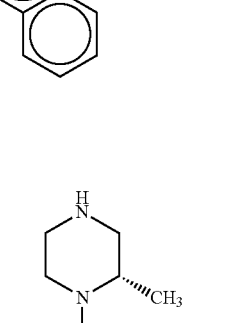 | 513.30 [M + H]+ |

TABLE 2-continued

| Compound Number | Structure | Mass Characterization |
|---|---|---|
| 72 | (structure) | 527.10 [M + H]+ |

Synthesis of Compounds

The compounds in Table 1 and Table 2 were each prepared according to the indicated method and analyzed by mass spectrometry and/or $^1$H NMR. Experimental mass spectrometry data is included in Table 1 and Table 2 above. Exemplary synthetic procedures are described in more detail below and in the Examples.

It is understood that in the present description, combinations of substituents and/or variables of the depicted formulae are permissible only if such contributions result in stable compounds.

It will also be appreciated by those skilled in the art that in the processes for preparing the compounds described herein the functional groups of intermediate compounds may need to be protected by suitable protecting groups. Such functional groups include, but are not limited to, hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups are optionally added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

The following General Reaction Schemes illustrate exemplary methods of making compounds of compounds of structure (I):

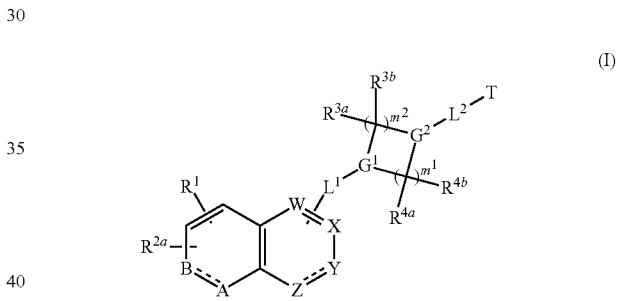

(I)

or a pharmaceutically acceptable salt, tautomer or stereoisomer thereof, wherein $R^1$, $R^{2a}$, $R^{3a}$, $R^{3b}$, $R^{4a}$, $R^{4b}$, $G^1$, $G^2$, $L^1$, $L^2$, $m^1$, $m^2$, A, B, W, X, Y, Z and T are as defined above. For ease of illustration, many of the schemes which follow illustrate an "$R^2$" moiety. The $R^2$ moiety is meant to include any one of $R^{2a}$, $R^{2b}$ or $R^{2c}$. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

General Reaction Scheme 1

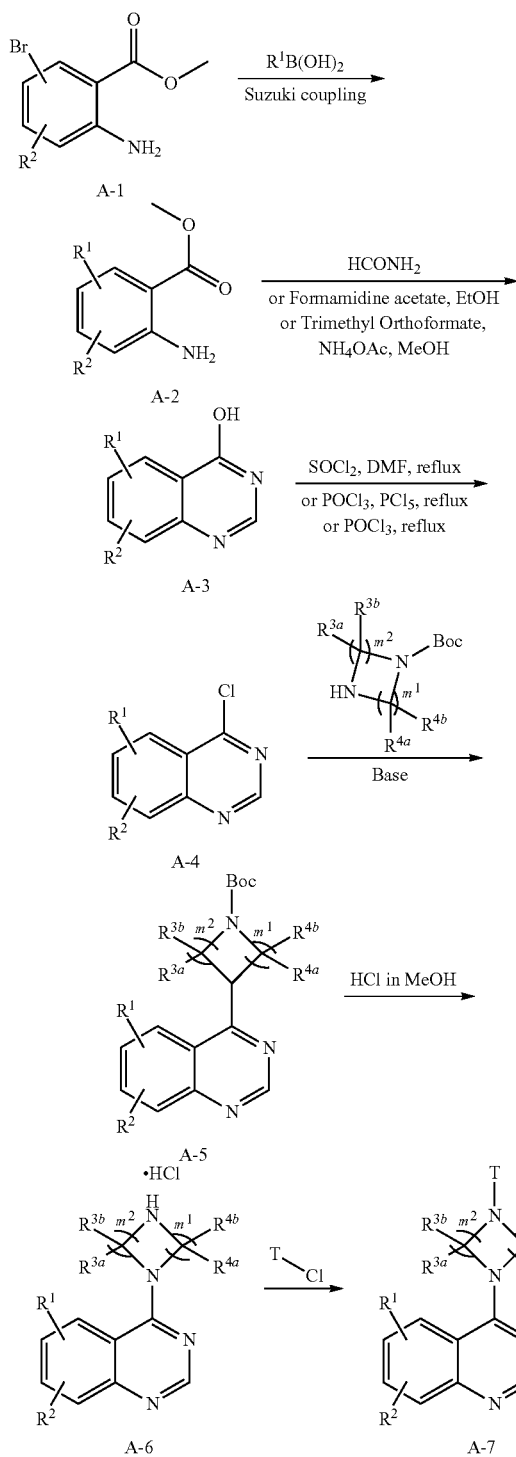

Reaction of compounds of structure A-2 with formamide or other suitable reagents, such as formamidine acetate or trimethyl orthoformate, yields quinazolines of structure A-3. A-3 is chlorinated under appropriate conditions (e.g., $SOCl_2$, $POCl_3/PCl_5$ or $POCl_3$) to yield chloroquinazoline A-4. Reaction of A-4 with an appropriately protected heterocycle under basic conditions yields A-5. Appropriate protecting groups include butyloxycarbonyl (BOC) as depicted in General reaction Scheme 1, as well as other protecting groups known in the art. Deprotection of A-5 followed by acylation with an acid chloride (or sulfonyl chloride) or acid and appropriate activating reagents yields A-7.

General Reaction Scheme 2

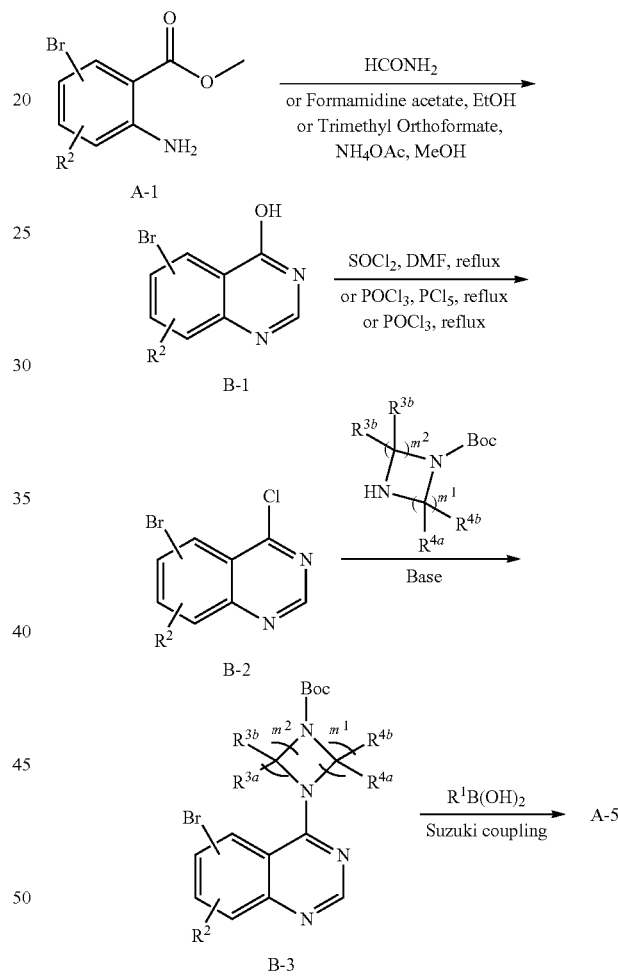

Embodiments of the compound of structure (I) (e.g., compound A-7) can be prepared according to General Reaction Scheme 1 ("Method A"), wherein $R^1$, $R^2$, $R^{3a}$, $R^{4a}$, $R^{4b}$, T, $m^1$ and $m^2$ are as defined herein above. As shown in General Reaction Scheme 1, compounds of structure A-1 can be purchased from commercial sources or prepared according to methods familiar to one of ordinary skill in the art. Reaction of A-1 under Suzuki conditions yields A-2.

Alternatively, embodiments of the compound of structure (I) (e.g., compound A-7) can be prepared according to General Reaction Scheme 2 ("Method B"), wherein $R^1$, $R^2$, $R^{3a}$, $R^{3b}$, $R^{4a}$, $R^{4b}$, T, $m^1$ and $m^2$ are as defined herein above. Compounds of structure A-1 are prepared or purchased as described above. Treatment of A-1 with formamide or other suitable reagents, such as formamidine acetate or trimethyl orthoformate, yields quinazolines of structure B-1. B-1 can then be chlorinated to yield B-2 and reacted with an appropriately protected heterocycle under basic conditions to yield B-3 as described above for Method A. Suzuki coupling then yields A-5 which can be converted to A-7 as described in Method A above.

General Reaction Scheme 3

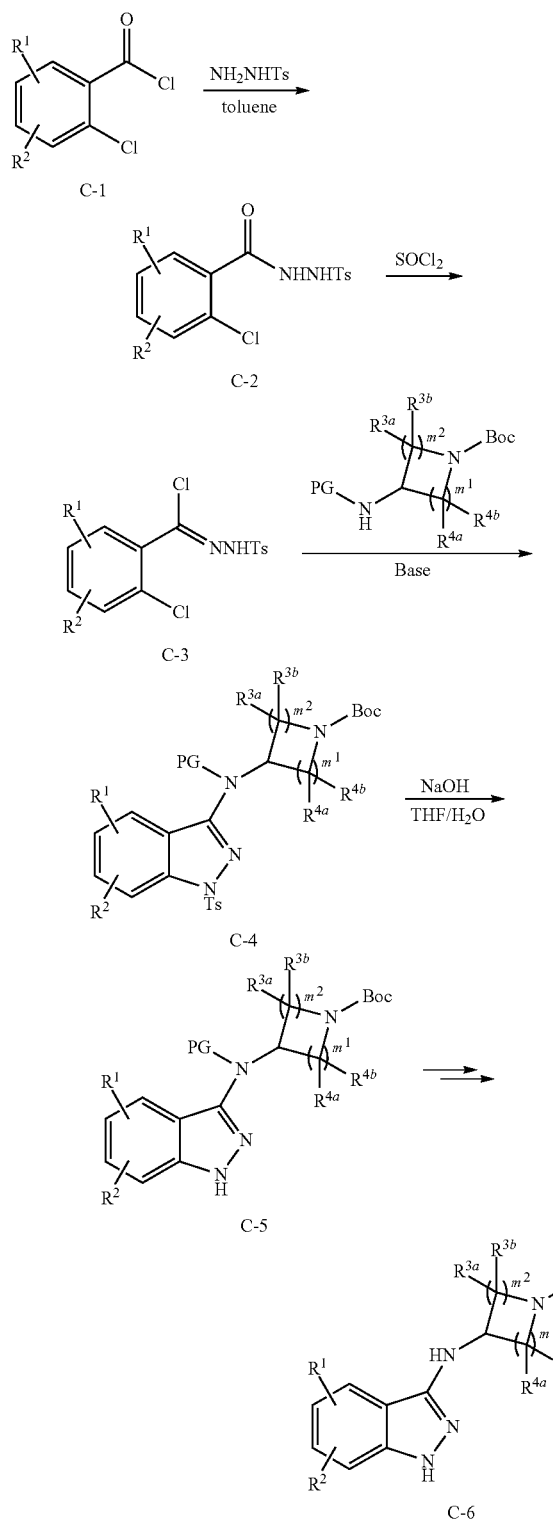

Other embodiments of the compound of structure (I) (e.g., compound C-6) can be prepared according to General Reaction Scheme 3 ("Method C"), wherein $R^1$, $R^2$, $R^{3a}$, $R^{3b}$, $R^{4a}$, $R^{4b}$, T, $m^1$ and $m^2$ are as defined herein above. As shown in General Reaction Scheme 3, compounds of structure C-1, which can be purchased from commercial sources or pre- pared according to well-known procedures, are reacted with tosyl hydrazine to yield C-2. Chlorination of C-2 with an appropriate reagent(s), such as thionyl chloride, then yields C-3 which can be reacted under basic conditions with an appropriately protected heterocycle (PG=protecting group or $C_1$-$C_6$alkyl) to yield indazole C-4. The tosyl group is removed from C-4 by treatment with sodium hydroxide in THF/$H_2O$ to yield C-5. Removal of the nitrogen protecting group and acylation or thioacylation as described in Method A then yields the desired compound C-6.

General Reaction Scheme 4

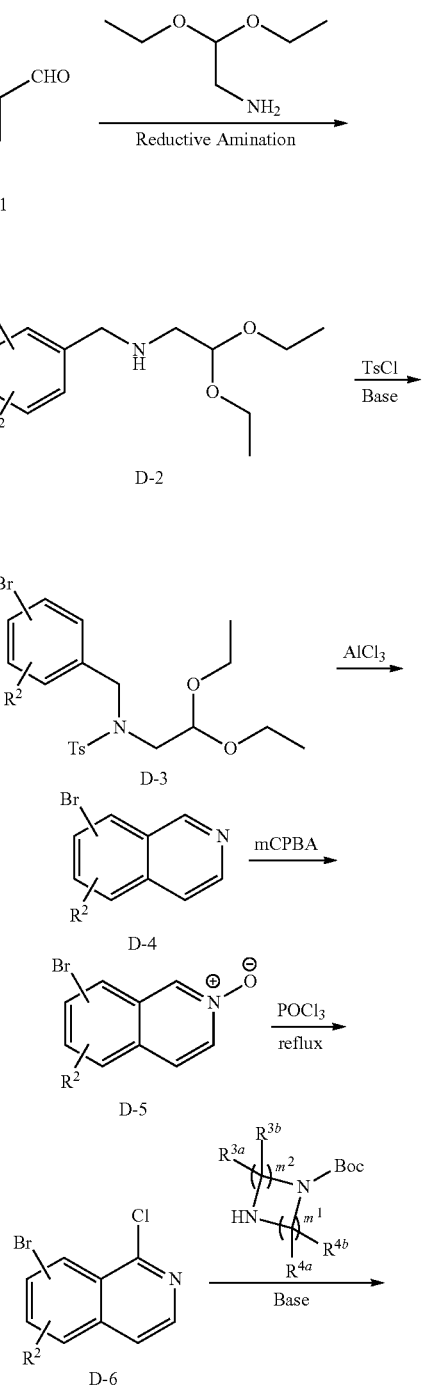

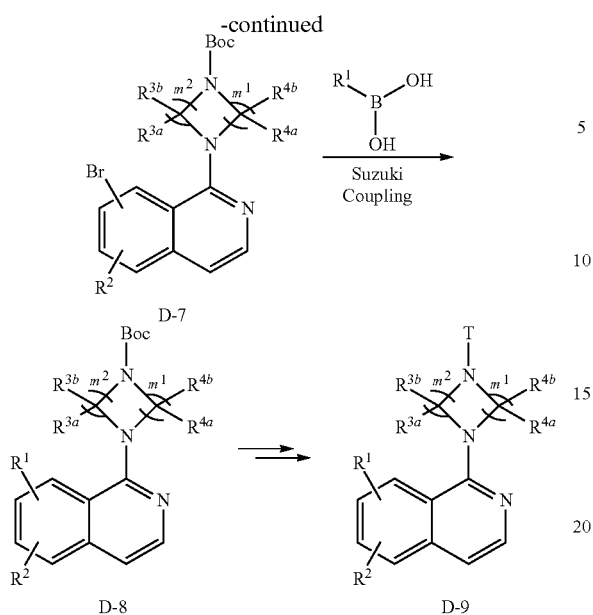
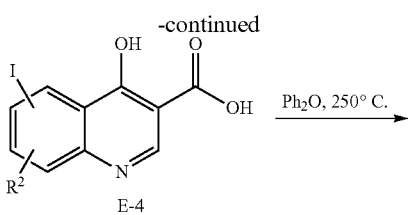
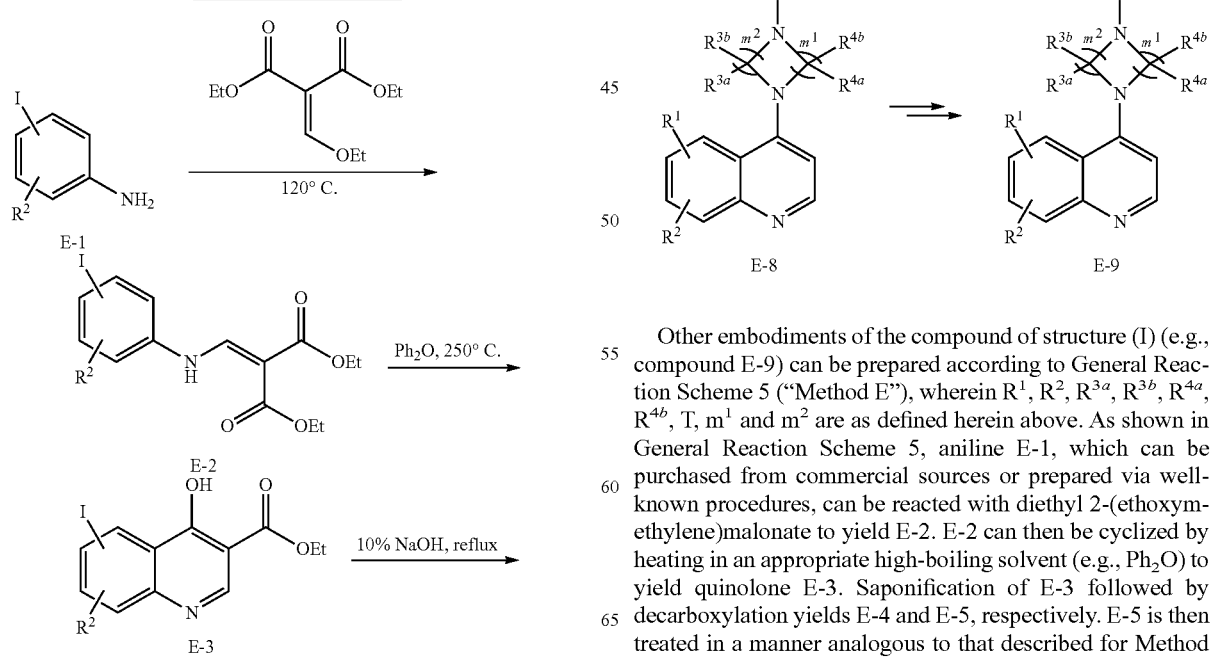

Other embodiments of the compound of structure (I) (e.g., compound D-9) can be prepared according to General Reaction Scheme 4 ("Method D"), wherein $R^1$, $R^2$, $R^{3a}$, $R^{3b}$, $R^{4a}$, $R^{4b}$, T, $m^1$ and $m^2$ are as defined herein above. As shown in General Reaction Scheme 4, benzaldehyde D-1 is treated under reductive amination conditions to yield D-2. Formation of the tosyl-protected amine (D-3) followed by treatment with an appropriate Lewis acid (e.g., $AlCl_3$) yields isoquinoline D-4. Oxidation of D-4 with meta-chloroperbenzoic acid (mCPBA) yields D-5 which can be chlorinated by treatment with an appropriate reagent, such as $POCl_3$. Chloride D-6 is then treated in a manner analogous to that described for Method B to yield D-9.

Other embodiments of the compound of structure (I) (e.g., compound E-9) can be prepared according to General Reaction Scheme 5 ("Method E"), wherein $R^1$, $R^2$, $R^{3a}$, $R^{3b}$, $R^{4a}$, $R^{4b}$, T, $m^1$ and $m^2$ are as defined herein above. As shown in General Reaction Scheme 5, aniline E-1, which can be purchased from commercial sources or prepared via well-known procedures, can be reacted with diethyl 2-(ethoxymethylene)malonate to yield E-2. E-2 can then be cyclized by heating in an appropriate high-boiling solvent (e.g., $Ph_2O$) to yield quinolone E-3. Saponification of E-3 followed by decarboxylation yields E-4 and E-5, respectively. E-5 is then treated in a manner analogous to that described for Method B to yield E-9.

General Reaction Scheme 6

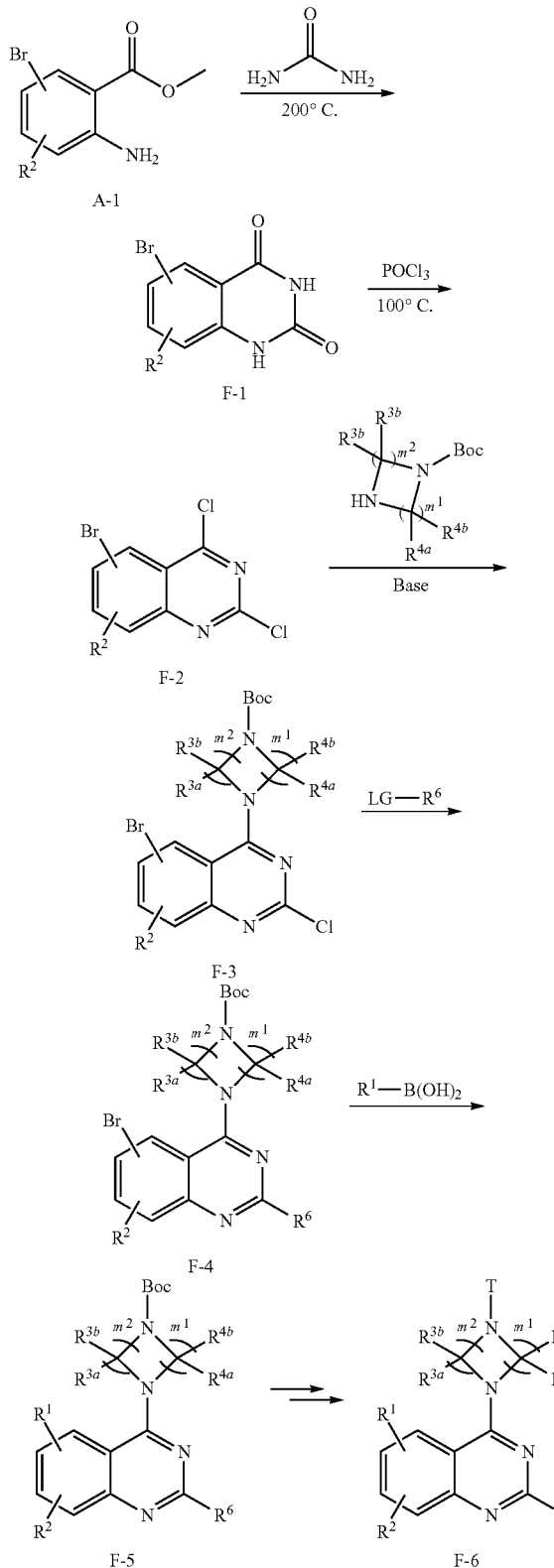

General Reaction Scheme 7

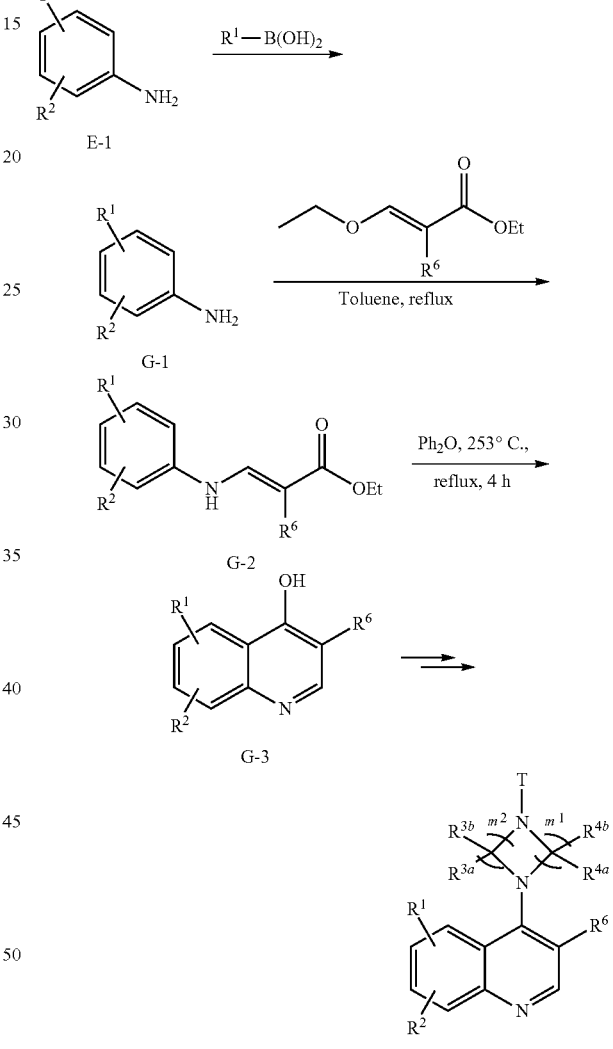

$R^{4b}$, T, $m^1$ and $m^2$ are as defined herein above. As shown in General Reaction Scheme 6, A-1 is cyclized to quinazolinedione F-1 by treatment with urea. Chlorination of F-1 by treatment with $POCl_3$ followed by reaction with a protected heterocycle yield F-2 and F-3, respectively. The $R^6$ substituent is installed by $S_NAr$ reaction of G-3 with LG-R6, wherein LG is an appropriate leaving group. For example, where $R^6$ is cyano or alkoxy, LG is sodium or another appropriate action. The general procedures described above with respect to Method B can then be employed to yield F-6.

Other embodiments of the compound of structure (I) (e.g., compound F-6) can be prepared according to General Reaction Scheme 6 ("Method F"), wherein $R^1$, $R^2$, $R^{3a}$, $R^{3b}$, $R^{4a}$, Other embodiments of the compound of structure (I) (e.g., compound G-4) can be prepared according to General Reaction Scheme 7 ("Method G"), wherein $R^1$, $R^2$, $R^{3a}$, $R^{3b}$, $R^{4a}$, $R^{4b}$, T, $m^1$ and $m^2$ are as defined herein above. As shown in General Reaction Scheme 7, aniline E-1 is treated under Suzuki conditions to install the R-1 substituent. G-1 is then heated in toluene with an appropriately substituted unsaturated ester to yield G-2. Cyclization of G-2 to hydroxyquinoline G-3 is accomplished by heating in a high boiling solvent (e.g., $Ph_2O$) for an appropriate amount of time. Following the general procedures outlined in Method A then yields G-4.

General Reaction Scheme 8

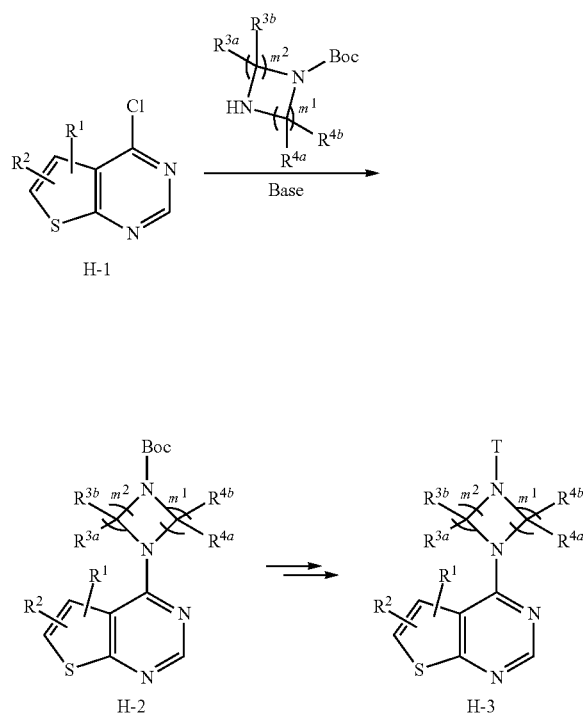

Other embodiments of the compound of structure (I) (e.g., compound H-3) can be prepared according to General Reaction Scheme 8 ("Method H"), wherein $R^1$, $R^2$, $R^{3a}$, $R^{3b}$, $R^{4a}$, $R^{4b}$, T, $m^1$ and $m^2$ are as defined herein above. Referring to General Reaction Scheme 8, thienopyrimidine H-1 can be prepared according to well-known procedures or purchased from commercial sources. H-1 is treated with an appropriately protected heterocycle under basic conditions to yield H-2. Deprotection followed by acylation or thioacylation according to the procedures described above then yields H-3.

General Reaction Scheme 9

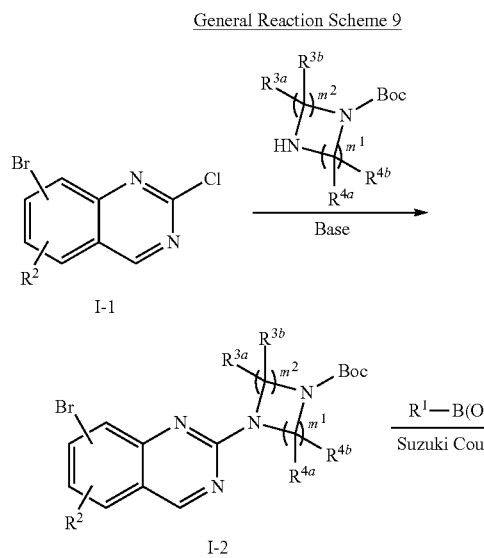

Other embodiments of the compound of structure (I) (e.g., compound I-4) can be prepared according to General Reaction Scheme 9 ("Method I"), wherein $R^1$, $R^2$, $R^{3a}$, $R^{3b}$, $R^{4a}$, $R^{4b}$, T, $m^1$ and $m^2$ are as defined herein above. Referring to General Reaction Scheme 9, quinazoline I-1 can be prepared according to well-known procedures or purchased from commercial sources. I-1 is treated with an appropriately protected heterocycle under basic conditions to yield I-2. Suzuki reaction of I-2 with an appropriate reagent to install the $R^1$ moiety results in I-3. I-3 is then deprotected and acylated (or thioacylated) according to the procedures described above to yield I-4.

General Reaction Scheme 10

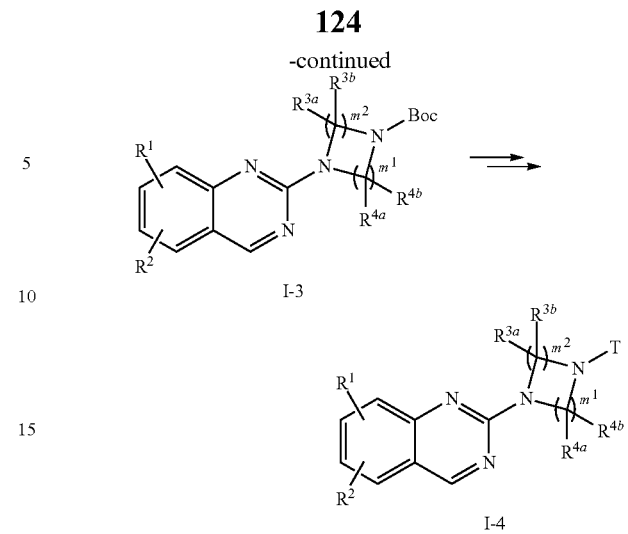

125

-continued

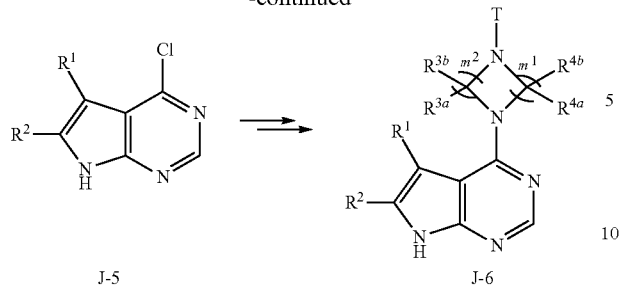

J-5 → J-6

Other embodiments of the compound of structure (I) (e.g., compound J-6) can be prepared according to General Reaction Scheme 10 ("Method J"), wherein $R^1$, $R^2$, $R^{3a}$, $R^{3b}$, $R^{4a}$, $R^{4b}$, T, $m^1$ and $m^2$ are as defined herein above. Referring to General Reaction Scheme 10, pyrrolopyrimidinone J-1 can be prepared according to well-known procedures or purchased from commercial sources. J-1 is chlorinated with an appropriate reagent (e.g., $POCl_3$) to yield J-2 which is then iodinated with an appropriate reagent, such as N-iodosuccinimide (NIS) to yield J-3. Protection of J-3 followed by Suzuki reaction yields J-5. J-5 is then treated according to the procedures described above to yield J-6.

General Reaction Scheme 11

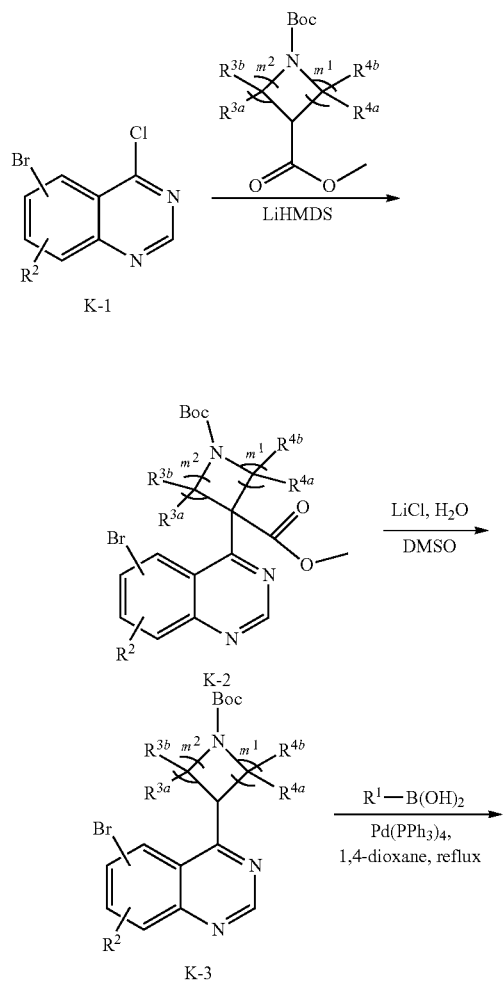

126

-continued

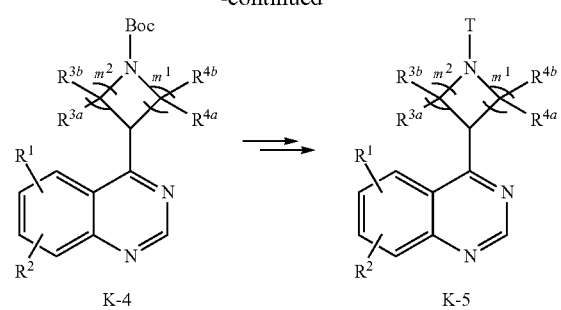

K-4 → K-5

Other embodiments of the compound of structure (I) (e.g., compound K-5) can be prepared according to General Reaction Scheme 11 ("Method K"), wherein $R^1$, $R^2$, $R^{3a}$, $R^{3b}$, $R^{4a}$, $R^{4b}$, T, $m^1$ and $m^2$ are as defined herein above. Referring to General Reaction Scheme 11, quinazoline K-1 can be prepared according to well-known procedures or purchased from commercial sources. K-1 is reacted with an appropriate ester under basic conditions to form the requisite carbon-carbon bond. K-2 is then decarboxylated to yield K-3. Suzuki reaction, deprotection and acylation or thioacylation are then carried out as described in the above schemes to yield K-5.

General Reaction Scheme 12

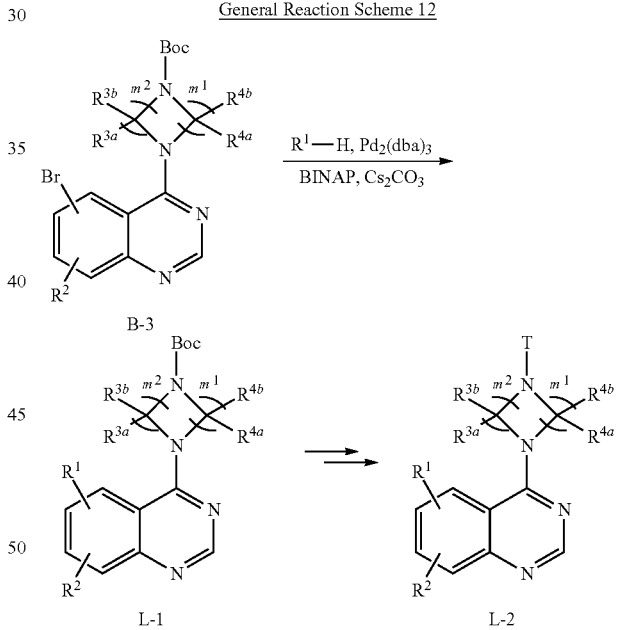

L-1 → L-2

Other embodiments of the compound of structure (I) (e.g., compound L-2) can be prepared according to General Reaction Scheme 12 ("Method L"), wherein $R^1$, $R^2$, $R^{3a}$, $R^{3b}$, $R^{4a}$, $R^{4b}$, T, $m^1$ and $m^2$ are as defined herein above. Specifically, compounds wherein $R^1$ is a N-heterocycle can be efficiently prepared according to Method L. Referring to General Reaction Scheme 12, compound B-3 is prepared according to Method B and treated under Buchwald conditions (where $R^1$—H is a N-heterocycle or alkylamino) to yield L-1. Methods for Buchwald reactions are well-known in the art. L-1 is then converted to L-2 according to the above general procedures.

General Reaction Scheme 13

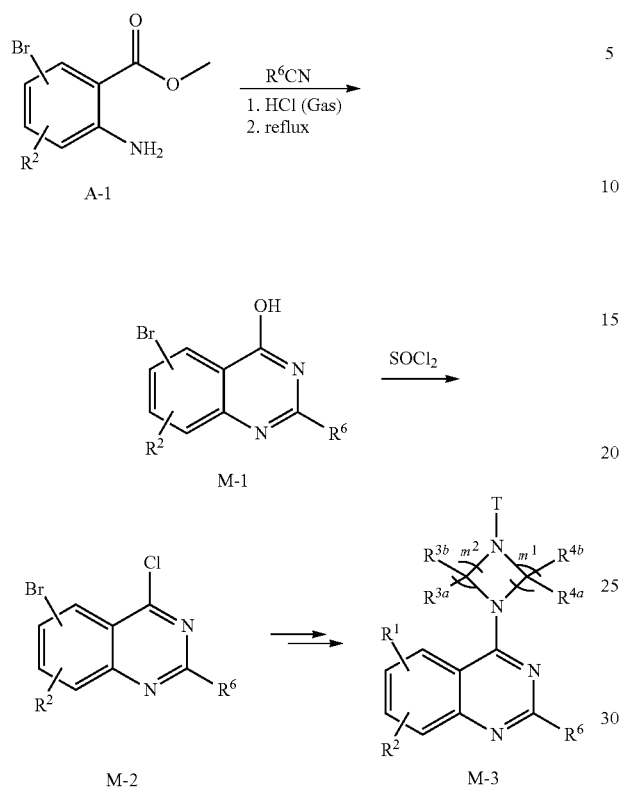

Other embodiments of the compound of structure (I) (e.g., compound M-3) can be prepared according to General Reaction Scheme 13 ("Method M"), wherein $R^1$, $R^2$, $R^{3a}$, $R^{3b}$, $R^{4a}$, $R^{4b}$, T, $m^1$ and $m^2$ are as defined herein above. Referring to General Reaction Scheme 13, compound A-1 is reacted an appropriate nitrile ($R^6$CN) to form compound M-1. In this regard, $R^6$ may be any of the $R^6$ moieties described herein, for example alkyl. M-1 is chlorinated by reaction with an appropriate reagent such as thionyl chloride. Compound M-3 is then prepared according to the general procedures outlined herein, for example the procedures of General Reaction Scheme 2.

General Reaction Scheme 14

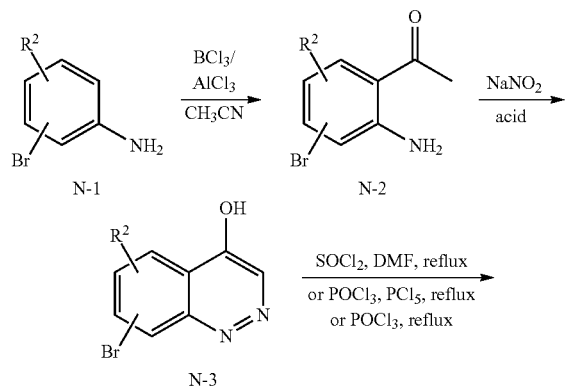

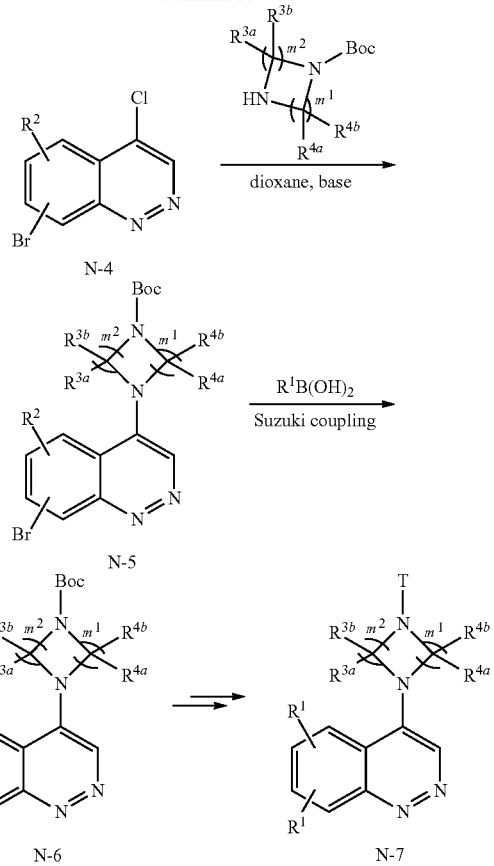

Embodiments of the compound of structure (I) (e.g., compound N-7) can be prepared according to General Reaction Scheme 14 ("Method N"), wherein $R^1$, $R^2$, $R^{3a}$, $R^{3b}$, $R^{4a}$, $R^{4b}$, T, $m^1$ and $m^2$ are as defined herein above. As shown in General Reaction Scheme 14, compounds of structure N-1 can be purchased from commercial sources or prepared according to methods familiar to one of ordinary skill in the art. Compound N-1 is reacted with methylnitrile to form compound N-2. Reaction of N-2 with sodium nitrite under acidic conditions yields cinnolines of structure N-3. N-3 is chlorinated under appropriate conditions (e.g., SOCl$_2$, POCl$_3$/PCl$_5$ or POCl$_3$) to yield the chlorocinnoline N-4. Reaction of N-4 with an appropriately protected heterocycle under basic conditions yields N-5. Appropriate protecting groups include butyloxycarbonyl (BOC) as depicted in General reaction Scheme 1, as well as other protecting groups known in the art. Suzuki reaction of N-5 with an appropriate reagent to install the $R^1$ moiety results in N-6. Deprotection of N-6 followed by acylation with an acid chloride (or sulfonyl chloride) or acid and appropriate activating reagents yields N-7.

General Reaction Scheme 15

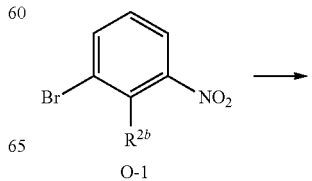

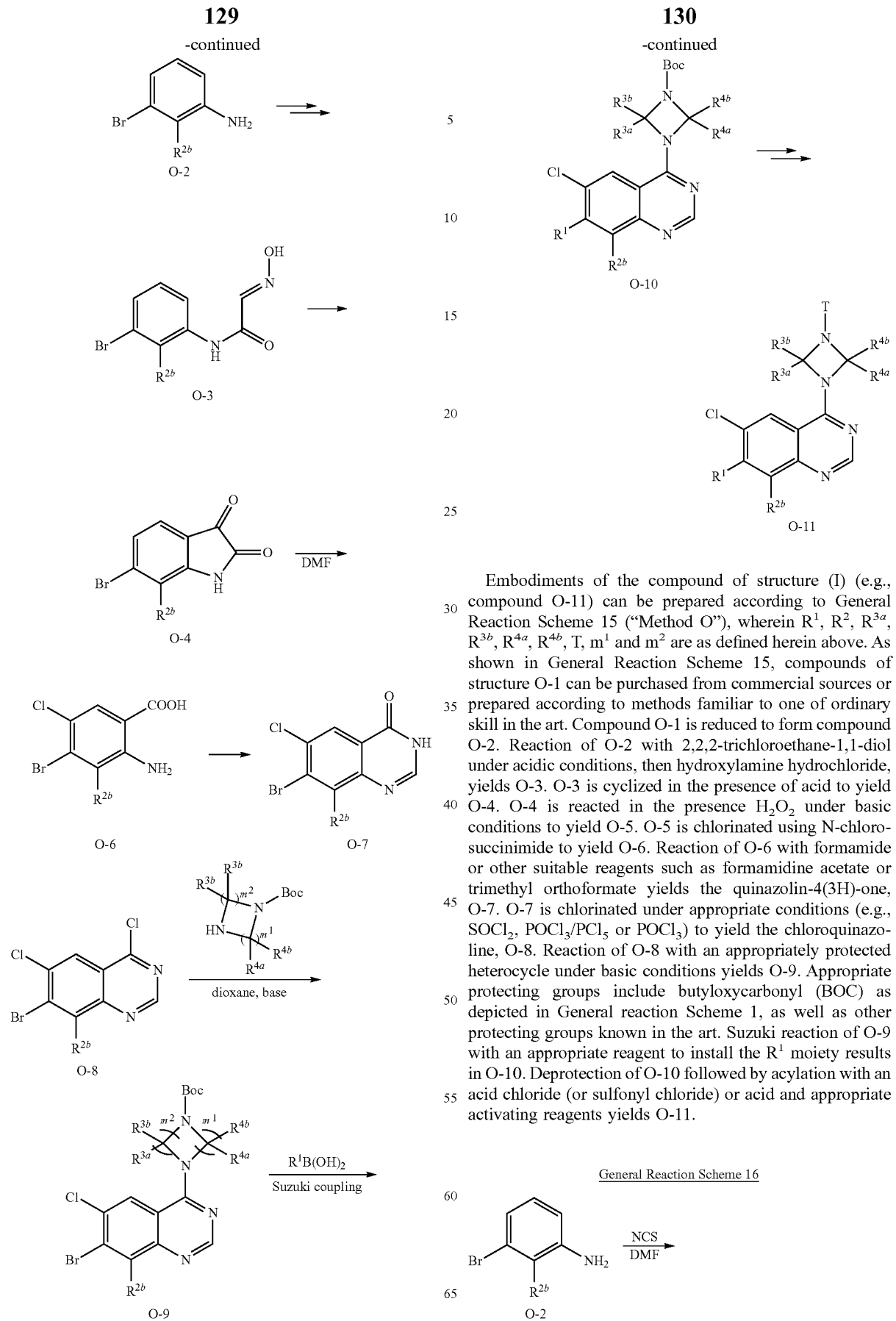

Embodiments of the compound of structure (I) (e.g., compound O-11) can be prepared according to General Reaction Scheme 15 ("Method O"), wherein $R^1$, $R^2$, $R^{3a}$, $R^{3b}$, $R^{4a}$, $R^{4b}$, T, $m^1$ and $m^2$ are as defined herein above. As shown in General Reaction Scheme 15, compounds of structure O-1 can be purchased from commercial sources or prepared according to methods familiar to one of ordinary skill in the art. Compound O-1 is reduced to form compound O-2. Reaction of O-2 with 2,2,2-trichloroethane-1,1-diol under acidic conditions, then hydroxylamine hydrochloride, yields O-3. O-3 is cyclized in the presence of acid to yield O-4. O-4 is reacted in the presence $H_2O_2$ under basic conditions to yield O-5. O-5 is chlorinated using N-chlorosuccinimide to yield O-6. Reaction of O-6 with formamide or other suitable reagents such as formamidine acetate or trimethyl orthoformate yields the quinazolin-4(3H)-one, O-7. O-7 is chlorinated under appropriate conditions (e.g., $SOCl_2$, $POCl_3/PCl_5$ or $POCl_3$) to yield the chloroquinazoline, O-8. Reaction of O-8 with an appropriately protected heterocycle under basic conditions yields O-9. Appropriate protecting groups include butyloxycarbonyl (BOC) as depicted in General reaction Scheme 1, as well as other protecting groups known in the art. Suzuki reaction of O-9 with an appropriate reagent to install the $R^1$ moiety results in O-10. Deprotection of O-10 followed by acylation with an acid chloride (or sulfonyl chloride) or acid and appropriate activating reagents yields O-11.

General Reaction Scheme 16

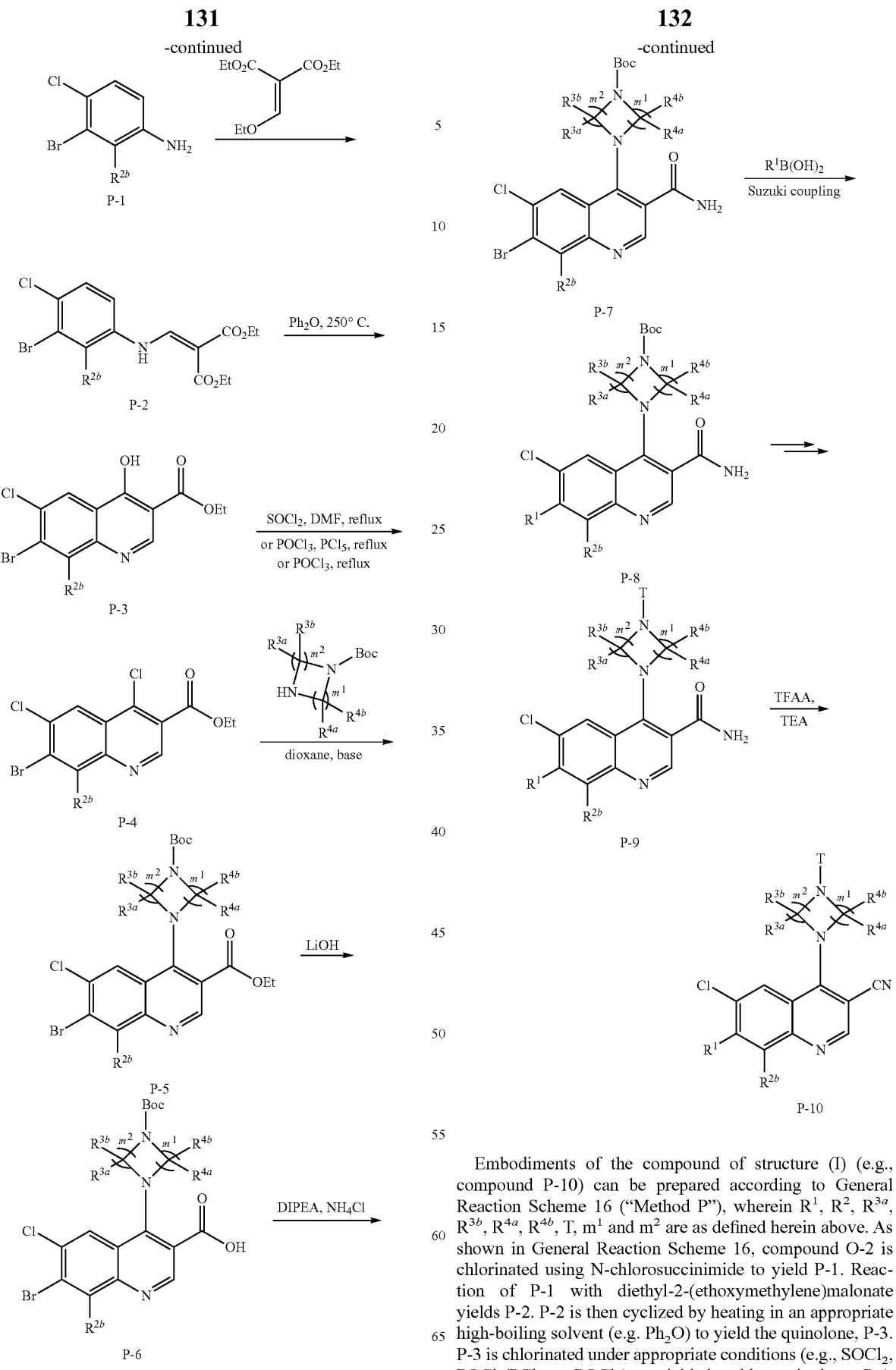

Embodiments of the compound of structure (I) (e.g., compound P-10) can be prepared according to General Reaction Scheme 16 ("Method P"), wherein $R^1$, $R^2$, $R^{3a}$, $R^{3b}$, $R^{4a}$, $R^{4b}$, T, $m^1$ and $m^2$ are as defined herein above. As shown in General Reaction Scheme 16, compound O-2 is chlorinated using N-chlorosuccinimide to yield P-1. Reaction of P-1 with diethyl-2-(ethoxymethylene)malonate yields P-2. P-2 is then cyclized by heating in an appropriate high-boiling solvent (e.g. $Ph_2O$) to yield the quinolone, P-3. P-3 is chlorinated under appropriate conditions (e.g., $SOCl_2$, $POCl_3/PCl_5$ or $POCl_3$) to yield the chloroquinolone, P-4.

Reaction of P-4 with an appropriately protected heterocycle under basic conditions yields P-5. Appropriate protecting groups include butyloxycarbonyl (BOC) as depicted in General reaction Scheme 1, as well as other protecting groups known in the art. Saponification of P-5 followed by amidation yields P-6 and P-7, respectively. Suzuki reaction of P-7 with an appropriate reagent to install the $R^1$ moiety results in P-8. Deprotection of P-8 followed by acylation with an acid chloride (or sulfonyl chloride) or acid and appropriate activating reagents yields P-9. Reaction of P-9 in the presence of acid yielded P-10.

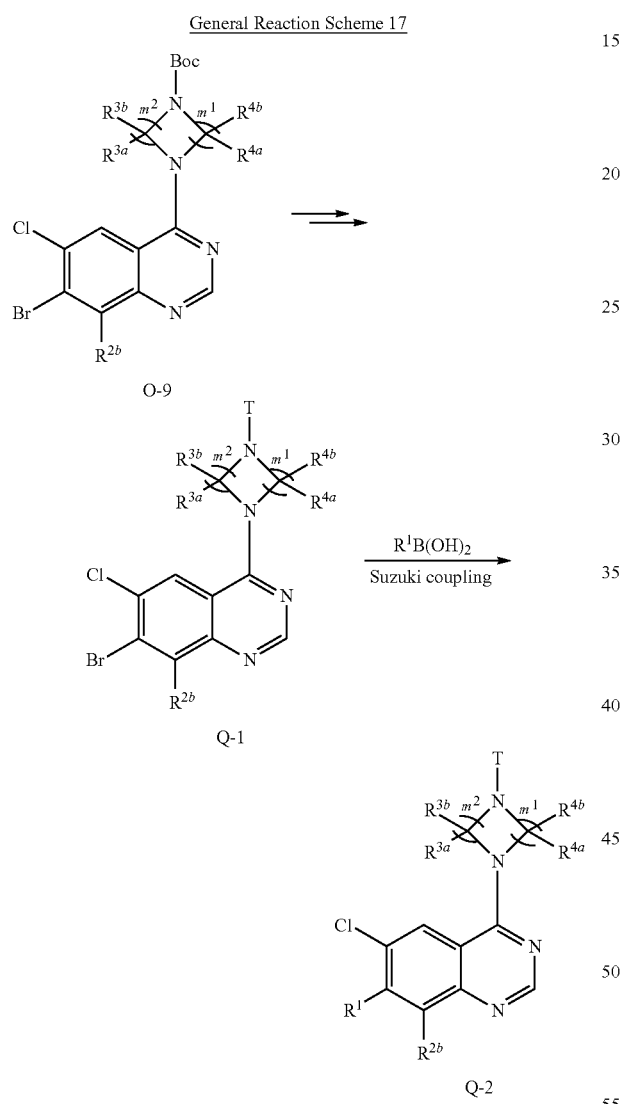

Embodiments of the compound of structure (I) (e.g., compound Q-2) can be prepared according to General Reaction Scheme 16 ("Method Q"), wherein $R^1$, $R^2$, $R^{3a}$, $R^{3b}$, $R^{4a}$, $R^{4b}$, T, $m^1$ and $m^2$ are as defined herein above. As shown in General Reaction Scheme 17, deprotection of compound O-9 followed by acylation with an acid chloride (or sulfonyl chloride) or acid and appropriate activating reagents yields Q-1. Suzuki reaction of Q-1 with an appropriate reagent to install the $R^1$ moiety results in Q-2.

One skilled in the art will recognize that certain modifications to the above schemes are possible to prepare different embodiments of compounds of structure (I). For example, for ease of illustration, most of the above schemes depict preparation of compounds of structure (I) wherein $L^1$ is a bond. However, one of ordinary skill in the art will readily recognize that compounds wherein $L^1$ is $NR^7$ can be prepared by substituting a heterocycle having the following structure (see e.g., Method C):

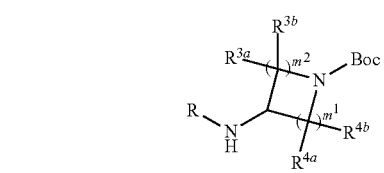

where R is H, a protecting group or $C_1$-$C_6$alkyl.

Compounds described herein can be synthesized according to the general schemes described herein. For example, compound 10 (1-(4-(7-chloro-6-(4-chlorophenyl)quinazolin-4-yl)piperazin-1-yl)propan-1-one) is synthesized according to the scheme:

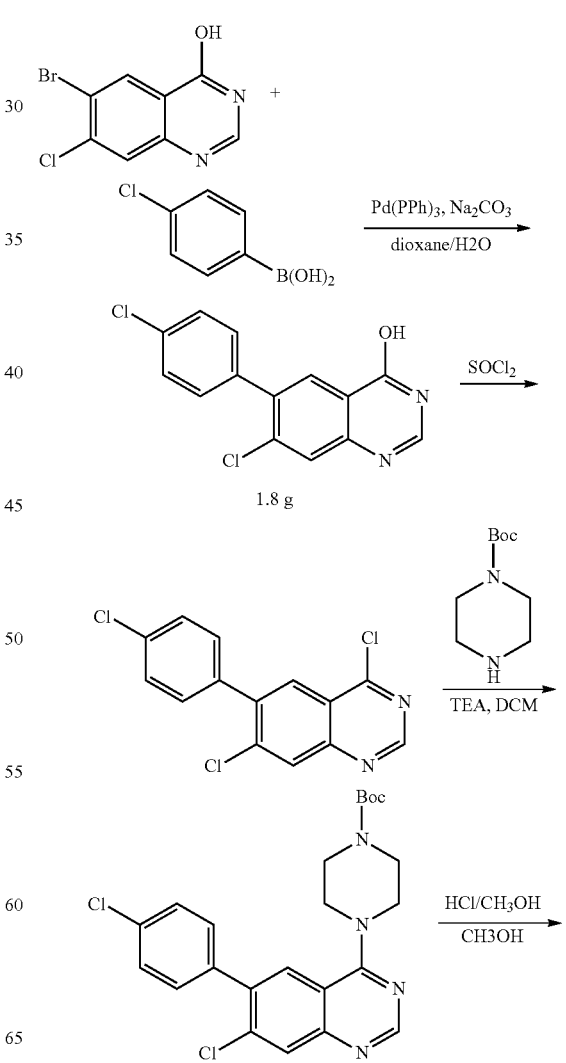

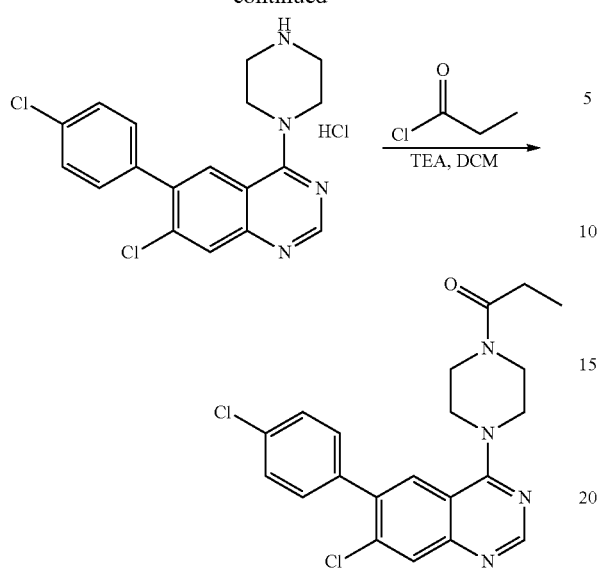

Selective coupling of 6-bromo-7-chloroquinazolin-4-ol with 4-chlorophenylboronic acid is achieved via Suzuki coupling in the presence of catalytic Pd(PPh)$_3$ and sodium carbonate to furnish the corresponding biaryl. Conversion of the quinazolinol to the corresponding chloride occurs in the presence of thionyl chloride. Addition of tert-butyl piperazine-1-carboxylate in the presence of triethyl amine furnishes the corresponding aryl amine. Deprotection of the Boc group is achieved in the presence of HCl/methanol to furnish the corresponding ammonium salt. Coupling to propanoyl chloride in the presence of triethylamine furnishes the corresponding amide. Purification by standard purification methods furnishes compound 10.

Analogously, further derivatives can be synthesized by an alternate synthetic approach. For example, compound 35 (2-(6-chloro-8-fluoro-4-(4-(methylsulfonyl)piperazin-1-yl)quinazolin-7-yl)-3-fluorophenol) is synthesized according to the scheme:

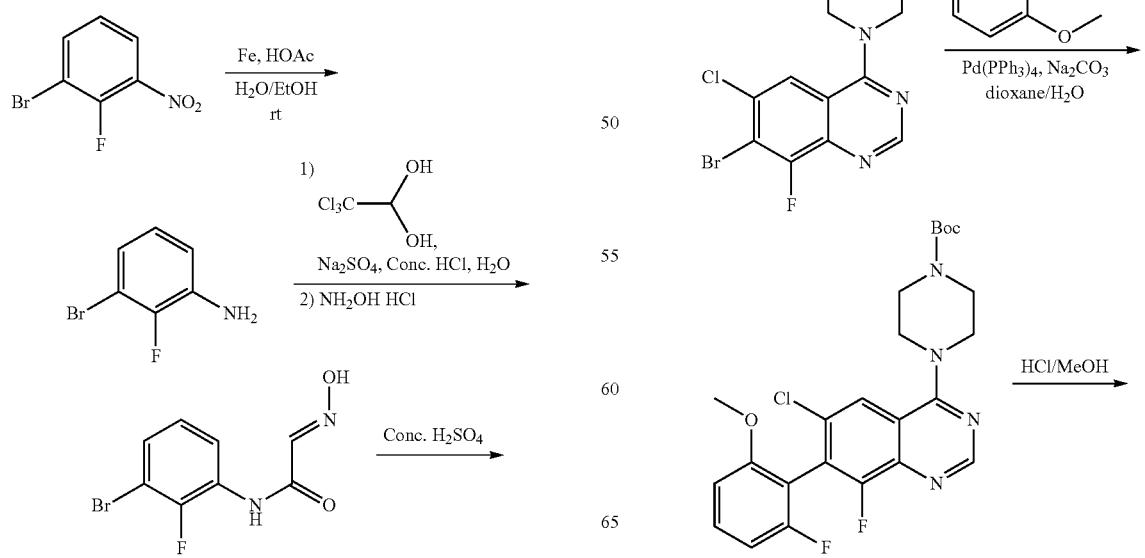

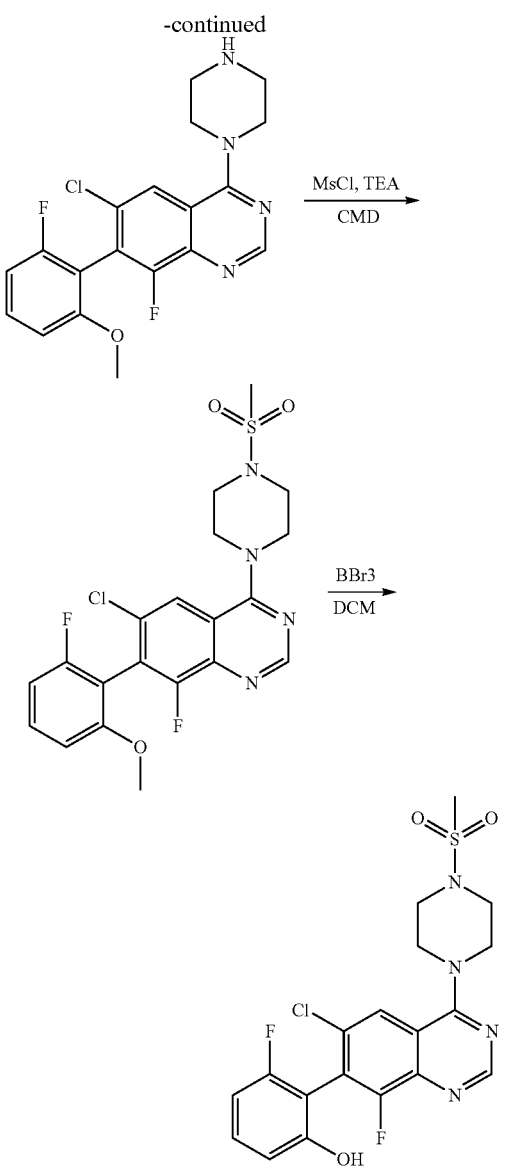

3-bromo-2-fluoroaniline is produced via reduction of the corresponding nitro. Coupling of the analine to 2,2,2-trichloroethane-1,1-diol and subsequent treatment with hydroxylamine hydrochloride furnishes the corresponding oxime amide which cyclizes to form 6-bromo-7-fluoroindoline-2,3-dione. Treatment with peroxide and 2M sodium hydroxide furnishes the aniline benzoic acid derivative which is further chlorinated with NCS to furnish the penta-substituted aromatic compound. Cyclization in the presence of formimidamide and acetic acid, followed by chlorination with thionyl chloride furnishes 7-bromo-4,6-dichloro-8-fluoroquinazoline. Treatment with tert-butyl piperazine-1-carboxylate forms the corresponding aryl amine. Subsequent selective Suzuki coupling with an aryl boronic acid, such as 2-fluoro-6-methoxyphenylboronic acid, displaces the chlorine atom and furnishes the corresponding biaryl. Deprotection of the Boc group is achieved in the presence of HCl/methanol to furnish the desired deprotect amine compound. Coupling of the amine can be achieved with a variety of electrophiles to form various analogs at this stage. For example, the amine is treated with MsCl in the presence of triethylamine to furnish 6-chloro-8-fluoro-7-(2-fluoro-6-methoxyphenyl)-4-(4-(methylsulfonyl)piperazin-1-yl)quinazoline. Demethylation occurs in the presence of BBr$_3$ in dichloromethane to furnish the corresponding phenol, compound 35.

Pharmaceutical Compositions

Other embodiments are directed to pharmaceutical compositions. The pharmaceutical composition comprises any one (or more) of the foregoing compounds and a pharmaceutically acceptable carrier. In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent (e.g., anticancer agent). Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, optic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician.

In some embodiments, a compound of the invention is administered in a single dose. Typically, such administration will be by injection, e.g., intravenous injection, in order to introduce the agent quickly. However, other routes are used as appropriate. In some embodiments, a single dose of a compound of the invention is used for treatment of an acute condition.

In some embodiments, a compound of the invention is administered in multiple doses. In some embodiments, dosing is about once, twice, three times, four times, five times, six times, or more than six times per day. In other embodiments, dosing is about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

In some embodiments, the compounds of the invention are administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999).

Provided herein are pharmaceutical compositions comprising a compound of structure (I) and a pharmaceutically acceptable diluent(s), excipient(s), or carrier(s). In certain embodiments, the compounds described are administered as pharmaceutical compositions in which compounds of structure (I) are mixed with other active ingredients, as in combination therapy. Encompassed herein are all combinations of actives set forth in the combination therapies section below and throughout this disclosure. In specific embodiments, the pharmaceutical compositions include one or more compounds of structure (I).

A pharmaceutical composition, as used herein, refers to a mixture of a compound of structure (I) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of structure (I) provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds of structure (I) is formulated in an aqueous solutions. In specific embodiments, the aqueous solution is selected from, by way of example only, a physiologically compatible buffer, such as Hank's solution, Ringer's solution, or physiological saline buffer. In other embodiments, one or more compound of structure (I) is/are formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or non-aqueous solutions. In specific embodiments, such solutions include physiologically compatible buffers and/or excipients.

In another embodiment, compounds described herein are formulated for oral administration. Compounds described herein are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds (e.g., compounds of structure (I)) are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of structure (I) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of structure (I) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of structure (I) is accomplished by means of iontophoretic patches and the like. In certain embodiments, transdermal patches provide controlled delivery of the compounds of structure (I). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of structure (I) are formulated for administration by inhalation. Various forms suitable for administration by inhalation include, but are not limited to, aerosols, mists or powders. Pharmaceutical compositions of any of compound of structure (I) are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound and a suitable powder base such as lactose or starch.

In still other embodiments, the compounds of structure (I) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound of structure (I) are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of structure (I), described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least one compound of structure (I) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of structure (I). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more compounds of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

Kits/Articles of Manufacture

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions is presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

Methods

The present invention provides a method of inhibiting Ras-mediated cell signaling comprising contacting a cell with an effective amount of one or more compounds disclosed herein Inhibition of Ras-mediated signal transduction can be assessed and demonstrated by a wide variety of ways known in the art. Non-limiting examples include a showing of (a) a decrease in GTPase activity of Ras; (b) a decrease in GTP binding affinity or an increase in GDP binding affinity; (c) an increase in K off of GTP or a decrease in K off of GDP; (d) a decrease in the levels of signaling transduction molecules downstream in the Ras pathway, such as a decrease in pMEK level; and/or (e) a decrease in binding of Ras complex to downstream signaling molecules including but not limited to Raf. Kits and commercially available assays can be utilized for determining one or more of the above.

The invention also provides methods of using the compounds or pharmaceutical compositions of the present invention to treat disease conditions, including but not limited to conditions implicated by K-Ras, H-Ras or N-Ras mutation, H-Ras mutation and/or N-Ras mutation (e.g., cancer).

The invention also provides methods of using the compounds or pharmaceutical compositions of the present invention to treat disease conditions, including but not limited to conditions implicated by G12C G12D, G12S, G12V, and/or G13D mutations in K-Ras, H-Ras and/or N-Ras, (e.g., cancer).

In some embodiments, a method for treatment of cancer is provided, the method comprising administering an effective amount of any of the foregoing pharmaceutical compositions comprising a compound of structure (I) to a subject in need thereof. In some embodiments, the cancer is mediated by a K-Ras, H-Ras or N-Ras G12C mutation. In other embodiments, the cancer is pancreatic cancer, colon cancer, MYH associated polyposis, colorectal cancer or lung cancer.

In some embodiments the invention provides method of treating a disorder in a subject in need thereof, wherein the said method comprises determining if the subject has a K-Ras, H-Ras or N-Ras G12C mutation and if the subject is determined to have the K-Ras, H-Ras or N-Ras G12C mutation, then administering to the subject a therapeutically effective dose of at least one compound of structure (I) or a pharmaceutically acceptable salt, ester, prodrug, tautomer, solvate, hydrate or derivative thereof.

The disclosed compounds strongly inhibit anchorage-independent cell growth and therefore have the potential to inhibit tumor metastasis. Accordingly, in another embodiment the disclosure provides a method for inhibiting tumor metastasis, the method comprising administering an effective amount a pharmaceutical composition of comprising any of the compounds disclosed herein and a pharmaceutically acceptable carrier to a subject in need thereof.

Ras mutations including but not limited to K-Ras, H-Ras or N-Ras mutations have also been identified in hematological malignancies (e.g., cancers that affect blood, bone marrow and/or lymph nodes). Accordingly, certain embodiments are directed to administration of a disclosed compounds (e.g., in the form of a pharmaceutical composition) to a patient in need of treatment of a hematological malignancy. Such malignancies include, but are not limited to leukemias and lymphomas. For example, the presently disclosed compounds can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL) and/or other leukemias. In other embodiments, the compounds are useful for treatment of lymphomas such as all subtypes of Hodgkins lymphoma or non-Hodgkins lymphoma.

Determining whether a tumor or cancer comprises a Ras mutation including but not limited to a K-Ras, H-Ras or N-Ras mutation can be undertaken by assessing the nucleotide sequence encoding the Ras protein, by assessing the amino acid sequence of Ras protein, or by assessing the characteristics of a putative Ras mutant protein. The sequence of wild-type human Ras proteins including but not limited to K-Ras, H-Ras or N-Ras is known in the art, (e.g. Accession No. NP203524).

Methods for detecting a mutation in a Ras nucleotide sequence including but not limited to K-Ras, H-Ras or N-Ras nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for Ras mutations including but not limited to K-Ras, H-Ras or N-Ras mutations by real-time PCR. In real-time PCR, fluorescent probes specific for the Ras mutation including but not limited to K-Ras, H-Ras or N-Ras mutation are used. When a mutation is present, the probe binds and fluorescence is detected. In some embodiments, the Ras mutation including but not limited to a K-Ras, H-Ras or N-Ras mutation is identified using a direct sequencing method of specific regions (e.g., exon 2 and/or exon 3) in the Ras gene or corresponding K-Ras, H-Ras or N-Ras gene, for example. This technique will identify all possible mutations in the region sequenced.

Methods for detecting a mutation in a Ras protein including but not limited to a K-Ras, H-Ras or N-Ras protein are known by those of skill in the art. These methods include, but are not limited to, detection of a K-Ras, H-Ras or N-Ras mutant using a binding agent (e.g., an antibody) specific for the mutant protein, protein electrophoresis and Western blotting, and direct peptide sequencing.

Methods for determining whether a tumor or cancer comprises a Ras mutation including but not limited to a K-Ras, H-Ras or N-Ras mutation can use a variety of samples. In some embodiments, the sample is taken from a subject having a tumor or cancer. In some embodiments, the sample is taken from a subject having a cancer or tumor. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, said method relates to the treatment of a non-cancerous hyperproliferative disorder such as benign hyperplasia of the skin (e. g., psoriasis), restenosis, or prostate (e. g., benign prostatic hypertrophy (BPH)).

In certain particular embodiments, the invention relates to methods for treatment of lung cancers, the methods comprise administering an effective amount of any of the above described compound (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In other embodiments, the lung cancer is a small cell lung carcinoma. Other lung cancers treatable with the disclosed compounds include, but are not limited to, glandular tumors, carcinoid tumors and undifferentiated carcinomas.

Subjects that can be treated with compounds of the invention, or pharmaceutically acceptable salt, ester, prodrug, solvate, tautomer, hydrate or derivative of said compounds, according to the methods of this invention include, for example, subjects that have been diagnosed as having acute myeloid leukemia, acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments subjects that are treated with the compounds of the invention include subjects that have been diagnosed as having a non-cancerous hyperproliferative disorder such as benign hyperplasia of the skin (e. g., psoriasis), restenosis, or prostate (e. g., benign prostatic hypertrophy (BPH)).

The invention further provides methods of modulating a mutant Ras including but not limited to a mutant K-Ras, H-Ras or N-Ras protein activity by contacting the protein with an effective amount of a compound of the invention. Modulation can be inhibiting or activating protein activity. In some embodiments, the invention provides methods of inhibiting protein activity by contacting the mutant Ras protein (for example, a Mutant K-Ras, H-Ras or N-Ras protein) with an effective amount of a compound of the invention in solution. In some embodiments, the invention provides methods of inhibiting the mutant Ras protein activity by contacting a cell, tissue, organ that express the protein of interest. In some embodiments, the invention provides methods of inhibiting protein activity in a subject including but not limited to rodents and mammal (e.g., human) by administering into the subject an effective amount of a compound of the invention. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the invention provides methods of inhibiting Ras activity including but not limited to K-Ras, H-Ras or N-Ras mutant activity in a cell by contacting said cell with an amount of a compound of the invention sufficient to inhibit the activity of Ras or a K-Ras, H-Ras or N-Ras mutant in said cell. In some embodiments, the invention provides methods of inhibiting Ras or mutant K-Ras, H-Ras or N-Ras activity in a tissue by contacting said tissue with an amount of a compound of the invention sufficient to inhibit the activity of mutant Ras or including but not limited to mutant K-Ras, H-Ras or N-Ras in said tissue. In some embodiments, the invention provides methods of inhibiting Ras including but not limited to mutant K-Ras, H-Ras or N-Ras activity in an organism by contacting said organism with an amount of a compound of the invention sufficient to inhibit the activity of Ras including but not limited to mutant K-Ras, H-Ras or N-Ras in said organism. In some embodiments, the invention provides methods of inhibiting Ras including but not limited to mutant K-Ras, H-Ras or N-Ras activity in an animal by contacting said animal with an amount of a compound of the invention sufficient to inhibit the activity of Ras including but not limited to mutant K-Ras, H-Ras or N-Ras in said animal. In some embodiments, the invention provides methods of inhibiting Ras including but not limited to mutant K-Ras, H-Ras or N-Ras activity in a mammal by contacting said mammal with an amount of a compound of the invention sufficient to inhibit the activity of Ras including but not limited to mutant K-Ras, H-Ras or N-Ras in said mammal. In some embodiments, the invention provides methods of inhibiting Ras including but not limited to mutant K-Ras, H-Ras or N-Ras activity in a human by contacting said human with an amount of a compound of the invention sufficient to inhibit the activity of Ras including but not limited to mutant K-Ras, H-Ras or N-Ras in said human. The present invention provides methods of treating a disease mediated by Ras including but not limited to mutant K-Ras, H-Ras or N-Ras activity in a subject in need of such treatment.

The present invention also provides methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, tautomer, hydrate or derivative thereof. In one aspect, such therapy includes but is not limited to the combination of one or more compounds of the invention with chemotherapeutic agents, therapeutic antibodies, and radiation treatment, to provide a synergistic or additive therapeutic effect.

Many chemotherapeutics are presently known in the art and can be used in combination with the compounds of the invention. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This invention further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The compounds or pharmaceutical compositions of the invention can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the invention and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863, 949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i. e., MAP-1, MMP-3, MMP-4, MMP-5, MMP-6, MMP-7, MMP-8, MMP-10, MMP-11, MMP-12, and MMP-13). Some specific examples of MMP inhibitors useful in the invention are AG-3340, RO 32-3555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

The invention also relates to a method of and to a pharmaceutical composition for treating a cardiovascular disease in a mammal which comprises an amount of a compound of the invention, or a pharmaceutically acceptable salt, ester, prodrug, solvate, tautomer, hydrate or derivative thereof, or an isotopically-labeled derivative thereof, and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

In some embodiments, the compounds described herein are formulated or administered in conjunction with liquid or solid tissue barriers also known as lubricants. Examples of tissue barriers include, but are not limited to, polysaccharides, polyglycans, seprafilm, interceed and hyaluronic acid.

In some embodiments, medicaments which are administered in conjunction with the compounds described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (+4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments are used in the form of salts (e.g. as alkali metal or amine salts or as acid addition salts) or as esters (e.g. lower alkyl esters) or as solvates (e.g. hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-lactam antibiotics, an agent comprising an aminoglycoside, protein synthesis inhibitors, drugs used in the chemotherapy of tuberculosis, mycobacterium avium complex disease, and leprosy, antifungal agents, antiviral agents including nonretroviral agents and antiretroviral agents.

Examples of therapeutic antibodies that can be combined with a compound of the invention include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

For treating renal carcinoma, one may combine a compound of the present invention with sorafenib and/or avastin. For treating an endometrial disorder, one may combine a compound of the present invention with doxorubincin, taxotere (taxol), and/or cisplatin (carboplatin). For treating ovarian cancer, one may combine a compound of the present invention with cisplatin (carboplatin), taxotere, doxorubincin, topotecan, and/or tamoxifen. For treating breast cancer, one may combine a compound of the present invention with taxotere (taxol), gemcitabine (capecitabine), tamoxifen, letrozole, tarceva, lapatinib, PD0325901, avastin, herceptin, OSI-906, and/or OSI-930. For treating lung cancer, one may combine a compound of the present invention with taxotere (taxol), gemcitabine, cisplatin, pemetrexed, Tarceva, PD0325901, and/or avastin.

Further therapeutic agents that can be combined with a compound of the invention are found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the one or more compounds of the invention will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the invention and any of the agents described above can be simultaneously administered, wherein both the agents are present in separate formulations. In another alternative, a compound of the present invention can be administered just followed by and any of the agents described above, or vice versa. In some embodiments of the separate administration protocol, a compound of the invention and any of the agents described above are administered a few minutes apart, or a few hours apart, or a few days apart.

The examples and preparations provided below further illustrate and exemplify the compounds of the present invention and methods of preparing such compounds. It is to be understood that the scope of the present invention is not limited in any way by the scope of the following examples and preparations. In the following examples, and throughout the specification and claims, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Example 1

Biochemical and Cellular Assays of the Compounds

Inhibition of Cell Growth:

The ability of the subject compounds to inhibit Ras-mediated cell growth is assessed and demonstrated as follows. Cells expressing a wildtype or a mutant Ras are plated in white, clear bottom 96 well plates at a density of 5,000 cells per well. Cells are allowed to attach for about 2 hours after plating before a compound disclosed herein is added. After certain hours (e.g., 24 hours, 48 hours, or 72 hours of cell growth), cell proliferation is determined by measuring total ATP content using the Cell Titer Glo reagent (Promega) according to manufacturer's instructions. Proliferation EC50s are determined by analyzing 8 point compound dose responses at half-log intervals decreasing from 100 µM.

Inhibition of Ras-Mediated Signaling Transduction:

The ability of the compounds disclosed herein in inhibiting Ras-mediated signaling is assessed and demonstrated as follows. Cells expressing wild type or a mutant Ras (such as G12C, G12D, G12V, or G12A) are treated with or without (control cells) a subject compound Inhibition of Ras signaling by one or more subject compounds is demonstrated by a decrease in the steady-state level of phosphorylated MEK, phosphorylated ERK, phosphorylated RSK, and/or Raf binding in cells treated with the one or more of the subject compounds as compared to the control cells.

Inhibition of Ras-Mediated Signaling Transduction:

The ability of the compounds disclosed herein in inhibiting Ras-mediated signaling is assessed and demonstrated as follows. Cells expressing wild type or a mutant Ras (such as G12C, G12D, G12V, or G12A) are treated with or without (control cells) a subject compound Inhibition of Ras signaling by one or more subject compounds is demonstrated by a decrease in binding of Ras complex to downstream signaling molecules (for example Raf) in cells treated with the one or more of the subject compounds as compared to the control cells.

A compound of Table 1 or Table 2 is tested according to the above procedures. The compound of Table 1 or Table 2 is expected to inhibit Ras-mediated signaling transduction by one or more of the procedures described herein.

Example 2

Assessing Inhibition of Cell Proliferation by a Compound Disclosed Herein

Two cancer cell lines, NCI H441 (human lung adenenocarcinoma cells comprising a G12V mutation) and MIA paca-2 (human pancreatic carcinoma comprising a G12C mutation) are used in this experiment. Both the cell lines are treated with a compound of Table 1 or Table 2 disclosed herein at a concentration of 100 µM, 30 µM, 10 µM and 3 µM and cell potency is measured as described in Example 1.

Example 3

Comparison of Cell Proliferation Inhibition by a Compound Disclosed Herein

Three cell lines, NCI H441 (human lung adenenocarcinoma cells), NCI 1568 (lung adenenocarcinoma cells) and MIA paca-2 (human pancreatic carcinoma) are used in this experiment. Both the cell lines are treated with a compound of Table 1 or Table 2 disclosed herein at a concentration of 100 μM, 30 μM, 10 μM and 3 μM and cell potency is measured.

All of the U.S. patents, U.S. patent application publications, U.S. patent applications, foreign patents, foreign patent applications and non-patent publications referred to in this specification and/or attached Application Data Sheet are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the following structure (I):

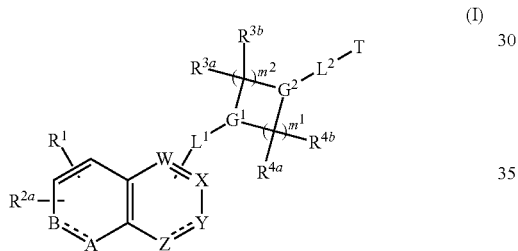

or a pharmaceutically acceptable salt thereof, wherein:
A is $CR^{2b}$;
B is $CR^1$;
$G^1$ and $G^2$ are each independently N or CH;
W is $CR^6$;
X is N;
Y is $CR^6$;
Z is N;
$L^1$ is a bond or $NR^7$;
$L^2$ is a bond or alkylene;
$R^1$ is H, cyano, halo, heterocyclyl, heteroaryl, aryloxy or aryl;
$R^{2a}$ and $R^{2b}$ are each independently H, halo, hydroxyl, $C_1$-$C_6$ alkyl, $C_1$-$C_6$ haloalkyl, $C_3$-$C_8$ cycloalkyl or aryl;
$R^{3a}$ and $R^{3b}$ are, at each occurrence, independently H, —OH, —NH$_2$, —CO$_2$H, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl; or $R^{3a}$ and $R^{3b}$ join to form a carbocyclic or heterocyclic ring; or $R^{3a}$ is H, —OH, —NH$_2$, —CO$_2$H, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl, and $R^{3b}$ joins with $R^{4b}$ to form a carbocyclic or heterocyclic ring;
$R^{4a}$ and $R^{4b}$ are, at each occurrence, independently H, —OH, —NH$_2$, —CO$_2$H, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl; or $R^{4a}$ and $R^{4b}$ join to form a carbocyclic or heterocyclic ring; or $R^{4a}$ is H, —OH, —NH$_2$, —CO$_2$H, halo, cyano, $C_1$-$C_6$ alkyl, $C_1$-$C_6$ alkynyl, hydroxylalkyl, aminoalkyl, alkylaminoalkyl, cyanoalkyl, carboxyalkyl, aminocarbonylalkyl or aminocarbonyl, and $R^{4b}$ joins with $R^{3b}$ to form a carbocyclic or heterocyclic ring;

$R^7$ is H or $C_1$-$C_6$ alkyl;

$R^6$ is, at each occurrence, independently H, oxo, cyano, cyanoalkyl, amino, aminylalkyl, aminylalkylaminyl, aminocarbonyl, alkylaminyl, haloalkylamino, hydroxylalkyamino, amindinylalkyl, amidinylalkoxy, amindinylalkylaminyl, guanidinylalkyl, guanidinylalkoxy, guanidinylalkylaminyl, $C_1$-$C_6$ alkoxy, aminylalkoxy, alkylcarbonylaminylalkoxy, $C_1$-$C_6$ alkyl, heterocyclyl, heterocyclyloxy, heterocyclylalkyloxy, heterocyclylamino, heterocyclylalkylamino, heteroaryl, heteroaryloxy, heteroarylalkyloxy, heteroarylamino, heteroarylalkylamino, aryl, aryloxy, arylamino, arylalkylamino, arylalkyloxy or a bond to $L^1$;

$m^1$ and $m^2$ are each independently 1, 2 or 3;

═══ indicates a single or double bond such that all valences are satisfied; and

T is a polar group capable of forming a complex with a Ras protein via an interaction other than one resulting in a covalent bond with the cysteine residue at position 12 of a K-Ras, H-Ras or N-Ras G12C mutant protein;

wherein a heteroaryl comprises one to six heteroatoms selected from nitrogen, oxygen and sulfur;

wherein a heterocyclyl comprises one to six heteroatoms selected from nitrogen, oxygen and sulfur;

wherein at least one of W, X, Y or Z is $CR^6$ where $R^6$ is a bond to $L^1$; and provided that when $R^1$, $R^{2a}$, and $R^{2b}$ are all independently selected from H and halo, then X and Z are both N and at least one of $R^{3a}$, $R^{3b}$, $R^{4a}$ or $R^{4b}$ is not H, and provided that at least one of $R^{2a}$ or $R^{2b}$ is not H when $R^1$ is pyridyl.

2. The compound of claim 1, wherein the compound has one of the following structures (I'j), (I'k), (I'l) or (I'm):

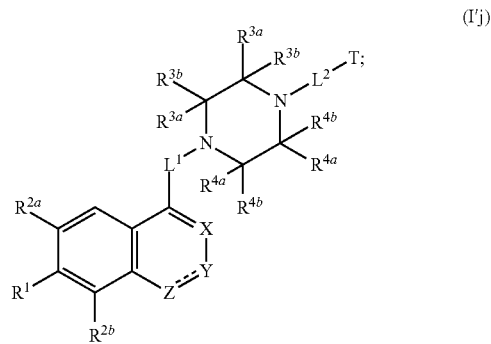

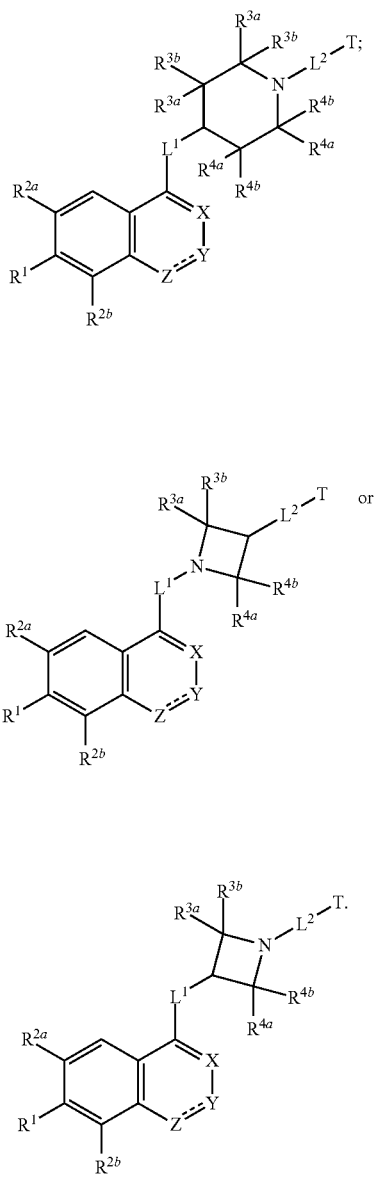

3. The compound of claim 1, wherein $R^1$ is aryl.

4. The compound of claim 3, wherein $R^1$ is phenyl or naphthyl.

5. The compound of claim 1, wherein $R^1$ is substituted with one or more substituents selected from halo, cyano, cyano$C_1$-$C_6$alkyl, cyano$C_3$-$C_8$cycloalkyl, hydroxyl, $C_1$-$C_6$alkyl, $C_1$-$C_6$alkylcycloalkyl, $C_2$-$C_6$alkynyl, $C_1$-$C_6$alkoxy, $C_1$-$C_6$haloalkoxy, $C_1$-$C_6$alkylaminyl, $C_1$-$C_6$alkylcarbonylaminyl, $C_1$-$C_6$hydroxy alkyl, $C_1$-$C_6$haloalkyl, $C_1$-$C_6$alkoxyalkyl, aminosulfone, aminocarbonyl, aminocarbonyl$C_1$-$C_6$alkyl, aminocarbonyl$C_3$-$C_8$cycloalkyl, $C_1$-$C_6$alkylaminocarbonyl, $C_3$-$C_8$cycloalkylaminocarbonyl, $C_3$-$C_8$cycloalkylalkyl and $C_3$-$C_8$cycloalkyl, $C_3$-$C_8$fusedcycloalkyl and heteroaryl.

6. The compound of claim 5, wherein $R^1$ is substituted with one or more substituents selected from fluoro, chloro, bromo, cyano, hydroxyl, hydroxylmethyl, methoxy, methoxymethyl, ethyl, isopropyl, trifluoromethyl, aminocarbonyl and cyclopropyl.

7. The compound of claim 1, wherein R has one of the following structures:

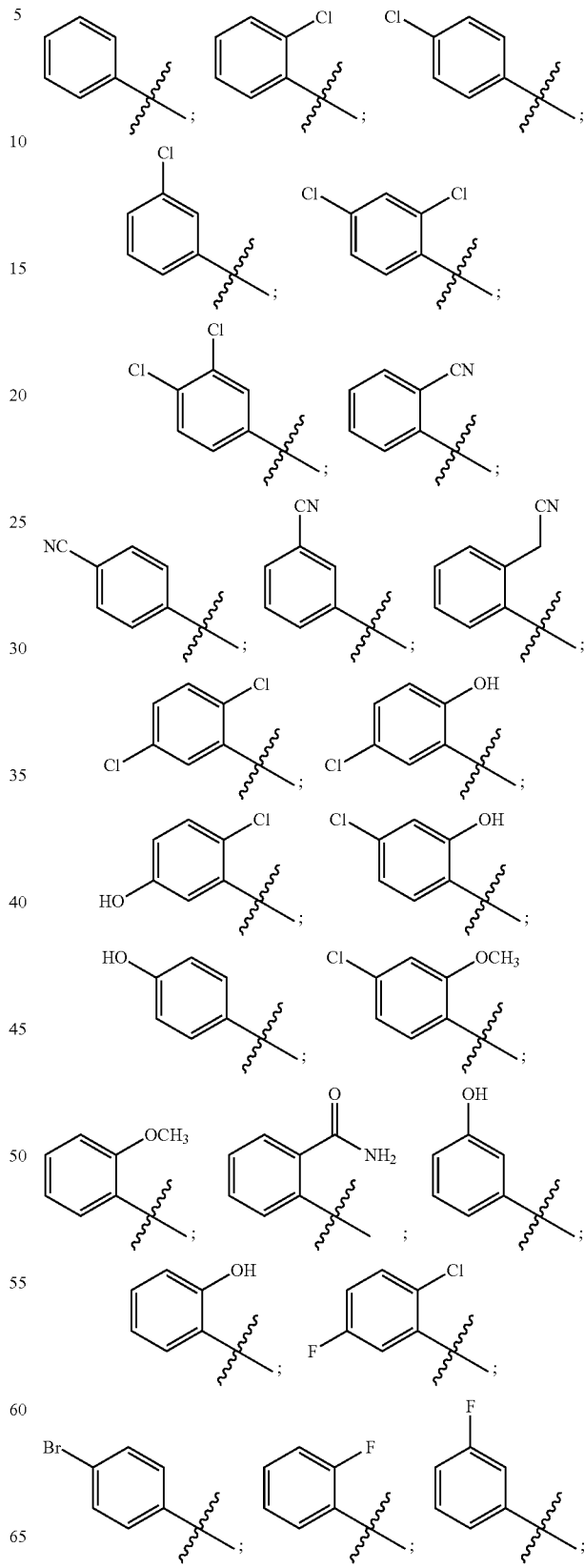

-continued
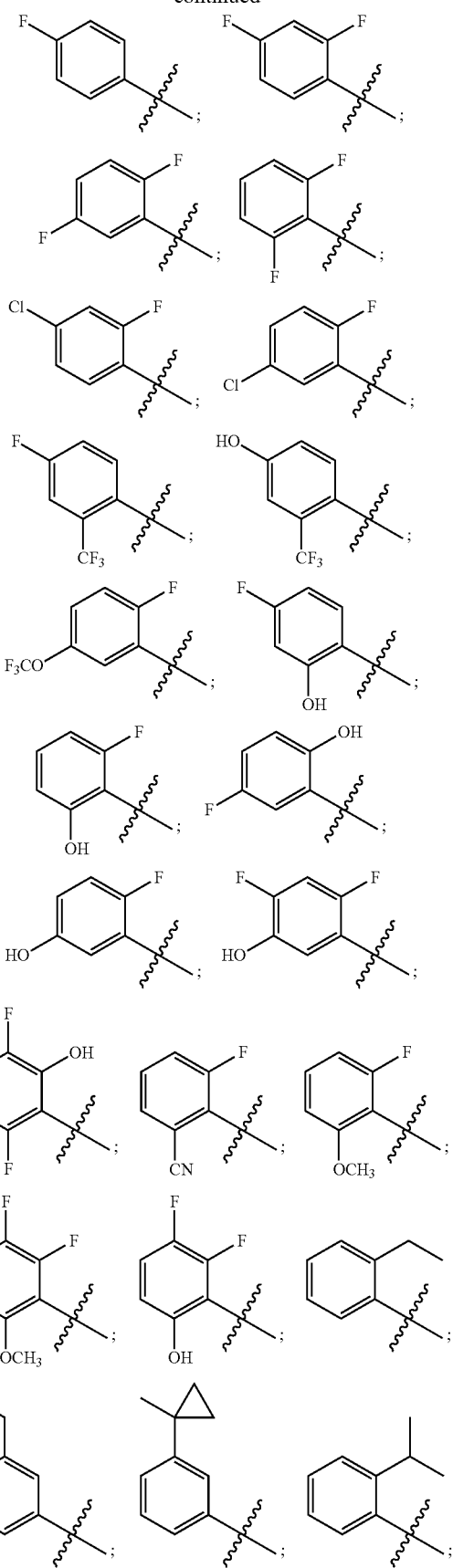
-continued
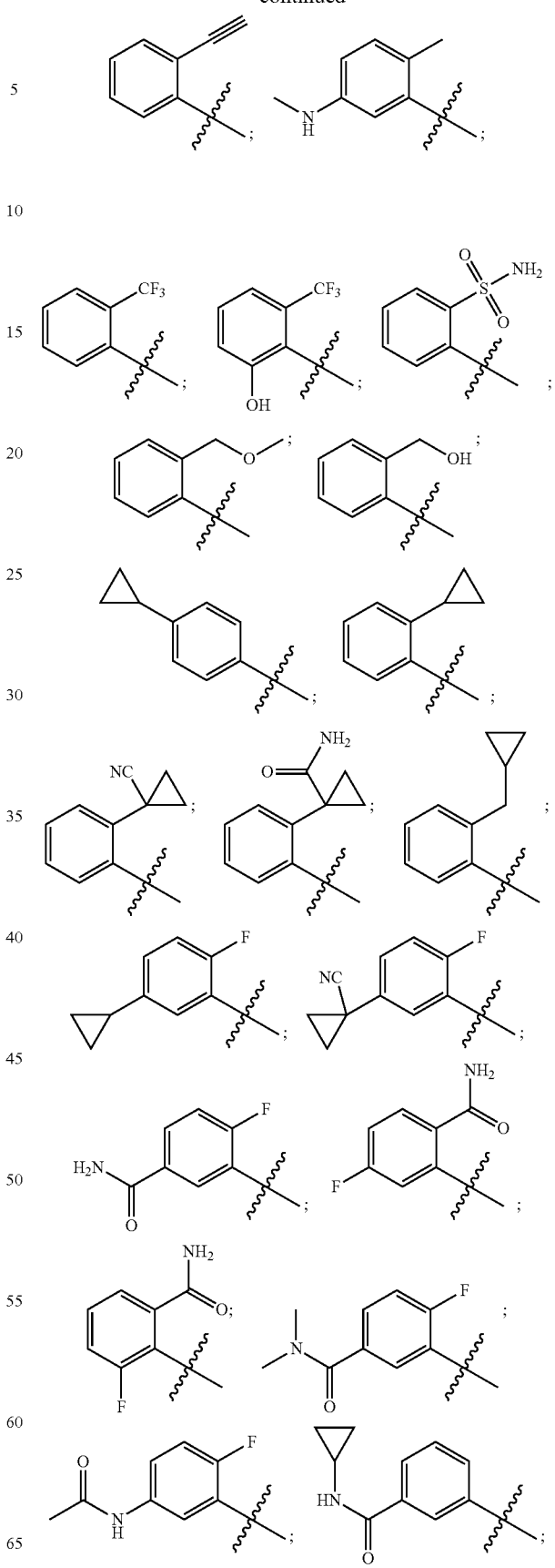

-continued

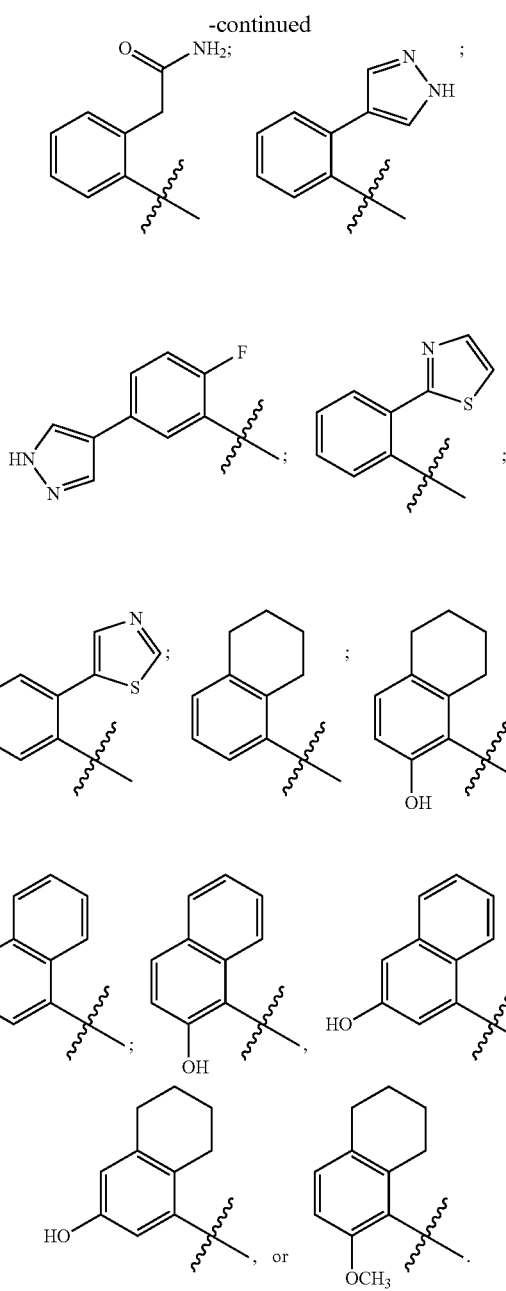

8. The compound of claim 1, wherein $R^{2a}$, when present, is halo.

9. The compound of claim 1, wherein $R^{2a}$, when present, is $C_1$-$C_6$alkyl.

10. The compound of claim 1, wherein $R^{2b}$, when present, is halo.

11. The compound of claim 1, wherein $L^1$ is a bond.

12. The compound of claim 1, wherein $L^2$ is a bond.

13. The compound of claim 1, wherein $R^{3a}$, $R^{3b}$, $R^{4a}$ and $R^{4b}$ are H.

14. The compound of claim 1, wherein W is $CR^6$, wherein $R^6$ is a bond to $L^1$.

15. The compound of claim 1, wherein $R^6$ is H, cyano, $C_1$-$C_6$ alkoxy, amino, aminylalkyl or $C_1$-$C_6$ alkyl.

16. The compound of claim 1, wherein the compound is selected from the group consisting of:

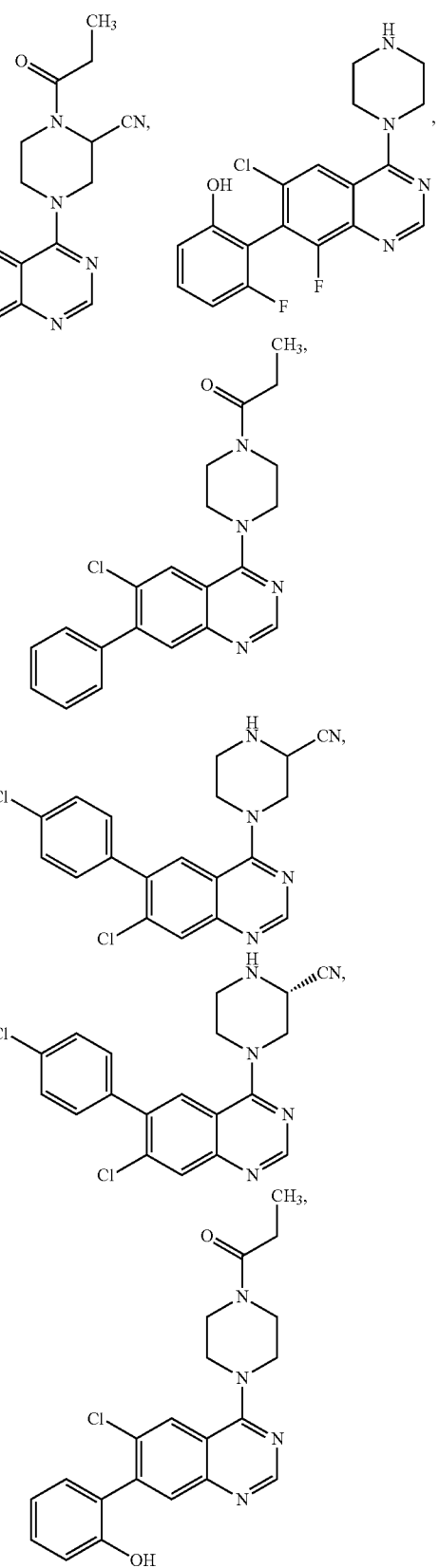

167
-continued
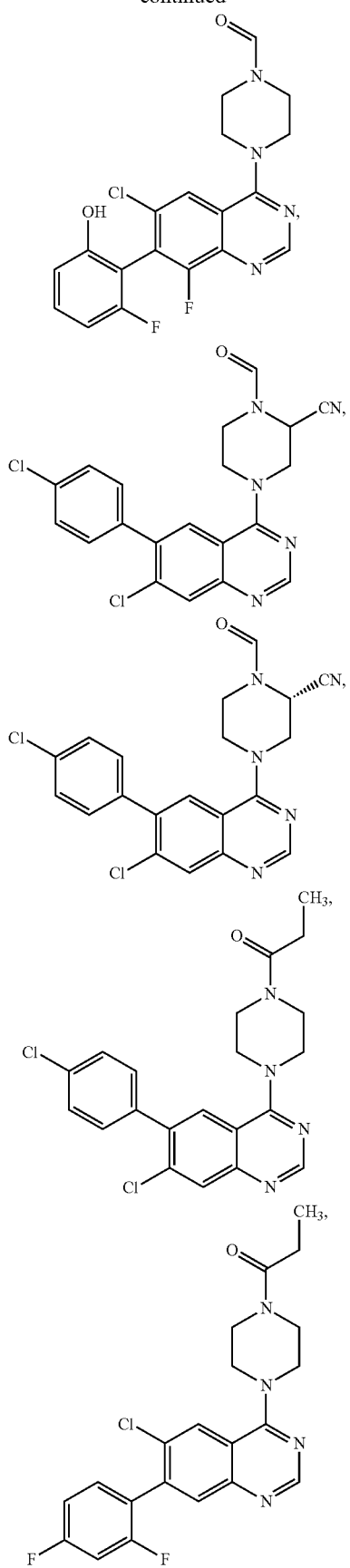
168
-continued
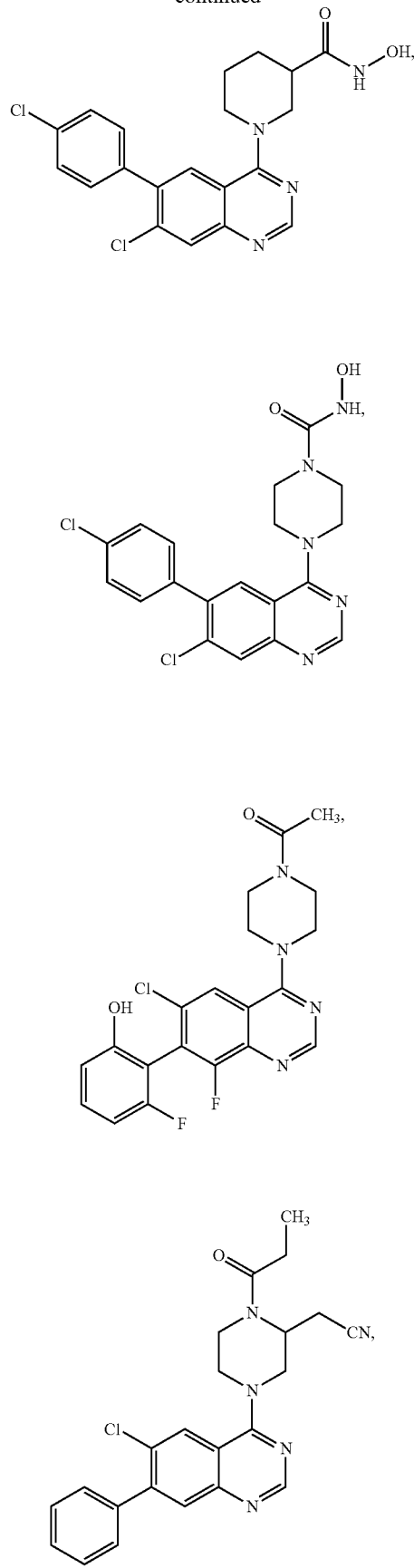

-continued
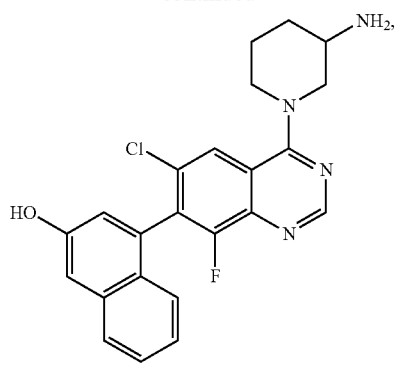
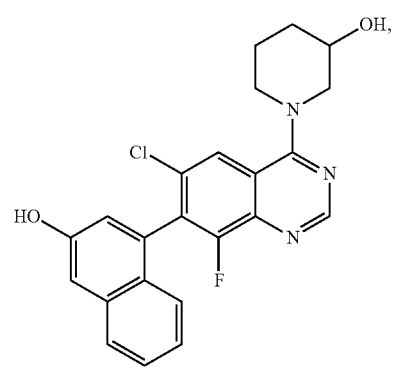
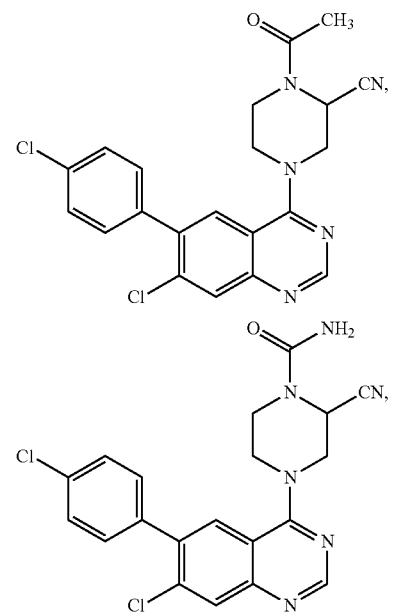
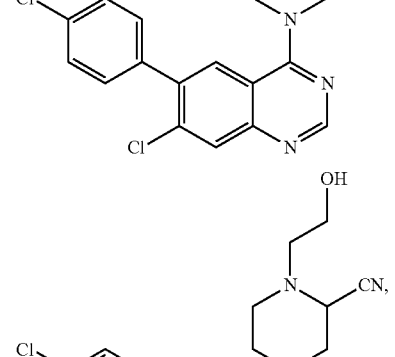
-continued
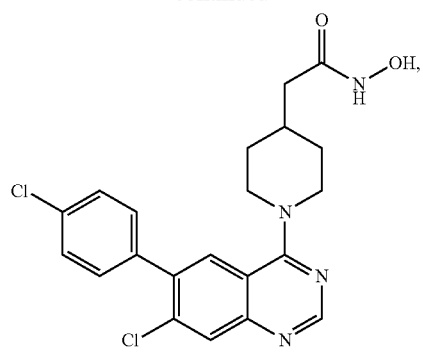
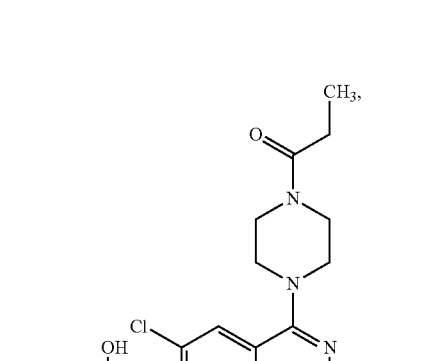
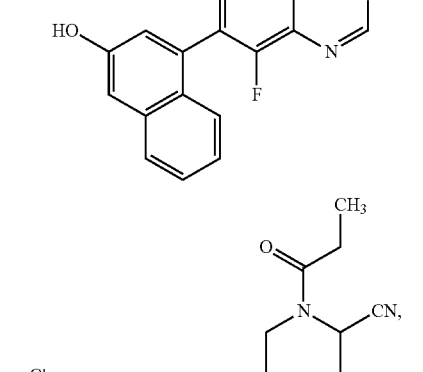
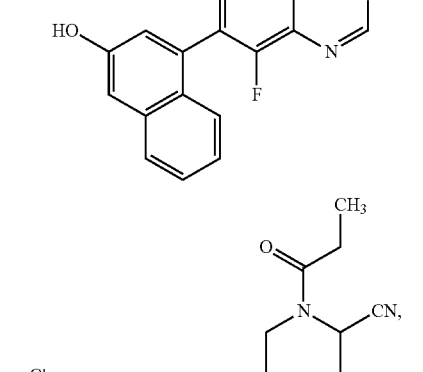

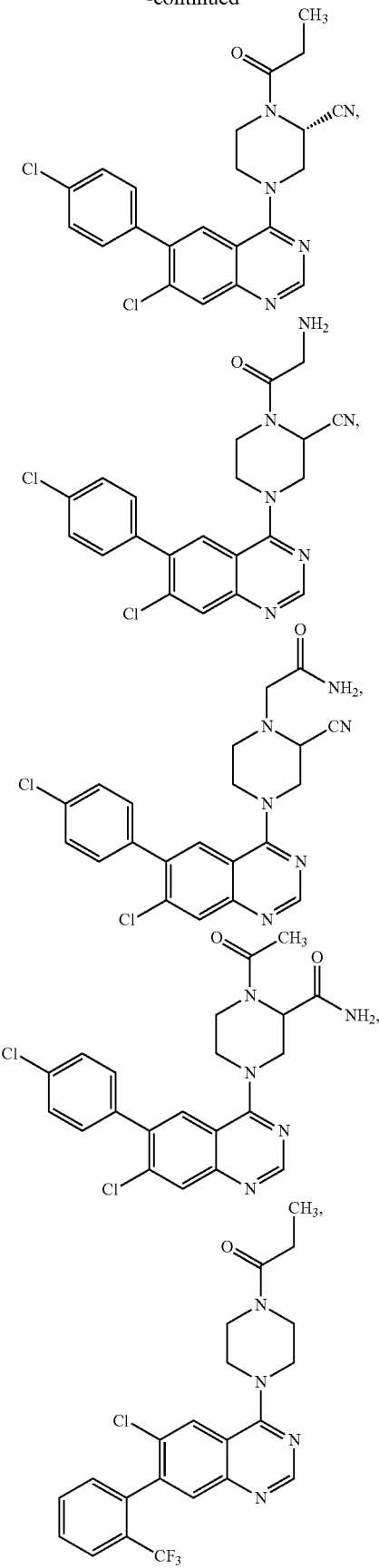
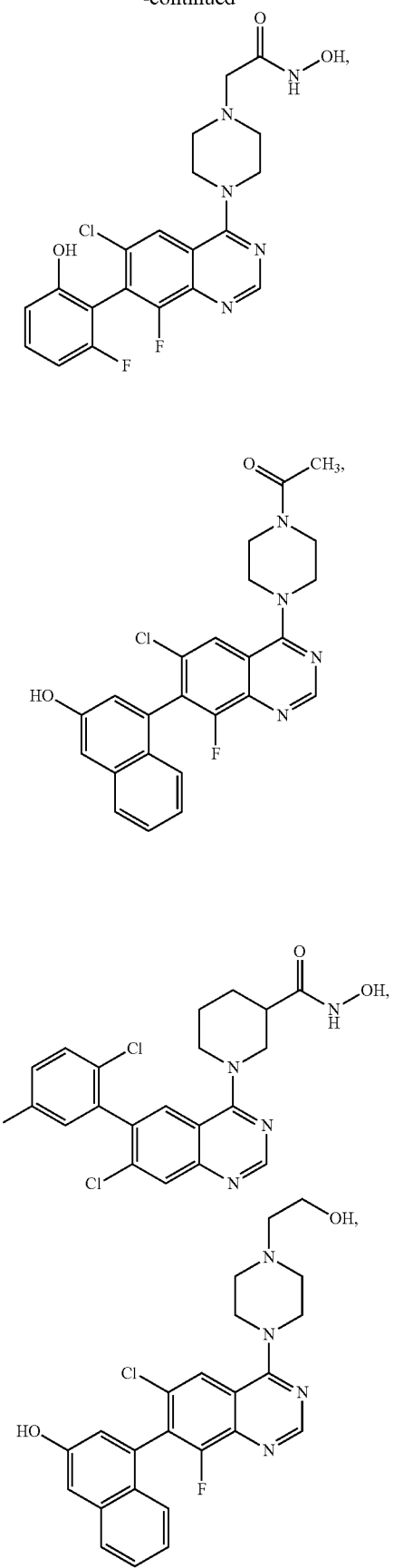

173
-continued
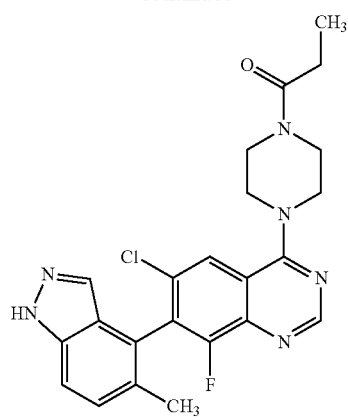
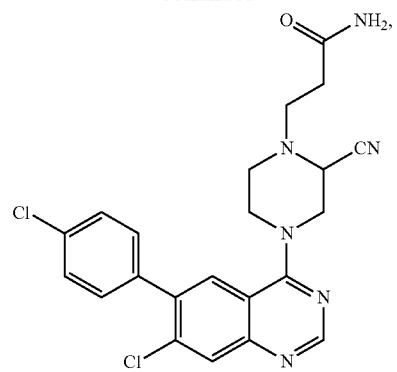
174
-continued
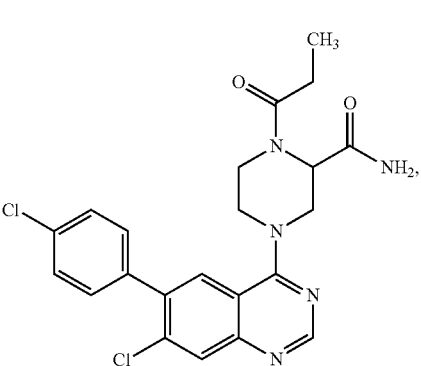
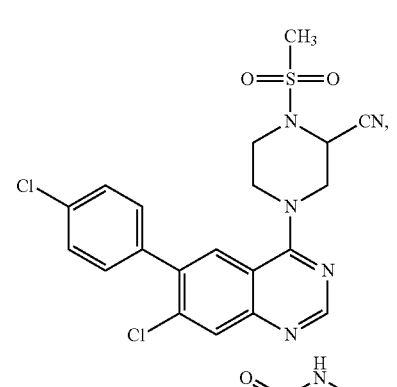
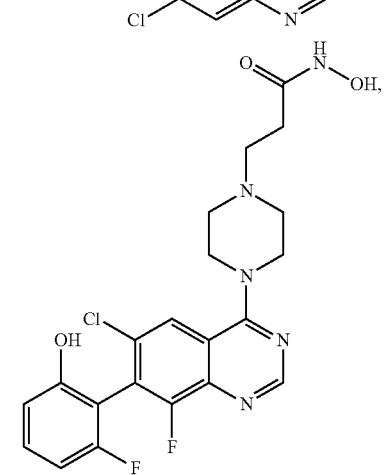

175
-continued
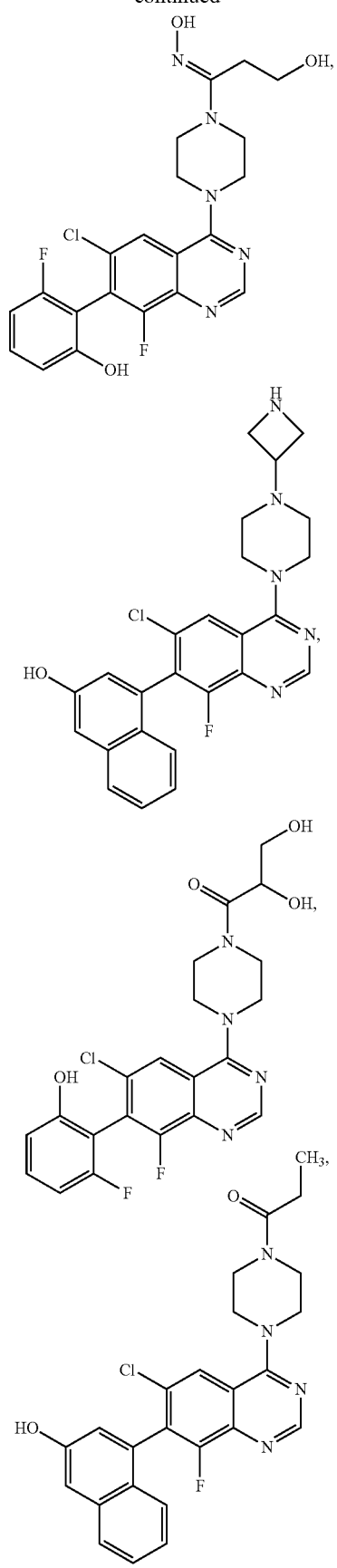
176
-continued
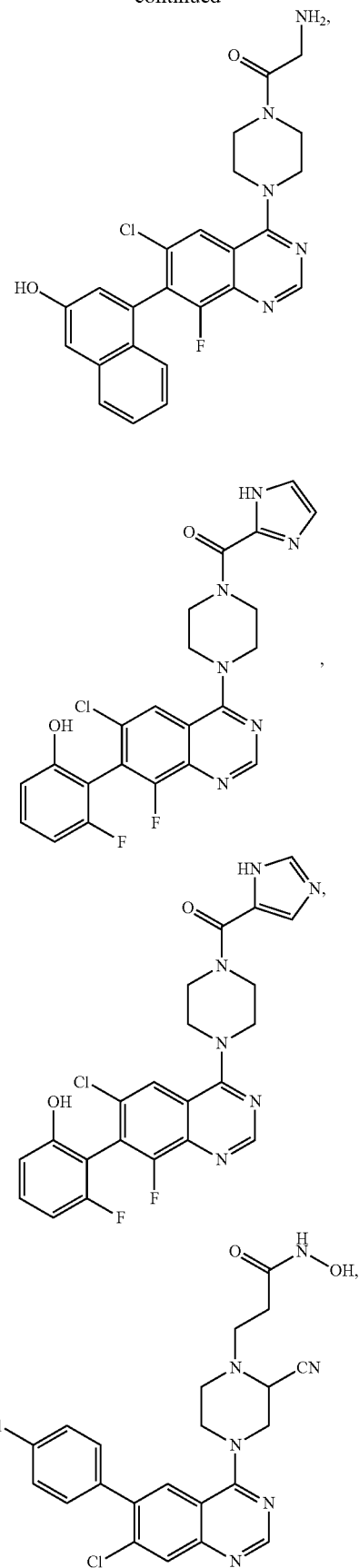

177
-continued
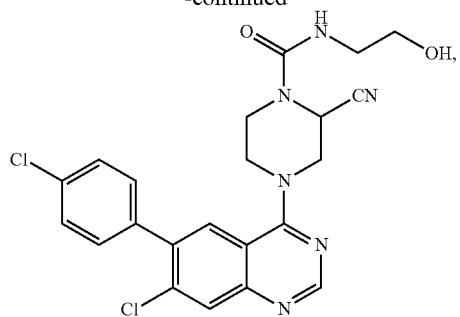
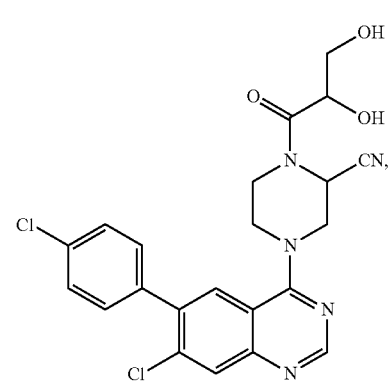
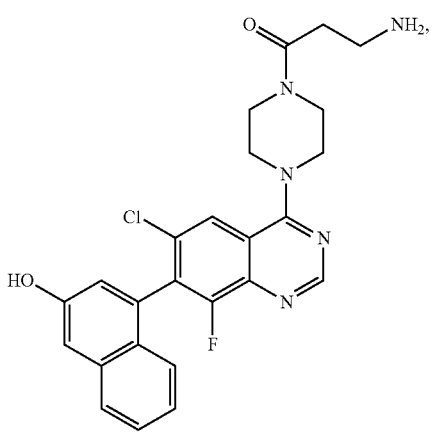
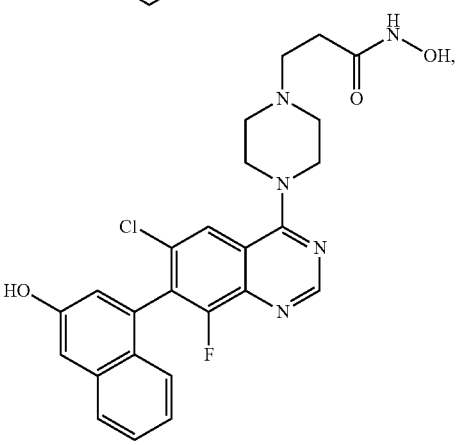
178
-continued
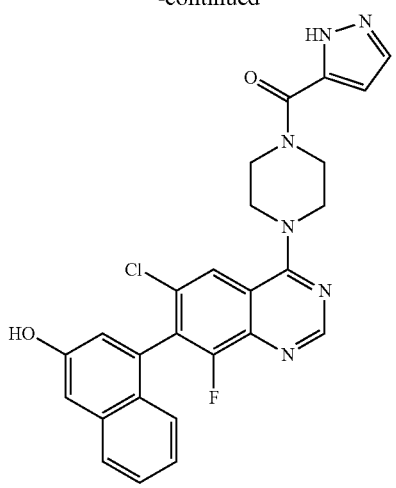
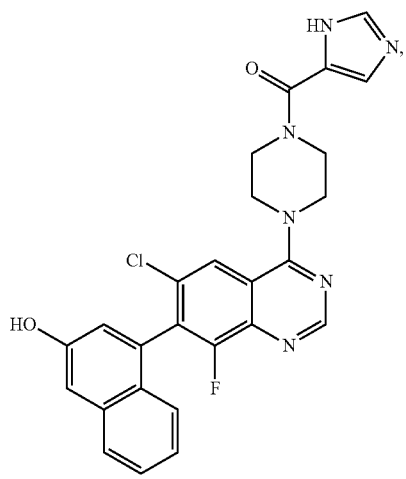
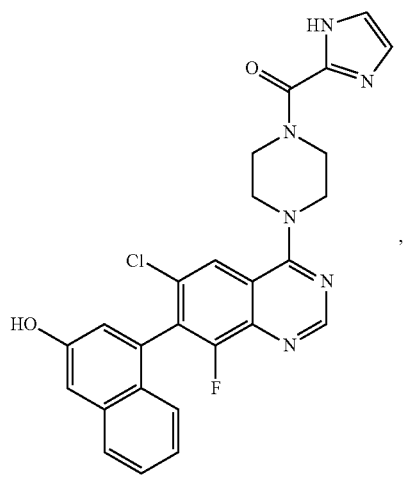

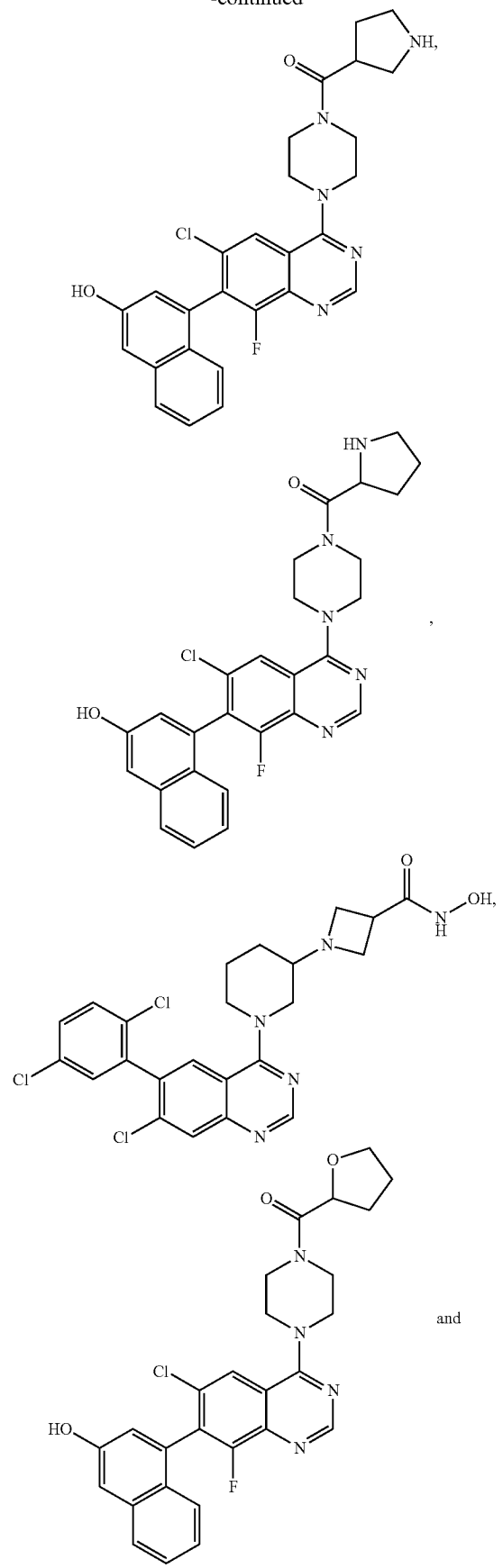
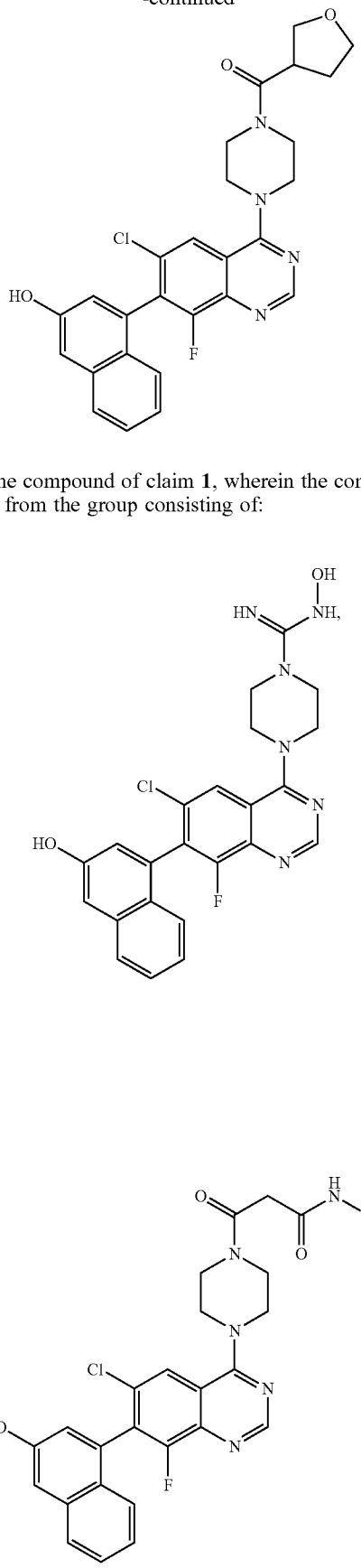
17. The compound of claim 1, wherein the compound is selected from the group consisting of:

-continued
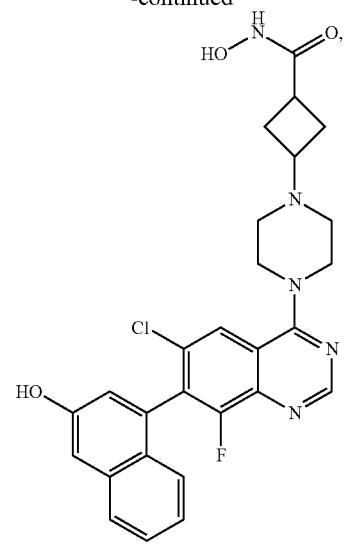
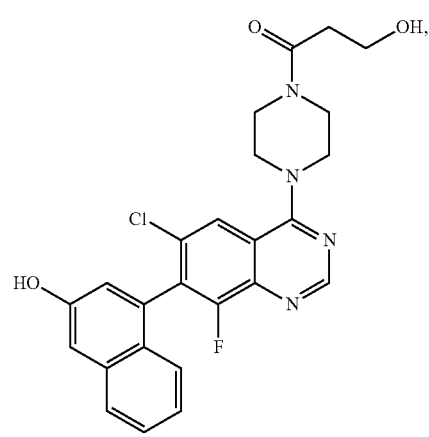
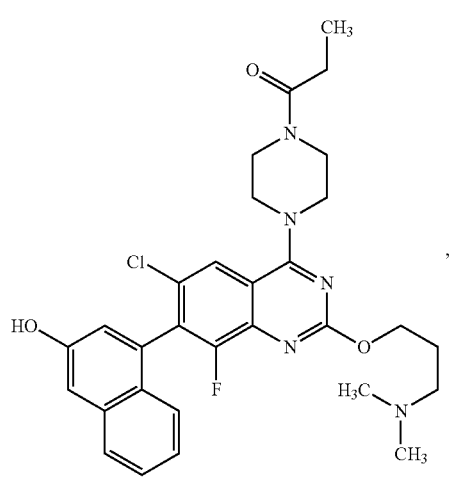
-continued
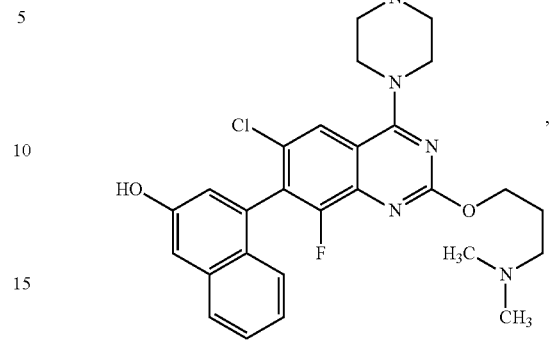
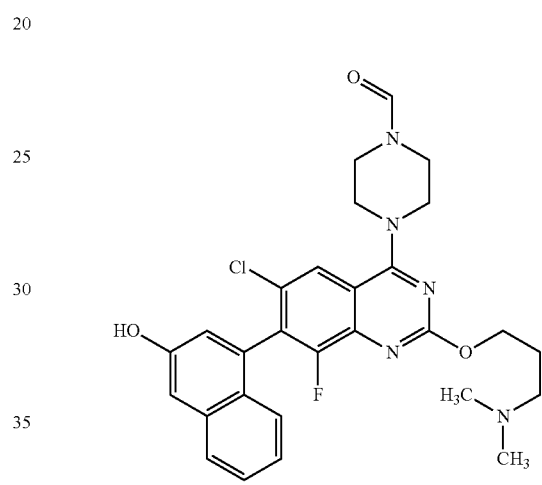
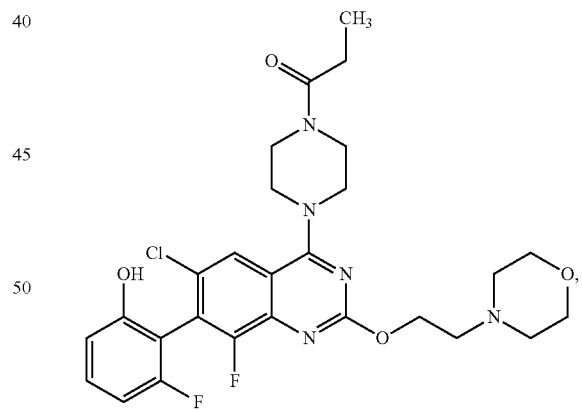
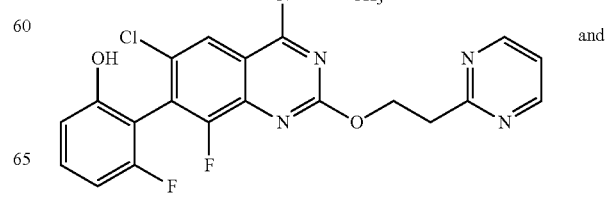
and

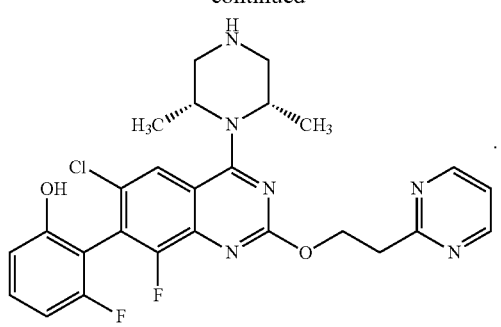
18. The compound of claim 1, wherein T is selected from the group consisting of:
H, —NH₂, —OH, —NHR⁵,
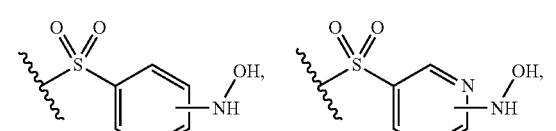
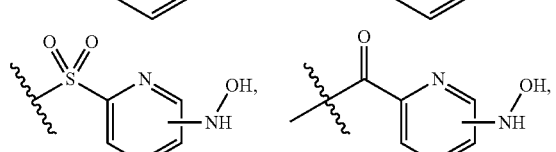
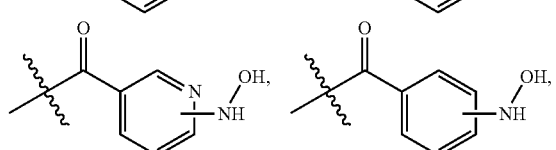
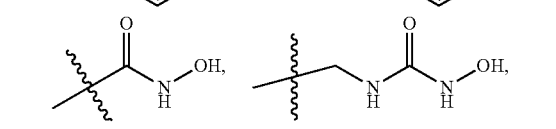
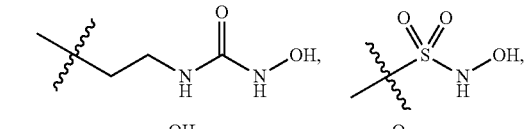
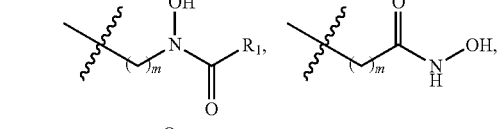
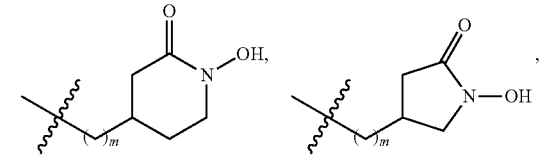
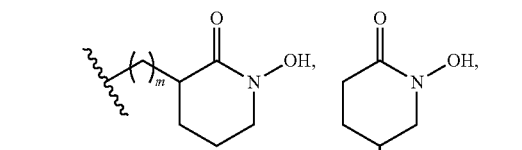
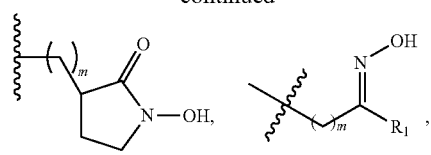
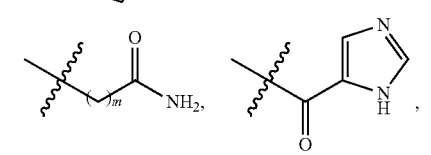
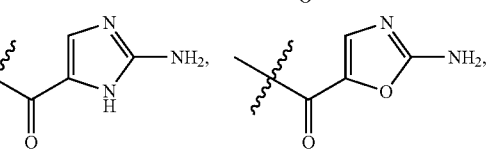
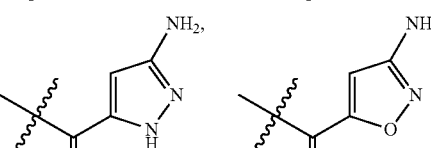
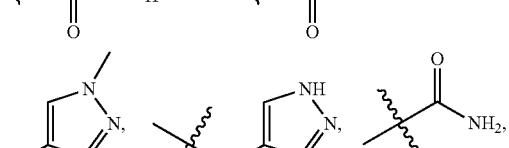
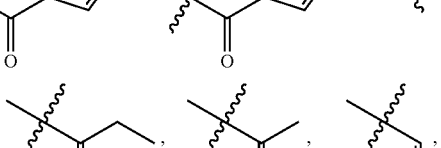
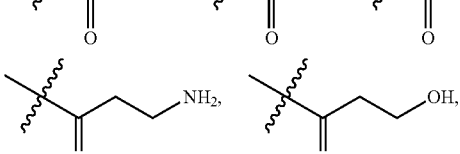
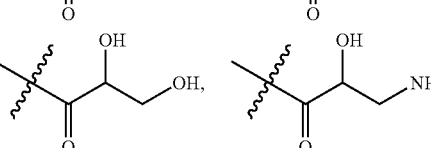
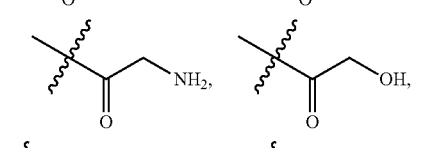
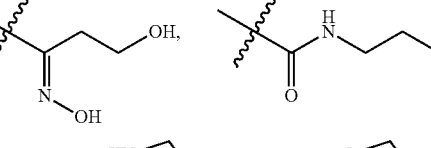
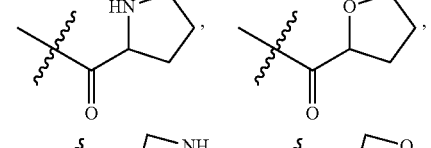
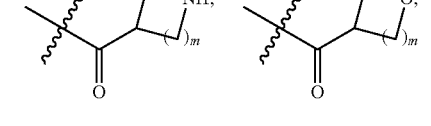

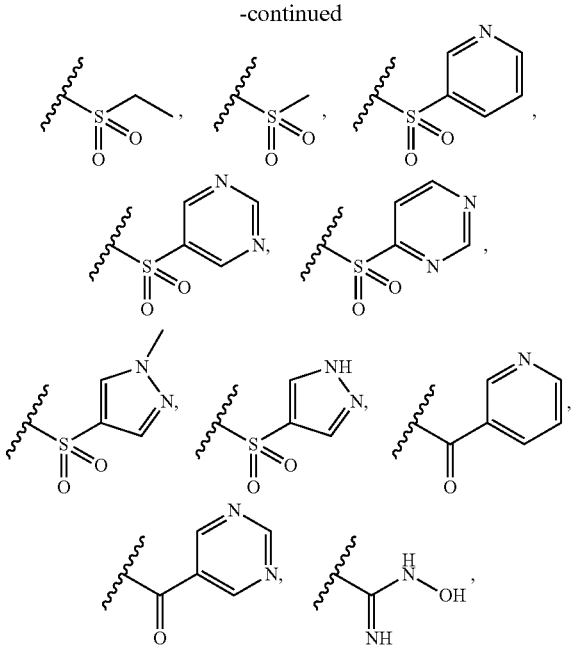

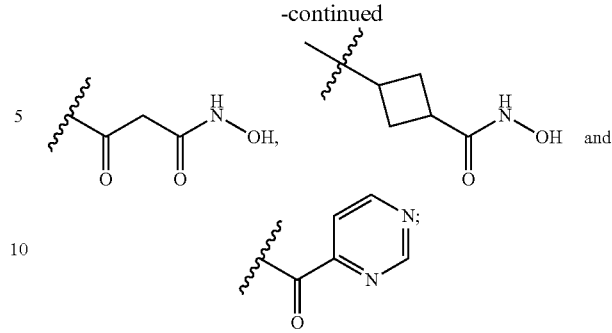

$R^5$ is H or $C_1$-$C_6$ alkyl; and m, when present, is 0, 1, 2, or 3.

19. A pharmaceutical composition comprising a compound of claim 1 and a pharmaceutically acceptable carrier.

20. The pharmaceutical composition of claim 19, wherein the pharmaceutical composition is formulated for oral administration.

21. A method for regulating activity of a K-Ras, H-Ras or N-Ras mutant protein, the method comprising contacting the Ras mutant protein with the compound of claim 1.

* * * * *

UNITED STATES PATENT AND TRADEMARK OFFICE
CERTIFICATE OF CORRECTION

PATENT NO. : 10,011,600 B2
APPLICATION NO. : 15/508387
DATED : July 3, 2018
INVENTOR(S) : Liansheng Li et al.

It is certified that error appears in the above-identified patent and that said Letters Patent is hereby corrected as shown below:

In the Claims

Claim 1, Column 160, Line 28, delete "===== indicates" and insert -- ------ indicates --.

Claim 2, Column 160, Line 49, delete "structures (ID, (I'k)," and insert -- structures (I'j), (I'k), --.

Claim 5, Column 161, Line 57, delete "$C_1$-$C_6$hydroxyl alkyl" and insert -- $C_1$-$C_6$hydroxylalkyl --.

Claim 7, Column 162, Line 1, delete "wherein R has" and insert -- wherein $R^1$ has --.

Claim 7, Column 165, Line 45, delete compound " 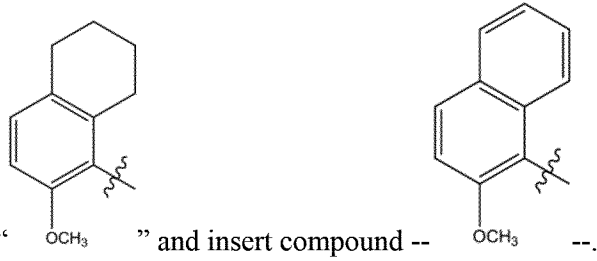 " and insert compound -- --.

Signed and Sealed this
Eighteenth Day of September, 2018

Andrei Iancu
*Director of the United States Patent and Trademark Office*